US008700336B2

(12) United States Patent
Van Den Bulcke et al.

(10) Patent No.: US 8,700,336 B2
(45) Date of Patent: Apr. 15, 2014

(54) TRANSGENIC PLANT EVENT DETECTION

(75) Inventors: Marc Henri Germain Van Den Bulcke, Ghent (BE); Antoon Piet Nelly Raoul Lievens, Ghent (BE); Amaya Leunda, Brussels (BE); Etondoh Guillaume Mbongolo Mbella, Burssels (BE); Elodie Barbau-Piednoir, Meung Sur Loire (FR); Myriam Jacqueline Sylviane Sneyers, Gembloux (BE)

(73) Assignee: Scientific Institute of Pulic Health, Brussels (BE)

( * ) Notice: Subject to any disclaimer, the term of this patent is extended or adjusted under 35 U.S.C. 154(b) by 776 days.

(21) Appl. No.: 12/448,930

(22) PCT Filed: Jan. 29, 2008

(86) PCT No.: PCT/EP2008/051059
§ 371 (c)(1),
(2), (4) Date: Dec. 28, 2009

(87) PCT Pub. No.: WO2008/092866
PCT Pub. Date: Aug. 7, 2008

(65) Prior Publication Data
US 2010/0120032 A1    May 13, 2010

(30) Foreign Application Priority Data

Jan. 29, 2007  (EP) ................................. 07447008
May 16, 2007  (EP) ................................. 07108343

(51) Int. Cl.
*G01N 33/50* (2006.01)
(52) U.S. Cl.
USPC ............................................................ 702/19
(58) Field of Classification Search
None
See application file for complete search history.

(56) References Cited

U.S. PATENT DOCUMENTS

| 2002/0037504 | A1 | 3/2002 | Arahira et al. |
| 2003/0148278 | A1 | 8/2003 | Lauter et al. |
| 2006/0070139 | A1 | 3/2006 | Bing et al. |
| 2006/0282915 | A1 | 12/2006 | Malven et al. |
| 2007/0117106 | A1 | 5/2007 | Remacle et al. |
| 2008/0293057 | A1* | 11/2008 | Remacle et al. ........... 435/6 |
| 2009/0118136 | A1* | 5/2009 | Deng ............................ 506/9 |

FOREIGN PATENT DOCUMENTS

| DE | 199 06 169 A1 | 8/2000 |
| DE | 100 05 808 A1 | 6/2001 |
| EP | 1 724 360 A1 | 11/2006 |
| WO | WO 01/32919 A2 | 5/2001 |
| WO | WO 2005/103301 A2 | 11/2005 |
| WO | WO 2006/108674 A2 | 10/2006 |

OTHER PUBLICATIONS

The Written Opinion of the International Searching Authority for PCT Application No. PCT/EP2008/051059, 10 pages, Jul. 3, 2008.
The Preliminary Report on Patentability for PCT Application No. PCT/EP2008/051059, 12 pages, May 14, 2009.
Delano J et al. Reliable detection and identification of genetically modified maize, soybean, and canola by multiplex PCR analysis. J. Agric. Food Chem. 51(20):5829-34, 2003.
Maksimovic V et al. "PCR detection of genetically modified soybean and maize in food/feed stuffs." Acta Vaterinaria (Beograd) 52(4):201-210, 2002.
Permingeat H et al. "Detection and quantification of transgenes in grains by multiplex and real-time PCR." J. Agric. Food Chem. 50(16):4431-4436, 2002.
Saxena D et al. "Bt toxin is released in root exudates from 12 transgenic corn hybrids representing 3 transformation events." Soil Biology & Biochem. 34:133-137, 2002.
La Paz J et al. "Interlaboratory transfer of a real-time polymerase chain reaction assay for quantitative detection of genetically modified maize event TC-1507." J. of AOAC International, 89(5): 1347-1352, 2006.
Nadal A et al. "A new PCR-CGE (size and color) method for simultaneous detection of genetically modified maize events." Electrophoresis 27:3879-3888, 2006.
Hernandez M et al. "Development of real-time PCR systems based on SYBR(R) Green I, Amplifluor™ and TaqMan(R) technologies for specific quantitative detection of the transgenic maize event GA21." J. of Cereal Science 39:99-107, 2004.
Heck G et al. "Development and characterization of a CP4 EPSPS-based, glyphosate-tolerant corn event." Crop Science 45:329-339, 2005.
Hernandez M et al. "A rapeseed-specific gene, acetyl-CoA carboxylase, can be used as a reference for qualitative and real-time quantitative PCR detection of transgenes from mixed food samples." J. Agric. Food Chem. 49(8)3622-3627, 2001.
Yang L et al. Qualitative and quantitative PCR methods for event-specific detection of genetically modified cotton Mon1445 and Mon531. Transgenic Research 14:817-31, 2005.
Watanabe T et al. "New qualitative detection methods of genetically modified potatoes." Biol. Pharm. Bulletin 27:1333-1339, 2004.
Response to Written Opinion submitted to European Patent Office on Nov. 27, 2008 in connection with PCT/EP2008/051059, 6 pages.
Nemeth A et al., entitled "Sensitive PCR Analysis of Animal Tissue Samples for Fragments of Endogenous and Transgenic Plant DNA," J. Agric. Food Chem., 2004, 52, 6129-6135.
European Commission Joint Research Center Validation Report entitled "Event-specific method for the quantitation of rice line LLRICE62 using real-time PCR," Community Reference Laboratory for GM Food and Feed, dated Jun. 10, 2006, 12 pages.
Baeumler S et al., entitled "A Real-Time Quantitative PCR Detection Method Specific to Widestrike Transgenic Cotton (Event 281-24-236-236/3006-210-23)," J. Agric. Food Chem., 2006, 54, 6527-6534.
Hurst C D et al., entitled "PCR detection of genetically modified soya and maize in foodstuffs," Molecular Breeding 5: 579-586, 1999.
Yang L et al., entitled "Event-Specific Quantitative Detection of Nine Genetically Modified Maizes Using One Novel Standard Reference Molecule," J. Agric. Food Chem., 2007, 55, 15-24.

(Continued)

*Primary Examiner* — Jason Sims
(74) *Attorney, Agent, or Firm* — Amster, Rothstein & Ebenstein LLP

(57) ABSTRACT

The present invention relates to detection of materials derived from transgenic plant events. In particular, the invention provides methods, reagents, kits and reference materials for detecting the presence or absence in a sample of genetic material derived from and attributable to select transgenic plant events.

19 Claims, 8 Drawing Sheets

(56) References Cited

OTHER PUBLICATIONS

Hernandez M et al., entitled "Development and Comparison of Four Real-Time Polymerase Chain Reaction Systems for Specific Detection and Quantification of *Zea mays* L.," J. Agric. Food Chem., 2004, 52, 4632-4637.

Peano C et al., entitled "Multiplex polymerase chain reaction and ligation detection reaction/universal array technology for the traceability of genetically modified organisms in food," Analytical Biochemistry, 346 (2005) 90-100.

Van Den Bulcke M et al., entitled "A theoretical introduction to "Combinatory SYBR Green qPCR Screening", a matrix-based approach for the detection of materials derived from genetically modified plants," Anal Bioanal Chem (2010) 396; 2113-2123.

Leimanis S et al., entitled "A microarray-based detection system for genetically modified (GM) food ingredients," Plant Molecular Biology (2006) 61:123-139.

Jian-Chang Z et al., entitled "Detection of genetically modified organisms in food and animal feed by polymerase chain reaction," Journal of Hygiene Research, vol. 34, No. 6, Nov. 2005, 732-734.

\* cited by examiner

FIGURE 1A

ADH (Zea Mays)

GAATTCGAGCTCGGTACCCGGGGTATCCGTCGTTTCCCATCTCTTCCTCCTTTAGTAGCT
ACCACTATATAAATCAGGGCTCATTTTCTCGCTCCTCACAGGCTCATCTCGCTTTGGATC
GATTGGTTTCGTAACTGGTGAGGGACTGAGGGTCTCGGAGTGGGTC (SEQ ID NO: 32)

ADH (Zea mays)

GAATTCGCCCTTAATCGATCCAAAGCGAGATGAGCCTGTGAGGAGCGAGAAAATGAGCC
CTGATTTATATAGTGGTAGCTCTAAAGGAGGAAGAGAAAGGGCGAATTC (SEQ ID NO: 70)

Lectin (Glycine max)

GAATTGCGCCCTTCATTACCTATGATGCCTCCACCAACCTCTTGTGTTGCTTCTTTGGTT
CATCCTTCGCAGAGAAGCAGCTATATCCTCTCCGGATGTGGTCGATTTGAAGACTTCTCT
TCCCGAGTTGGGGGGTTGAGGATAGGGGTTCTCGTGCGTGCCACGTGGGACTCGACAT
AGCCTGGGGAATCGCATGACGTGCTTAAGGGCGAATTC (SEQ ID NO: 33)

SLTM (Glycine max)

GAATTCGCCCTTAACCGGTAGCGTTGCCAGCTTCGCCGCTTCCTTCAACTTCACCTTCTA
TGCCCCTGACACAAAAAGGCTTGCAGATGGGCTAAGGGCGAATTC (SEQ ID NO: 71)

p35S (longer)

GCTCGAATTCGCCCTTGACAGTGGTCCCAAAGATGGACCCCCACCCACGAGGAACATC
GTGGAAGAAGAAGACGTTCCAACCACGTCTTCAAAGCAAGTGGATTGATGTGATATCTC
CACTGACGTAAGGGATGACGCACAATCCCACTATCCTTCGCAAGACAAGGGCGAATTCG
TAA (SEQ ID NO: 34)

FIGURE 1B p35S (short)

GAATTCGCCCTTGGGTCTTGCGAAGGATAGTGGGATTGTGCGTCATCCCTTACGTCAGT
GGAGATATCACATCAATCCACTTGCTTTAAGGGCGAATTC (SEQ ID NO: 72)

tNOS (TNOS-D)

GCTCGAATTCGCCCTTTATCCTAGGTTGCGCGCTATATTTTGTTTTCTATCGCGTATTAAA
TGTATAATTGCGGGACTCTAATCAAGGGCGAATTCGTAA (SEQ ID NO: 35)

CRY1Ab

GCTCGAATTCGCCCTTACGCCTTCCTGGTGCAAATCGAGCAGCTCATCAACCAGAGGAT
CGAGGAGTTCGCCAGGAACCAGGAAGGGCGAATTCGTAA (SEQ ID NO: 36)

CRY 1Ab

GCTCGAATTCGCCCTTACCGGTTACACTCCCATCGACATCTCCCTCTCCCTCACGCAGTT
CCTGCTCAGCGAGTTCGTGCCAGGTGCTGAAGGGCGAATTCGTAA (SEQ ID NO: 37)

CRY 1Ab (Bt11)

GCTCGAATTCGCCCTTCAGCACCTGGCACGAACTCGCTGAGCAGAAACTGTGTCAAGGA
CAAGGAGATGTCGATGGGAGTGTAACCGGTAAGGGCGAATTTCGTAA (SEQ ID NO: 38)

CRY 1Ab (MON 810)

GAATTCGCCCTTCAGCACCTGGCACGAACTCGCTGAGCAGGAACTGCGTGAGGGAGAG
GGAGATGTCGATGGGAGTGTAACCGGTAAGGGCGAATTC (SEQ ID NO: 73)

FIGURE 1C

PAT/bar

GCTCGAATTCGCCCTTCGTCAACCACTACATCGAGACAAGCACGGTCAACTTCCGTACC
GAGCCGCAGGAACCGCAGGAGTGGACAAGGGCGAATTCGTAA (SEQ ID NO: 39)

PAT/pat

GCTCGAATTCGCCCTTCCGCGGTTTGTGATATCGTTAACCATTACATTGAGACGTCTACA
GTGAACTTTAGGACAGAGCCACAAACACCACAAGAGTGGATTGATGATCTAGAGAGGTT
GCAAGAAGGGCGAATTCGTAA (SEQ ID NO: 40)

Rbcl

GCTCGAATTCGCCCTTAGGTCTAAGGGGTAAGCTACATAACAGATATATTGATCTGGGTC
CCCAGGAACGGGCTCGATGTGATAGCATCGTCCTTTGTAACGATCAAGGCTAAGGGCGA
ATTCGTAA (SEQ ID NO: 41)

Rbcl (OSR Wt)

GCTCGAATTCGCCCTTAGGTCTAAGGGGTAAGCTACATACGCAATAAATTGAGTTTCTTC
TCCTGGAACGGGCTCGATGTGGTAGCATCGTCCTTTGTAACGATCAAGGCTAAGGGCGA
ATTCGTAA (SEQ ID NO: 42)

tNOS (TNOS-L)

GCTCGAATTCGCCCGTTAAATGTATAATTGCGGGACTCTAATCATAAAAACCCATCTCAT
AAATAACGTCATGCATTACATGTTAATTATTACATGCTTAACGTAATTCAACAGAAATTATA
TGATAATCATCGCAAGACCGGCAACAGGATTCAATCTTAAGAAACTTTATTGCCAAATGT
TTGAACGAAGGGCGAATTCGTAA (SEQ ID NO: 43)

FIGURE 1D

**ACC (*Brassica napus*)**

GCTCGAATTCGCCCTTGGCGCAGCATCGGCTCTTCTGCATAGTACCGTTTCTCCATCGA
CCAATGGAACGAATGTCTAATAGGTGTTCGTCCTTCATCTCGCTCGATTATACAGCTCAC
CACACCCACACCTGCGGAACACAGGCTCGAACTAACTTCTTCCTCTTTGAGAATTTTCTC
CACTCTTTCTTGAGCTTGGTCCTCCTCATTCTCAAGGGCGAATTCGTAA (SEQ ID NO: 44)

CP4-EPSPS

CTCGAATTCGCCCTTGAATGCGGACGGTTCCGGAAAGGCCAGAGGATTTGCGGGCGGT
TGCGGGCCGGCTGCTTGCACCGTGAAGCATGCAGGCTGTAGCCACTGATAAGGGCGAA
TTCGTAA (SEQ ID NO: 45)

CP4-EPSPS

GCTCGAATTCGCCCTTGGCTCTGAGCTTCGTCCTCTTAAGGTCATGTCTTCTGTTTCCAC
GGCGTGCATGCTTCACGGTGCAAGCAGCCGGCCCGCAACCGCCCGCAAATCCTCTGGC
CTTTCCGGAACCGTCCGCATTCAAGGGCGAATTCGTAA (SEQ ID NO: 46)

CP4-EPSPS (GT 73)

GAATTCGCCCTTTGAAGGACCTGTGGGAGATAGACTTGTCACCTGGAATACGGACGGTT
CCAGAAAGACCAGAGGACTTACGAGCAGTTGCTGGACGGCTGCTTGCACCGTGAAGCA
TGCAAGGGCGAATTC (SEQ ID NO: 74)

CP4-EPSPS RRS

GAATTCGCCCTTTGAAGGACCGGTGGGAGATCGACTTGTCGCCGGGAATGCGGACGGT
TCCGGAAAGGCCAGAGGATTTGCGGGCGGTTGCGGGCCGGCTGCTTGCACCGTGAAG
CATGCAAGGGCGAATTC (SEQ ID NO: 75)

FIGURE 1E

Phospholipase D (Oryza sativa)

GCTCGAATTCGCCCTTGCTTAGGGAACAGGGAAGTAAAGTTGAATGGTGAGTATGAACC
TGCAGGTCGCCCTTTGGATGGCACAGACTATGCTAAGAAGGGCGAATTCGTAA (SEQ ID
NO: 52)

CP4-EPSP

GCTCGAATTCGCCCTTGGACCTGTGGGAGATAGACTTGTCGCCGGGAATGCGGACGGT
TCCGGAAAGGCCAGAGGATTTGCGGGCGGTTGCGGGCCGGCTGCTTGCACCGTGAAG
CATGCAAGGGCGAATTCGTAA (SEQ ID NO: 53)

CP4-EPSP

GCTCGAATTCGCCCTTGGACCTGTGGGAGATAGACTTGTCACCTGGAATACGGACGGTT
CCAGAAAGACCAGAGGACTTACGAGCAGTTGCTGGACGGCTGCTTGCACCGTGAAGCA
TGCAAGGGCGAATTCGTAA (SEQ ID NO: 54)

Cruciferin (Brassica)

GCTCGAATTCGCCCTTCAGCTCAACAGTTTCCAAACGAGTGCCAACTAGACCAGCTCAA
TGCGCTGGAGCCGTCACACGTACTTAAGGCTGAGGCTGGTCGAAGGGCGAATTCGTAA
(SEQ ID NO: 55)

GluA3 (Sugarbeet)

GAATTCGCCCTTGACCTCCATATTACTGAAAGGAAGCCAAAAGGGATCAATTAAGTGCTC
TACGAAGTTTAAAGTATGTGCCGCTCTCAAGACTGAACATGGCACTGTGAACAGGATGG
AGCAATTACTCAAGGGCGAATTC (SEQ ID NO: 76)

FIGURE 1F

Sah-7 (Cotton)

GAATTCGCCCTTAGTTTGTAGGTTTTGATGTTACATTGAGTGACAGTGAATGAAAGGGTG
TGTAAACATAAAATAATGGGAACAACCATGACATGTTGGACTGGATCAGTAGGCGGTTCA
AAGATGCAAGGGCGAATTC (SEQ ID NO: 77)

UGPase (Potato)

GAATTCGCCCTTGGACATGTGAAGAGACGGAGCGCAGATTCCCCAGTAAGGAGGTGTG
AGGGGCTAGTTGTAGAGGGTACGCGGAGGGGTAGAGGTAGGAAGGGCGAATTC (SEQ ID NO: 78)

(A)

|  |  | RRS 100% | | |
|---|---|---|---|---|
| p35S short + tNOS | Cts | 22.51 | 22.09 | 22.13 |
|  | Tm | 71.5 and 76 | 71.5 and 76 | 72 and 76.5 |
|  | Mean Cts | 22.25 | | |
|  | St Dev | 0.232 | | |
| p35S short | Cts | 22.99 | 22.76 | 22.62 |
|  | Tm | 76.50 | 76.50 | 76.50 |
|  | Mean Cts | 22.79 | | |
|  | St Dev | 0.186 | | |
| tNOS | Cts | 23.03 | 22.83 | 22.76 |
|  | Tm | 72.00 | 72.00 | 72.00 |
|  | Mean Cts | 22.88 | | |
|  | St Dev | 0.142 | | |

(B)

RRS 100% 230107 multiplex

SEQUENCE LISTING

<160> NUMBER OF SEQ ID NOS: 79

<210> SEQ ID NO 1
<211> LENGTH: 23
<212> TYPE: DNA
<213> ORGANISM: Artificial Sequence
<220> FEATURE:
<223> OTHER INFORMATION: primer: Zea Mays (adh-1)

<400> SEQUENCE: 1
cgtcgtttcc catctcttcc tcc                                          23

<210> SEQ ID NO 2
<211> LENGTH: 20

-continued

```
<212> TYPE: DNA
<213> ORGANISM: Artificial Sequence
<220> FEATURE:
<223> OTHER INFORMATION: primer: Zea Mays (adh-1)

<400> SEQUENCE: 2
ccactccgag accctcagtc                                                    20

<210> SEQ ID NO 3
<211> LENGTH: 15
<212> TYPE: DNA
<213> ORGANISM: Artificial Sequence
<220> FEATURE:
<223> OTHER INFORMATION: primer: Brassica napus (ACC)

<400> SEQUENCE: 3
ggcgcagcat cggct                                                         15

<210> SEQ ID NO 4
<211> LENGTH: 22
<212> TYPE: DNA
<213> ORGANISM: Artificial Sequence
<220> FEATURE:
<223> OTHER INFORMATION: primer: Brasicca napus (ACC)

<400> SEQUENCE: 4
gagaatgagg aggaccaagc tc                                                 22

<210> SEQ ID NO 5
<211> LENGTH: 22
<212> TYPE: DNA
<213> ORGANISM: Artificial Sequence
<220> FEATURE:
<223> OTHER INFORMATION: primer: Glycine max (lectin)

<400> SEQUENCE: 5
cattacctat gatgcctcca cc                                                 22

<210> SEQ ID NO 6
<211> LENGTH: 18
<212> TYPE: DNA
<213> ORGANISM: Artificial Sequence
<220> FEATURE:
<223> OTHER INFORMATION: primer: Glycine max (lectin)

<400> SEQUENCE: 6
aagcacgtca tgcgattc                                                      18

<210> SEQ ID NO 7
<211> LENGTH: 20
<212> TYPE: DNA
<213> ORGANISM: Artificial Sequence
<220> FEATURE:
<223> OTHER INFORMATION: primer: 35S promoter of Cauliflower Mosaic
      Virus

<400> SEQUENCE: 7
gacagtggtc ccaaagatgg                                                    20

<210> SEQ ID NO 8
<211> LENGTH: 20
<212> TYPE: DNA
<213> ORGANISM: Artificial Sequence
<220> FEATURE:
<223> OTHER INFORMATION: primer: 35S promoter of Cauliflower Mosaic
      Virus

<400> SEQUENCE: 8
```

```
gtcttgcgaa ggatagtggg                                              20
```

<210> SEQ ID NO 9
<211> LENGTH: 28
<212> TYPE: DNA
<213> ORGANISM: Artificial Sequence
<220> FEATURE:
<223> OTHER INFORMATION: primer: 3' terminator of the Agrobacterium
      tumefaciens nopaline synthetase gene (TNOS-D)

<400> SEQUENCE: 9

```
gattagagtc ccgcaattat acatttaa                                     28
```

<210> SEQ ID NO 10
<211> LENGTH: 25
<212> TYPE: DNA
<213> ORGANISM: Artificial Sequence
<220> FEATURE:
<223> OTHER INFORMATION: primer: 3' terminator of the Agrobacterium
      tumefaciens nopaline synthetase gene

<400> SEQUENCE: 10

```
ttatcctagk ttgcgcgcta tattt                                        25
```

<210> SEQ ID NO 11
<211> LENGTH: 20
<212> TYPE: DNA
<213> ORGANISM: Artificial Sequence
<220> FEATURE:
<223> OTHER INFORMATION: primer: Cry1Ab of Bacillus thuringiensis

<400> SEQUENCE: 11

```
accggttaca ctcccatcga                                              20
```

<210> SEQ ID NO 12
<211> LENGTH: 19
<212> TYPE: DNA
<213> ORGANISM: Artificial Sequence
<220> FEATURE:
<223> OTHER INFORMATION: primer: Cry1Ab of Bacillus thuringiensis

<400> SEQUENCE: 12

```
cagcacctgg cacgaactc                                               19
```

<210> SEQ ID NO 13
<211> LENGTH: 23
<212> TYPE: DNA
<213> ORGANISM: Artificial Sequence
<220> FEATURE:
<223> OTHER INFORMATION: primer: phosphinothricin acetyltransferase
      (PAT) gene bar of Streptomyces hygroscopicus

<400> SEQUENCE: 13

```
cgtcaaccac tacatcgaga caa                                          23
```

<210> SEQ ID NO 14
<211> LENGTH: 19
<212> TYPE: DNA
<213> ORGANISM: Artificial Sequence
<220> FEATURE:
<223> OTHER INFORMATION: primer: phosphinothricin acetyltransferase
      (PAT) gene bar of Streptomyces hygroscopicus

<400> SEQUENCE: 14

```
gtccactcct gcggttcct                                               19
```

```
<210> SEQ ID NO 15
<211> LENGTH: 20
<212> TYPE: DNA
<213> ORGANISM: Artificial Sequence
<220> FEATURE:
<223> OTHER INFORMATION: primer: phosphinothricin acetyltransferase
      (PAT) gene pat of Streptomyces viridochromogenes

<400> SEQUENCE: 15
ccgcggtttg tgatatcgtt                                                    20

<210> SEQ ID NO 16
<211> LENGTH: 25
<212> TYPE: DNA
<213> ORGANISM: Artificial Sequence
<220> FEATURE:
<223> OTHER INFORMATION: primer: phosphinothricin acetyltransferase
      (PAT) gene pat of Streptomyces viridochromogenes

<400> SEQUENCE: 16
tcttgcaacc tctctagatc atcaa                                              25

<210> SEQ ID NO 17
<211> LENGTH: 25
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 17
ggctctgagc ttcgtcctcc taagg                                              25

<210> SEQ ID NO 18
<211> LENGTH: 21
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 18
atcagtggct acagcctgca t                                                  21

<210> SEQ ID NO 19
<211> LENGTH: 22
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 19
gaatgcggac ggttccggaa ag                                                 22

<210> SEQ ID NO 20
<211> LENGTH: 25
<212> TYPE: DNA
<213> ORGANISM: Artificial Sequence
<220> FEATURE:
<223> OTHER INFORMATION: primer: Oryza sativa

<400> SEQUENCE: 20
gcttagggaa cagggaagta aagtt                                              25

<210> SEQ ID NO 21
<211> LENGTH: 23
<212> TYPE: DNA
```

```
<213> ORGANISM: Artificial Sequence
<220> FEATURE:
<223> OTHER INFORMATION: primer: Oryza sativa

<400> SEQUENCE: 21
cttagcatag tctgtgccat cca                                              23

<210> SEQ ID NO 22
<211> LENGTH: 18
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 22
gcatgcttca cggtgcaa                                                    18

<210> SEQ ID NO 23
<211> LENGTH: 24
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 23
ggacctgtgg gagatagact tgtc                                             24

<210> SEQ ID NO 24
<211> LENGTH: 22
<212> TYPE: DNA
<213> ORGANISM: Artificial Sequence
<220> FEATURE:
<223> OTHER INFORMATION: primer: Brassica napus (cruciferin)

<400> SEQUENCE: 24
cagctcaaca gtttccaaac ga                                               22

<210> SEQ ID NO 25
<211> LENGTH: 20
<212> TYPE: DNA
<213> ORGANISM: Artificial Sequence
<220> FEATURE:
<223> OTHER INFORMATION: primer: Brassica napus (cruciferin)

<400> SEQUENCE: 25
cgaccagcct cagccttaag                                                  20

<210> SEQ ID NO 26
<211> LENGTH: 20
<212> TYPE: DNA
<213> ORGANISM: Artificial Sequence
<220> FEATURE:
<223> OTHER INFORMATION: primer: generic plant (Rbcl)

<400> SEQUENCE: 26
aggtctaadg grtaagctac                                                  20

<210> SEQ ID NO 27
<211> LENGTH: 20
<212> TYPE: DNA
<213> ORGANISM: Artificial Sequence
<220> FEATURE:
<223> OTHER INFORMATION: primer: generic plant (Rbcl)

<400> SEQUENCE: 27
```

```
agycttgatc gttacaaagg                                              20

<210> SEQ ID NO 28
<211> LENGTH: 23
<212> TYPE: DNA
<213> ORGANISM: Artificial Sequence
<220> FEATURE:
<223> OTHER INFORMATION: primer: 3' terminator of the Agrobacterium
      tumefaciens nopaline synthetase gene (TNOS-L)

<400> SEQUENCE: 28
cgttcaaaca tttggcaata aag                                          23

<210> SEQ ID NO 29
<211> LENGTH: 26
<212> TYPE: DNA
<213> ORGANISM: Artificial Sequence
<220> FEATURE:
<223> OTHER INFORMATION: primer: 3' terminator of the Agrobacterium
      tumefaciens nopaline synthetase gene (TNOS-L)

<400> SEQUENCE: 29
aaatgtataa ttgcgggact ctaatc                                       26

<210> SEQ ID NO 30
<211> LENGTH: 20
<212> TYPE: DNA
<213> ORGANISM: Artificial Sequence
<220> FEATURE:
<223> OTHER INFORMATION: primer: Cry1Ab of Bacillus thuringiensis

<400> SEQUENCE: 30
gacatcatct ggggyatctt                                              20

<210> SEQ ID NO 31
<211> LENGTH: 20
<212> TYPE: DNA
<213> ORGANISM: Artificial Sequence
<220> FEATURE:
<223> OTHER INFORMATION: primer: Cry1Ab of Bacillus thuringiensis

<400> SEQUENCE: 31
gcgctgttca tgtcgttgaa                                              20

<210> SEQ ID NO 32
<211> LENGTH: 166
<212> TYPE: DNA
<213> ORGANISM: Artificial Sequence
<220> FEATURE:
<223> OTHER INFORMATION: Amplicon of WT Zea Mays

<400> SEQUENCE: 32
gaattcgagc tcggtacccg gggtatccgt cgtttcccat ctcttcctcc tttagtagct    60
accactatat aaatcagggc tcattttctc gctcctcaca ggctcatctc gctttggatc   120
gattggtttc gtaactggtg agggactgag ggtctcggag tgggtc                  166

<210> SEQ ID NO 33
<211> LENGTH: 216
<212> TYPE: DNA
<213> ORGANISM: Artificial Sequence
<220> FEATURE:
<223> OTHER INFORMATION: Amplicon of WT Glycine max

<400> SEQUENCE: 33
gaattgcgcc cttcattacc tatgatgcct ccaccaacct cttgtgttgc ttctttggtt    60
```

-continued

```
catccttcgc agagaagcag ctatatcctc tccggatgtg gtcgatttga agacttctct    120
tcccgagttg gggggttgag gatagggggtt ctcgtgcgtg ccacgtggga ctcgacatag    180
cctggggaat cgcatgacgt gcttaagggc gaattc                              216
```

<210> SEQ ID NO 34
<211> LENGTH: 179
<212> TYPE: DNA
<213> ORGANISM: Artificial Sequence
<220> FEATURE:
<223> OTHER INFORMATION: Amplicon of BT 11 Zea mays, amplified using
      primers from 35S promoter of Cauliflower Mosaic Virus

<400> SEQUENCE: 34

```
gctcgaattc gcccttgaca gtggtcccaa agatggaccc ccacccacga ggaacatcgt     60
ggaagaagaa gacgttccaa ccacgtcttc aaagcaagtg gattgatgtg atatctccac    120
tgacgtaagg gatgacgcac aatcccacta tccttcgcaa gacaagggcg aattcgtaa    179
```

<210> SEQ ID NO 35
<211> LENGTH: 100
<212> TYPE: DNA
<213> ORGANISM: Artificial Sequence
<220> FEATURE:
<223> OTHER INFORMATION: Amplicon of 40-3-2 Glycine max, amplified using
      primers from 3' terminator of the Agrobacterium tumefaciens
      nopaline synthetase gene

<400> SEQUENCE: 35

```
gctcgaattc gcccttatc ctaggttgcg cgctatattt tgttttctat cgcgtattaa     60
atgtataatt gcgggactct aatcaagggc gaattcgtaa                         100
```

<210> SEQ ID NO 36
<211> LENGTH: 98
<212> TYPE: DNA
<213> ORGANISM: Artificial Sequence
<220> FEATURE:
<223> OTHER INFORMATION: Amplicon of MON 810 Zea Mays, amplified using
      primers from Cry1Ab of Bacillus thuringiensis

<400> SEQUENCE: 36

```
gctcgaattc gcccttacgc cttcctggtg caaatcgagc agctcatcaa ccagaggatc     60
gaggagttcg ccaggaacca ggaagggcga attcgtaa                            98
```

<210> SEQ ID NO 37
<211> LENGTH: 105
<212> TYPE: DNA
<213> ORGANISM: Artificial Sequence
<220> FEATURE:
<223> OTHER INFORMATION: Amplicon of Bt176 Zea Mays, amplified using
      primers from Cry1Ab of Bacillus thuringiensis

<400> SEQUENCE: 37

```
gctcgaattc gcccttaccg gttacactcc catcgacatc tccctctccc tcacgcagtt     60
cctgctcagc gagttcgtgc caggtgctga agggcgaatt cgtaa                    105
```

<210> SEQ ID NO 38
<211> LENGTH: 105
<212> TYPE: DNA
<213> ORGANISM: Artificial Sequence
<220> FEATURE:
<223> OTHER INFORMATION: Amplicon of Bt11 Zea Mays, amplified using
      primers from Cry1Ab of Bacillus thuringiensis

<400> SEQUENCE: 38

```
gctcgaattc gcccttcagc acctggcacg aactcgctga gcagaaactg tgtcaaggac    60
aaggagatgt cgatgggagt gtaaccggta agggcgaatt cgtaa                   105
```

<210> SEQ ID NO 39
<211> LENGTH: 101
<212> TYPE: DNA
<213> ORGANISM: Artificial Sequence
<220> FEATURE:
<223> OTHER INFORMATION: Amplicon of BT176 Zea Mays, amplified using
      primers from phosphinothricin acetyltransferase (PAT) gene bar of
      Streptomyces hygroscopicus

<400> SEQUENCE: 39

```
gctcgaattc gcccttcgtc aaccactaca tcgagacaag cacggtcaac ttccgtaccg    60
agccgcagga accgcaggag tggacaaggg cgaattcgta a                       101
```

<210> SEQ ID NO 40
<211> LENGTH: 140
<212> TYPE: DNA
<213> ORGANISM: Artificial Sequence
<220> FEATURE:
<223> OTHER INFORMATION: Amplicon of BT11 Zea Mays, amplified using
      primers from phosphinothricin acetyltransferase (PAT) gene pat of
      Streptomyces viridochromogenes

<400> SEQUENCE: 40

```
gctcgaattc gcccttccgc ggtttgtgat atcgttaacc attacattga gacgtctaca    60
gtgaacttta ggacagagcc acaaacacca caagagtgga ttgatgatct agagaggttg   120
caagaagggc gaattcgtaa                                               140
```

<210> SEQ ID NO 41
<211> LENGTH: 127
<212> TYPE: DNA
<213> ORGANISM: Artificial Sequence
<220> FEATURE:
<223> OTHER INFORMATION: Amplicon of BT11 Zea Mays, amplified using
      primers from generic plant (Rbcl)

<400> SEQUENCE: 41

```
gctcgaattc gcccttaggt ctaaggggta agctacataa cagatatatt gatctgggtc    60
cccaggaacg ggctcgatgt gatagcatcg tcctttgtaa cgatcaaggc taagggcgaa   120
ttcgtaa                                                             127
```

<210> SEQ ID NO 42
<211> LENGTH: 127
<212> TYPE: DNA
<213> ORGANISM: Artificial Sequence
<220> FEATURE:
<223> OTHER INFORMATION: Amplicon of OSR wt, amplified using primers
      from generic plant (Rbcl)

<400> SEQUENCE: 42

```
gctcgaattc gcccttaggt ctaaggggta agctacatac gcaataaatt gagtttcttc    60
tcctggaacg ggctcgatgt ggtagcatcg tcctttgtaa cgatcaaggc taagggcgaa   120
ttcgtaa                                                             127
```

<210> SEQ ID NO 43
<211> LENGTH: 205
<212> TYPE: DNA
<213> ORGANISM: Artificial Sequence
<220> FEATURE:
<223> OTHER INFORMATION: Amplicon of BT11 Zea Mays, amplified using
      primers from 3' terminator of the Agrobacterium tumefaciens nopaline synthetase gene

<400> SEQUENCE: 43

| gctcgaattc gcccgttaaa tgtataattg cgggactcta atcataaaaa cccatctcat | 60 |
| aaataacgtc atgcattaca tgttaattat tacatgctta acgtaattca acagaaatta | 120 |
| tatgataatc atcgcaagac cggcaacagg attcaatctt aagaaacttt attgccaaat | 180 |
| gtttgaacga agggcgaatt cgtaa | 205 |

<210> SEQ ID NO 44
<211> LENGTH: 228
<212> TYPE: DNA
<213> ORGANISM: Artificial Sequence
<220> FEATURE:
<223> OTHER INFORMATION: Amplicon of Brassica napus

<400> SEQUENCE: 44

| gctcgaattc gcccttggcg cagcatcggc tcttctgcat agtaccgttt ctccatcgac | 60 |
| caatggaacg aatgtctaat aggtgttcgt ccttcatctc gctcgattat acagctcacc | 120 |
| acacccacac ctgcggaaca caggctcgaa ctaacttctt cctctttgag aattttctcc | 180 |
| actctttctt gagcttggtc ctcctcattc tcaagggcga attcgtaa | 228 |

<210> SEQ ID NO 45
<211> LENGTH: 123
<212> TYPE: DNA
<213> ORGANISM: Artificial Sequence
<220> FEATURE:
<223> OTHER INFORMATION: Amplicon of 40-3-2 Zea mays, amplified using
    primers from CP4-EPSP

<400> SEQUENCE: 45

| ctcgaattcg cccttgaatg cggacggttc cggaaaggcc agaggatttg cgggcggttg | 60 |
| cgggccggct gcttgcaccg tgaagcatgc aggctgtagc cactgataag ggcgaattcg | 120 |
| taa | 123 |

<210> SEQ ID NO 46
<211> LENGTH: 156
<212> TYPE: DNA
<213> ORGANISM: Artificial Sequence
<220> FEATURE:
<223> OTHER INFORMATION: Amplicon of NK603 Zea mays, amplified using
    primers from CP4-EPSP

<400> SEQUENCE: 46

| gctcgaattc gcccttggct ctgagcttcg tcctcctaag gtcatgtctt ctgtttccac | 60 |
| ggcgtgcatg cttcacggtg caagcagccg gcccgcaacc gcccgcaaat cctctggcct | 120 |
| ttccggaacc gtccgcattc aagggcgaat tcgtaa | 156 |

<210> SEQ ID NO 47
<211> LENGTH: 18
<212> TYPE: DNA
<213> ORGANISM: Artificial Sequence
<220> FEATURE:
<223> OTHER INFORMATION: primer: Cry1Ab of Bacillus thuringiensis

<400> SEQUENCE: 47

| acgccttcct ggtgcaaa | 18 |

<210> SEQ ID NO 48
<211> LENGTH: 19
<212> TYPE: DNA

```
<213> ORGANISM: Artificial Sequence
<220> FEATURE:
<223> OTHER INFORMATION: primer: Cry1Ab of Bacillus thuringiensis

<400

```
<212> TYPE: DNA
<213> ORGANISM: Artificial Sequence
<220> FEATURE:
<223> OTHER INFORMATION: Amplicon of GT73 Brassica napus, amplified
      using primers from CP4-EPSP

<400> SEQUENCE: 54
gctcgaattc gcccttggac ctgtgggaga tagacttgtc acctggaata cggacggttc    60
cagaaagacc agaggactta cgagcagttg ctggacggct gcttgcaccg tgaagcatgc   120
aagggcgaat tcgtaa                                                   136

<210> SEQ ID NO 55
<211> LENGTH: 117
<212> TYPE: DNA
<213> ORGANISM: Artificial Sequence
<220> FEATURE:
<223> OTHER INFORMATION: Amplicon of GT73 Brassica napus, amplified
      using primers from cruciferin

<400> SEQUENCE: 55
gctcgaattc gcccttcagc tcaacagttt ccaaacgagt gccaactaga ccagctcaat    60
gcgctggagc cgtcacacgt acttaaggct gaggctggtc gaagggcgaa ttcgtaa     117

<210> SEQ ID NO 56
<211> LENGTH: 27
<212> TYPE: DNA
<213> ORGANISM: Artificial Sequence
<220> FEATURE:
<223> OTHER INFORMATION: primer: Zea Mays (adh-1)

<400> SEQUENCE: 56
tctcttcctc ctttagagct accacta                                        27

<210> SEQ ID NO 57
<211> LENGTH: 21
<212> TYPE: DNA
<213> ORGANISM: Artificial Sequence
<220> FEATURE:
<223> OTHER INFORMATION: primer: Zea Mays (adh-1)

<400> SEQUENCE: 57
aatcgatcca aagcgagatg a                                              21

<210> SEQ ID NO 58
<211> LENGTH: 18
<212> TYPE: DNA
<213> ORGANISM: Artificial Sequence
<220> FEATURE:
<223> OTHER INFORMATION: primer: Glycine max (lectin)

<400> SEQUENCE: 58
aaccggtagc gttgccag                                                  18

<210> SEQ ID NO 59
<211> LENGTH: 19
<212> TYPE: DNA
<213> ORGANISM: Artificial Sequence
<220> FEATURE:
<223> OTHER INFORMATION: primer: Glycine max (lectin)

<400> SEQUENCE: 59
agcccatctg caagccttt                                                 19

<210> SEQ ID NO 60
<211> LENGTH: 23
```

```
<212> TYPE: DNA
<213> ORGANISM: Artificial Sequence
<220> FEATURE:
<223> OTHER INFORMATION: primer: 35S promoter of Cauliflower Mosaic
      Virus

<400> SEQUENCE: 60
aaagcaagtg gattgatgtg ata                                            23

<210> SEQ ID NO 61
<211> LENGTH: 20
<212> TYPE: DNA
<213> ORGANISM: Artificial Sequence
<220> FEATURE:
<223> OTHER INFORMATION: primer: 35S promoter of Cauliflower Mosaic
      Virus

<400> SEQUENCE: 61
gggtcttgcg aaggatagtg                                                20

<210> SEQ ID NO 62
<211> LENGTH: 19
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 62
tgaaggaccg gtgggagat                                                 19

<210> SEQ ID NO 63
<211> LENGTH: 19
<212> TYPE: DNA
<213> ORGANISM: Artificial Sequence
<220> FEATURE:
<223> OTHER INFORMATION: primer: 5-Enol-pyruvylshikimate-3-phosphate
      synthase EPSPS gene from Agrobacterium sp. CP4

<400> SEQUENCE: 63
tgaaggacct gtgggagat                                                 19

<210> SEQ ID NO 64
<211> LENGTH: 24
<212> TYPE: DNA
<213> ORGANISM: Artificial Sequence
<220> FEATURE:
<223> OTHER INFORMATION: primer: Beta vulgaris (GluA3)

<400> SEQUENCE: 64
gacctccata ttactgaaag gaag                                           24

<210> SEQ ID NO 65
<211> LENGTH: 23
<212> TYPE: DNA
<213> ORGANISM: Artificial Sequence
<220> FEATURE:
<223> OTHER INFORMATION: primer: Beta vulgaris (GluA3)

<400> SEQUENCE: 65
gagtaattgc tccatcctgt tca                                            23

<210> SEQ ID NO 66
<211> LENGTH: 28
<212> TYPE: DNA
<213> ORGANISM: Artificial Sequence
<220> FEATURE:
<223> OTHER INFORMATION: primer: Gossypium
```

-continued

```
<400> SEQUENCE: 66
agtttgtagg ttttgatgtt acattgag                                              28

<210> SEQ ID NO 67
<211> LENGTH: 21
<212> TYPE: DNA
<213> ORGANISM: Artificial Sequence
<220> FEATURE:
<223> OTHER INFORMATION: primer: Gossypium

<400> SEQUENCE: 67
gcatctttga accgcctact g                                                     21

<210> SEQ ID NO 68
<211> LENGTH: 21
<212> TYPE: DNA
<213> ORGANISM: Artificial Sequence
<220> FEATURE:
<223> OTHER INFORMATION: primer: Solanum tuberosum (UGPase)

<400> SEQUENCE: 68
ggacatgtga agagacggag c                                                     21

<210> SEQ ID NO 69
<211> LENGTH: 19
<212> TYPE: DNA
<213> ORGANISM: Artificial Sequence
<220> FEATURE:
<223> OTHER INFORMATION: primer: Solanum tuberosum (UGPase)

<400> SEQUENCE: 69
cctacctcta cccctccgc                                                        19

<210> SEQ ID NO 70
<211> LENGTH: 108
<212> TYPE: DNA
<213> ORGANISM: Artificial Sequence
<220> FEATURE:
<223> OTHER INFORMATION: Amplicon of WT Zea Mays

<400> SEQUENCE: 70
gaattcgccc ttaatcgatc caaagcgaga tgagcctgtg aggagcgaga aaatgagccc          60
tgatttatat agtggtagct ctaaaggagg aagagaaagg gcgaattc                      108

<210> SEQ ID NO 71
<211> LENGTH: 105
<212> TYPE: DNA
<213> ORGANISM: Artificial Sequence
<220> FEATURE:
<223> OTHER INFORMATION: Amplicon of WT Glycine max

<400> SEQUENCE: 71
gaattcgccc ttaaccggta gcgttgccag cttcgccgct tccttcaact tcaccttcta          60
tgcccctgac acaaaaaggc ttgcagatgg gctaagggcg aattc                         105

<210> SEQ ID NO 72
<211> LENGTH: 99
<212> TYPE: DNA
<213> ORGANISM: Artificial Sequence
<220> FEATURE:
<223> OTHER INFORMATION: Amplicon, amplified using primers from 35S
      promoter of Cauliflower Mosaic Virus

<400> SEQUENCE: 72
```

```
gaattcgccc ttgggtcttg cgaaggatag tgggattgtg cgtcatccct tacgtcagtg    60
gagatatcac atcaatccac ttgctttaag ggcgaattc                           99

<210> SEQ ID NO 73
<211> LENGTH: 97
<212> TYPE: DNA
<213> ORGANISM: Artificial Sequence
<220> FEATURE:
<223> OTHER INFORMATION: Amplicon of MON810 Zea Mays, amplified using
      primers from Cry1Ab of Bacillus thuringiensis

<400> SEQUENCE: 73
gaattcgccc ttcagcacct ggcacgaact cgctgagcag gaactgcgtg agggagaggg    60
agatgtcgat gggagtgtaa ccggtaaggg cgaattc                             97

<210> SEQ ID NO 74
<211> LENGTH: 132
<212> TYPE: DNA
<213> ORGANISM: Artificial Sequence
<220> FEATURE:
<223> OTHER INFORMATION: Amplicon of GT73 Zea mays, amplified using
      primers from CP4-EPSP

<400> SEQUENCE: 74
gaattcgccc tttgaaggac ctgtgggaga tagacttgtc acctggaata cggacggttc    60
cagaaagacc agaggactta cgagcagttg ctggacggct gcttgcaccg tgaagcatgc   120
aagggcgaat tc                                                       132

<210> SEQ ID NO 75
<211> LENGTH: 132
<212> TYPE: DNA
<213> ORGANISM: Artificial Sequence
<220> FEATURE:
<223> OTHER INFORMATION: Amplicon of Roundup-Ready Soy, amplified using
      primers from CP4-EPSP

<400> SEQUENCE: 75
gaattcgccc tttgaaggac cggtgggaga tcgacttgtc gccgggaatg cggacggttc    60
cggaaaggcc agaggatttg cgggcggttg cgggccggct gcttgcaccg tgaagcatgc   120
aagggcgaat tc                                                       132

<210> SEQ ID NO 76
<211> LENGTH: 142
<212> TYPE: DNA
<213> ORGANISM: Artificial Sequence
<220> FEATURE:
<223> OTHER INFORMATION: Amplicon of Beta vulgaris, amplified using
      primers from GluA3

<400> SEQUENCE: 76
gaattcgccc ttgacctcca tattactgaa aggaagccaa aagggatcaa ttaagtgctc    60
tacgaagttt aaagtatgtg ccgctctcaa gactgaacat ggcactgtga acaggatgga   120
gcaattactc aagggcgaat tc                                            142

<210> SEQ ID NO 77
<211> LENGTH: 139
<212> TYPE: DNA
<213> ORGANISM: Artificial Sequence
<220> FEATURE:
<223> OTHER INFORMATION: Amplicon of Gossypium amplified using primers
      from Sah-7

<400> SEQUENCE: 77
```

```
gaattcgccc ttagtttgta ggttttgatg ttacattgag tgacagtgaa tgaaagggtg      60
tgtaaacata aaataatggg aacaaccatg acatgttgga ctggatcagt aggcggttca     120
aagatgcaag ggcgaattc                                                  139
```

<210> SEQ ID NO 78
<211> LENGTH: 111
<212> TYPE: DNA
<213> ORGANISM: Artificial Sequence
<220> FEATURE:
<223> OTHER INFORMATION: Amplicon of Solanum Tuberosum, amplified using primers from UGPase

<400> SEQUENCE: 78

```
gaattcgccc ttggacatgt gaagagacgg agcgcagatt ccccagtaag gaggtgtgag      60
gggctagttg tagagggtac gcggaggggt agaggtagga agggcgaatt c              111
```

<210> SEQ ID NO 79
<211> LENGTH: 22
<212> TYPE: DNA
<213> ORGANISM: Artificial Sequence
<220> FEATURE:
<223> OTHER INFORMATION: primer: Brassica napus (ACC)

<400> SEQUENCE: 79

```
ggtgagctgt ataatcgagc ga                                               22
```

TRANSGENIC PLANT EVENT DETECTION

CROSS-REFERENCE TO RELATED APPLICATIONS

This application is a U.S. national stage entry under 35 U.S.C. §371 of PCT International Patent Application No. PCT/EP2008/051059, filed Jan. 29, 2008, which claims priority to European Patent Application No. 07447008.9, filed Jan. 29, 2007 and European Patent Application No. 07108343.0, filed May 16, 2007, the contents of which are incorporated herein by reference in their entirety.

FIELD OF THE INVENTION

The present invention relates to detection of materials derived from transgenic plant events. In particular, the invention provides methods, reagents, kits and reference materials for detecting the presence or absence in a sample of genetic material derived from and attributable to select transgenic plant events.

BACKGROUND OF THE INVENTION

Genetically modified organisms (GMOs), in particular genetically modified plants, are gaining importance in agriculture as well as in the production and marketing of foods and feed.

However, due to existing concerns regarding the impact of GMOs on the environment and on consumers' health, the introduction of new GMOs commonly requires regulatory approval and, in many countries including the European Union, food and feed products containing or produced from GMOs are themselves subjected to authorisation and compulsory labelling (see, e.g., Regulation (EC) no. 1829/2003. Off J Eur Communities: Legis. 2003, L268: 1-23; Regulation (EC) no. 1830/2003. Off J Eur Communities: Legis. 2003, L268: 24-28).

Consequently, tracing of GMOs in the environment and through the cultivation process and the food or feed production chain is fundamental for environmental risk assessment, as well as necessary to preserve consumers' confidence and to satisfy or verify the observance of mandatory regulations, including GMO product labelling.

This requires the availability of methods that can determine the presence, identity and/or quantity of GMOs or materials originating or derived therefrom in, for example, food and feed sources, ingredients and/or processed consumables. DNA-based methods are very useful in this respect, not least because DNA often withstands physical and chemical food processing treatments better than other molecules, such as proteins. For example, real-time polymerase chain reaction (PCR) proved to be a specific and sensitive technique for the quantification of nucleic acids indicative of the presence of DNA originating from GMOs.

Assays are available to unambiguously conclude the presence or absence of genetic material derived from a select plant transformation event in a sample. Commonly, such assays can detect the presence of a unique, event-specific nucleotide sequence found in the plant transformation event of interest but absent from other events. For example, such distinctive nucleotide sequences may be present at junctions between the GMO's endogenous genomic sequence and the sequence of the transforming gene construct at the genomic insertion site of the latter; detection may for instance involve PCR amplification across the said junction using specific primers flanking the junction (see, e.g., Hernandez et al. 2003. Transgenic Res 12: 179-189; Hernandez et al. 2004. J Cereal Sci 39: 99-107; Berdal et al. 2001. Eur Food Res Technol 213: 432-438; Nielsen et al. 2004. Eur Food Res Technol 219: 421-427; or Ronning et al. 2003. Eur Food Res Technol 216: 347-354).

However, these event-specific assays can often be procured only as highly priced kits allowing for a limited number of tests, are confined to detection of material from a single event, and commonly employ very particular reaction conditions. Yet, the number of generated, authorised and marketed and GMOs keeps increasing. Hence, an unambiguous determination of the GMO composition of a sample would in principle require to apply an ever-growing battery of separate event-specific detection assays on each sample, which is both laborious and cost demanding.

Therefore, while it continues to be desirable to employ event-specific assays due to the unambiguous nature of their output, there exists a need for using these assays in a more effective and targeted manner, such as to improve the detection of GMOs detection, e.g., in terms of time expense, cost and labour intensity.

SUMMARY OF THE INVENTION

In aspects, the present invention provides methods, reagents, kits and reference materials that address one or more of the above discussed needs of the art.

In general, the invention hence provides improved methods, reagents, kits and reference materials for detecting material derived from GMOs, and preferably from genetically modified plants, in samples.

More particularly, the inventors realised that by carefully choosing certain sequence features to be assayed in the sample—wherein the said sequence features need not be event-specific and may in fact be shared between two or more events—one can conclude whether the sample potentially contains material derived from one or more transformation events or, conversely, whether the sample does not contain material derived from one or more such transformation events. The assays of the invention can thus provide a valuable indication of the potential GMOs contents of the sample and thereby advantageously reduce the number of subsequent tests (such as, e.g., event-specific assays), needed to verify the presence of material derived from one or more particular transformation events in the sample; this can in turn improve the cost-, time- and/or labour-effectiveness of GMOs detection methods. For example, the assays of the invention may allow to considerably reduce the number of event-specific assays needed to characterise the GMOs composition of the sample.

The inventors also meticulously assessed the known, commercially significant and/or authorised transformation events to select sequence features for being assayed in a sample, such as to reduce the number of individual test reactions needed per sample yet ensuring adequate informativeness of the GMO profiling according to the invention.

The present invention integrates the above relevant realisation in its diverse aspects.

Hence, in a particularly preferred aspect (herein aspect "A1") the invention concerns a method to examine a sample for the presence or absence of material derived from one or more transgenic plant events comprising the steps of:
(1) detecting the presence or absence in the sample of nucleic acids comprising or consisting of:
   a) "Zm": a nucleic acid derived from and specific for *Zea mays* taxon, preferably *Zea mays* ssp. *mays*,
   b) "Bn": a nucleic acid derived from and specific for *Brassica napus* taxon, c) "Gm": a nucleic acid derived from and specific for *Glycine max* taxon, and one, more than one or all of nucleic acids chosen from:
d) "p35S": a nucleic acid derived from the 3' promoter of Cauliflower Mosaic Virus,
e) "tNOS": a nucleic acid derived from the 3' terminator of the *Agrobacterium tumefaciens* nopaline synthetase gene,
f) "Cry1Ab": a nucleic acid derived from the crystal protein gene Cry1Ab of *Bacillus thuringiensis*,
g) "PAT/bar": a nucleic acid derived from the phosphinothricin acetyltransferase (PAT) gene bar of *Streptomyces hygroscopicus*,
h) "PAT/pat": a nucleic acid derived from the phosphinothricin acetyltransferase (PAT) gene pat of *Streptomyces viridochromogenes*, and
i) "CP4-EPSPS": a nucleic acid derived from the 5-Enolpyruvylshikimate-3-phosphate synthase EPSPS gene from *Agrobacterium* sp. CP4; and (2) concluding the presence or absence in the sample of material derived from one or more transgenic plant events, such as events chosen from the group comprising or consisting of: events Bt176, Bt11, Bt10, MON810, MON863, TC1507, NK603, T25, GA21, DAS-59122, crosses thereof, and related events thereof; events Topas 19/2, MS1, RF1, RF2, RF3, MS8, GT73, T45, Liberator pHoe6/Ac, GS40/90pHoe6/Ac, crosses thereof including MS1/RF1, MS1/RF2, MS8/RF3, and related events thereof; events MON 40-3-2, MON89788, A2704-12, A5547-127, crosses thereof, and related events thereof.

Aspect A1 allows to investigate the potential presence or absence in a sample of material from numerous transgenic plant events belonging to several distinct plant taxons, while performing a relatively limited number of detection steps. Advantageously, the transgenic plant events detected by the method of aspect A1 encompass a large fraction, or even substantially most, transgenic plant events presently authorised and/or commercialised, e.g., in Europe, i.e., transgenic plant events which are particularly likely to be encountered in, e.g., environmental or commercial samples. Hence, in this aspect the invention provides a relatively undemanding assay for inspecting a considerable spectrum of relevant transgenic plant events.

Preferably, step (1) of aspect A1 can involve detecting the presence or absence in the sample of nucleic acids comprising or consisting of all nucleic acid listed under a)-i) as defined above. This advantageously improves the information obtained by testing the sample and permits to conclude the potential presence or absence of material derived from a substantially high number of transgenic plant events.

Whereas in step (2) of aspect A1 detection is particularly foreseen for particular existing transgenic plant events, it shall be appreciated that other events, including any future transgenic events to be generated, can also be detected insofar they belong to the taxons as defined under a)-c) and comprise one or more of the nucleic acids as defined under d)-i). This observation applies mutatis mutandis to detection of events in any aspects of the invention as described in the following.

While the method of aspect A1 permits to simultaneously examine the presence or absence in the sample of transgenic plant events belonging to at least three different taxons, the inventors also envisage adapting the method to individual taxons. This may usefully reduce the number of nucleic acid detection steps if information is only required for a particular taxon. Accordingly, in a further aspect ("A2") the invention provides a method to examine a sample for the presence or absence of material derived from one or more maize transgenic plant events comprising the steps of:
(1) detecting the presence or absence in the sample of nucleic acids comprising or consisting of nucleic acid listed under a) as defined above and one, more than one or all of nucleic acids chosen from those listed under d)-i) as defined above; and
(2) concluding the presence or absence in the sample of material derived from one or more maize transgenic plant events, such as events chosen from the group comprising or consisting of events Bt176, Bt11, Bt10, MON810, MON863, TC1507, NK603, T25, GA21, DAS-59122, crosses thereof, and related events thereof.

Preferably, step (1) of aspect A2 can involve detecting the presence or absence in the sample of nucleic acids comprising or consisting of all nucleic acid listed under a) and d)-i) as defined above. This increases the information obtained by testing the sample and permits to conclude the potential presence or absence of material derived from a comparably higher number of maize transgenic plant events.

In a further aspect ("A3") the invention offers a method to examine a sample for the presence or absence of material derived from one or more oilseed rape transgenic plant events comprising the steps of:
(1) detecting the presence or absence in the sample of nucleic acids comprising or consisting of nucleic acid listed under b) as defined above and one, more than one or all of nucleic acids chosen from those listed under d)-i) as defined above; and
(2) concluding the presence or absence in the sample of material derived from one or more oilseed rape transgenic plant events, such as events chosen from the group comprising or consisting of events Topas 19/2, MS1, RF1, RF2, RF3, MS8, GT73, T45, Liberator pHoe6/Ac, GS40/90pHoe6/Ac, crosses thereof including MS1/RF1, MS1/RF2, MS8/RF3 and related events thereof.

Preferably, step (1) of aspect A3 can involve detecting the presence or absence in the sample of nucleic acids comprising or consisting of all nucleic acids listed under b) and d)-i) as defined above. This increases the information obtained by testing the sample and permits to conclude the potential presence or absence of material derived from a comparably higher number of oilseed rape transgenic plant events.

In another preferred embodiment, step (1) of aspect A3 involves detecting the presence or absence in the sample of nucleic acids comprising or consisting of nucleic acid listed under b) and d), e), and g)-i) as defined above. It is noted that many oilseed rape events, e.g., those specifically recited in step (2) of aspect A3, may not include nucleic acid listed under f) as defined above. Therefore, omission of the said nucleic acid listed under f) from step (1) of aspect A3 may reduce the number of tests without loss of information.

In a further aspect ("A4") the invention offers a method to examine a sample for the presence or absence of material derived from one or more soybean transgenic plant events comprising the steps of:
(1) detecting the presence or absence in the sample of nucleic acids comprising or consisting of nucleic acid listed under c) as defined above and one, more than one or all of nucleic acids chosen from those listed under d)-i) as defined above; and
(2) concluding the presence or absence in the sample of material derived from one or more soybean transgenic plant events, such as events chosen from the group comprising or consisting of events MON 40-3-2, MON89788, A2704-12, A5547-127, crosses thereof, and related events thereof.

Preferably, step (1) of aspect A4 can involve detecting the presence or absence in the sample of nucleic acids comprising or consisting of all nucleic acids listed under c) and d)-i) as defined above. This increases the information obtained by testing the sample and permits to conclude the potential presence or absence of material derived from a comparably higher number of soybean transgenic plant events.

In another preferred embodiment, step (1) of aspect A4 involves detecting the presence or absence in the sample of nucleic acids comprising or consisting of nucleic acid listed under c) and d), e), h) and i) as defined above. It is noted that many soybean events, e.g., those specifically recited in step (2) of aspect A4, may not include nucleic acids listed under f) and g) as defined above. Therefore, omission of the said nucleic acids listed under f) and g) from step (1) of aspect A4 may reduce the number of tests without loss of information.

It shall be also appreciated that further aspects can teach combinations of any two of the above aspects A2-A4. For example, this may advantageously reduce the number of testing actions in cases where detection of transgenic events from select taxons is intended.

Accordingly, in a further aspect ("A5") the invention offers a method to examine a sample for the presence or absence of material derived from one or more maize and/or oilseed rape transgenic plant events comprising the steps of:
(1) detecting the presence or absence in the sample of nucleic acids comprising or consisting of nucleic acids listed under a) and b) as defined above and one, more than one or all of nucleic acids chosen from those listed under d)-i) as defined above; and
(2) concluding the presence or absence in the sample of material derived from one or more maize and/or oilseed rape transgenic plant events, such as events chosen from the group comprising or consisting of events Bt176, Bt11, Bt10, MON810, MON863, TC1507, NK603, T25, GA21, DAS-59122, crosses thereof, and related events thereof; and events Topas 19/2, MS1, RF1, RF2, RF3, MS8, GT73, T45, Liberator pHoe6/Ac, GS40/90pHoe6/Ac, crosses thereof including MS1/RF1, MS1/RF2, MS8/RF3 and related events thereof.

For reasons clarified above, step (1) of aspect A5 can preferably involve detecting the presence or absence in the sample of nucleic acids comprising or consisting of all nucleic acids listed under a), b) and d)-i) as defined above.

In yet a further aspect ("A6") the invention offers a method to examine a sample for the presence or absence of material derived from one or more maize and/or soybean transgenic plant events comprising the steps of:
(1) detecting the presence or absence in the sample of nucleic acids comprising or consisting of nucleic acids listed under a) and c) as defined above and one, more than one or all of nucleic acids chosen from those listed under d)-i) as defined above; and
(2) concluding the presence or absence in the sample of material derived from one or more maize and/or soybean transgenic plant events, such as events chosen from the group comprising or consisting of events Bt176, Bt11, Bt10, MON810, MON863, TC1507, NK603, T25, GA21, DAS-59122, crosses thereof, and related events thereof; and events MON 40-3-2, MON89788, A2704-12, A5547-127, crosses thereof, and related events thereof.

For reasons clarified above, step (1) of aspect A6 can preferably involve detecting the presence or absence in the sample of nucleic acids comprising or consisting of all nucleic acids listed under a), c) and d)-i) as defined above.

In yet a further aspect ("A7") the invention offers a method to examine a sample for the presence or absence of material derived from one or more oilseed rape and/or soybean transgenic plant events comprising the steps of:
(1) detecting the presence or absence in the sample of nucleic acids comprising or consisting of nucleic acids listed under b) and c) as defined above and one, more than one or all of nucleic acids chosen from those listed under d)-i) as defined above; and
(2) concluding the presence or absence in the sample of material derived from one or more oilseed rape and/or soybean transgenic plant events, such as events chosen from the group comprising or consisting of events Topas 19/2, MS1, RF1, RF2, RF3, MS8, GT73, T45, Liberator pHoe6/Ac, GS40/90pHoe6/Ac, crosses thereof including MS1/RF1, MS1/RF2, MS8/RF3 and related events thereof; and events MON 40-3-2, MON89788, A2704-12, A5547-127, crosses thereof, and related events thereof.

For reasons clarified above, step (1) of aspect A7 can preferably involve detecting the presence or absence in the sample of nucleic acids comprising or consisting of all nucleic acids listed under b), c) and d)-i) as defined above.

In another preferred embodiment, step (1) of aspect A7 involves detecting the presence or absence in the sample of nucleic acids comprising or consisting of all nucleic acids listed under b), c) and d), e) and g)-i) as defined above, i.e., without detecting the nucleic acid listed under f).

Hence, in an aspect ("A8") the invention offers a method to examine a sample for the presence or absence of material derived from one or more maize and/or oilseed rape and/or soybean transgenic plant events comprising the steps of:
(1) detecting the presence or absence in the sample of nucleic acids comprising or consisting of:
  one, more than one or all of nucleic acids chosen from those listed under a), b) and c) as defined above, and
  one, more than one or all of nucleic acids chosen from those listed under d)-i) as defined above; and
(2) concluding the presence or absence in the sample of material derived from one or more transgenic plant events, such as events chosen from the group comprising or consisting of: events Bt176, Bt11, Bt10, MON810, MON863, TC1507, NK603, T25, GA21, DAS-59122, crosses thereof, and related events thereof; events Topas 19/2, MS1, RF1, RF2, RF3, MS8, GT73, T45, Liberator pHoe6/Ac, GS40/90pHoe6/Ac, crosses thereof including MS1/RF1, MS1/RF2, MS8/RF3, and related events thereof; and events MON 40-3-2, MON89788, A2704-12, A5547-127, crosses thereof, and related events thereof.

For reasons clarified above, step (1) of aspect A8 can preferably involve detecting the presence or absence in the sample of nucleic acids comprising all nucleic acids listed under d)-i) as defined above.

As explained, methods of the above aspects A1-A8 are well-suited for detecting the potential presence or absence in a sample of material derived from relevant transgenic plant events, such as ones that have been authorised and/or are commonly used. However, it shall be appreciated that the said methods are also advantageously flexible and, in embodiments, allow for better assessing the presence or absence of material derived from further transgenic events, such as events not specifically recited in step (2) of the above aspects A1-A8. This thus permits to gather even more information about the composition of the sample.

Hence, in embodiments, step (1) of any of the above aspects A1, A2, A5, A6 or A8 may further comprise detecting the presence or absence in the sample of nucleic acid j) "mCry3A": a nucleic acid derived from the modified crystal protein gene Cry3A of *Bacillus thuringiensis*; and the group of events as defined in step (2) of any of the respective aspects further comprises maize event MIR604, crosses thereof with other maize events, and events related to MIR604.

In further embodiments, step (1) of any of the above aspects A1, A2, A5, A6 or A8 may further comprise detecting the presence or absence in the sample of one or both nucleic acids k) "cordapA": a nucleic acid derived from the lysine-insensitive dihydrodipicolinate synthase (cDHDPS) gene cordapA of *Corynebacterium glutamicum* and/or l) "Glb1": a nucleic acid derived from the Glb1 promoter of maize; and the group of events as defined in step (2) of any of the respective aspects further comprises maize event LY038, crosses thereof with other maize events, and events related to LY038.

In yet further embodiments, step (1) of any of the above aspects A1, A2, A5, A6 or A8 may further comprise detecting the presence or absence in the sample of nucleic acid m) "Cry3Bb1": a nucleic acid derived from the crystal protein gene Cry3Bb1 of *Bacillus thuringiensis*; and the group of events as defined in step (2) of any of the respective aspects further comprises maize event MON88017, crosses thereof with other maize events, and events related to MON88017.

Accordingly, in embodiments, step (1) of any of the above aspects A1, A2, A5, A6 or A8 may further comprise detecting the presence or absence in the sample of one, more than one, or all of nucleic acids listed under j)-m) as defined above; and the group of events as defined in step (2) of any of the respective aspects may further comprise one, more than one, or all of the maize events MIR604, LY038 and MON88017, crosses thereof with other maize events, and events related thereto. However, whereas detection of the respective nucleic acids listed under j)-m) as defined above can provide for improved detection of the presence of material from the maize events MIR604, LY038 and/or MON88017 in the sample, the detection of nucleic acids listed under d)-i) as defined above already allows to draw conclusions concerning the potential presence of material from said events MIR604, LY038 and/or MON88017 in a sample (see also Table 3).

In embodiments, step (1) of any of the above aspects A1, A3, A5, A7 or A8 may further comprise detecting the presence or absence in the sample of nucleic acid n) "Bxn": a nucleic acid derived from the nitrilase gene Bxn of *Klebsiella pneumoniae* ssp. *ozaenae*; and the group of events as defined in step (2) of any of the respective aspects further comprises oilseed rape event OXY235, crosses thereof with other oilseed rape events, and events related to OXY235. However, whereas detection of the nucleic acid listed under n) as defined above can provide for improved detection of the presence of material from the oilseed rape event OXY235 in the sample, the detection of nucleic acids listed under d)-i) as defined above already allows to draw conclusions concerning the potential presence of material from said event OXY235 in a sample (see Table 3).

Thus, in an aspect ("A9") the invention offers a method to examine a sample for the presence or absence of material derived from one or more maize and/or oilseed rape and/or soybean transgenic plant events comprising the steps of:
(1) detecting the presence or absence in the sample of nucleic acids comprising or consisting of:
  one, more than one or all of nucleic acids chosen from those listed under a), b) and c) as defined above, and
  one, more than one or all of nucleic acids chosen from those listed under d)-i) as defined above, and
  optionally, one, more than one or all of nucleic acids chosen from those listed under j)-n) as defined above; and
(2) concluding the presence or absence in the sample of material derived from one or more transgenic plant events, such as events chosen from the group comprising or consisting of: events Bt176, Bt11, Bt10, MON810, MON863, TC1507, NK603, T25, GA21, DAS-59122, MIR604, LY038 and MON88017, crosses thereof, and related events thereof; events Topas 19/2, MS1, RF1, RF2, RF3, MS8, GT73, T45, Liberator pHoe6/Ac, GS40/90pHoe6/Ac, OXY235, crosses thereof including MS1/RF1, MS1/RF2, MS8/RF3, and related events thereof; and events MON 40-3-2, MON89788, A2704-12, A5547-127, crosses thereof, and related events thereof.

For reasons clarified above, step (1) of aspect A9 can preferably involve detecting the presence or absence in the sample of nucleic acids comprising all nucleic acids listed under d)-i) as defined above.

In further advantageous embodiments, the methods of the above aspects A1-A8 can thus additionally also assess the potential presence or absence in samples of material derived from transgenic events that belong to other taxons.

Accordingly, in embodiments, step (1) of any of the above aspects A1-A8 (or of the above embodiments of said aspects) may further comprise detecting the presence or absence in the sample of nucleic acid o) "Or": a nucleic acid derived from and specific for *Oryza sativa* taxon; and the group of events as defined in step (2) of any of the respective aspects further comprises one, more than one, or all of the rice events LL62, LL06 and LL601, crosses thereof, and events related thereto.

In further embodiments, step (1) of any of the above aspects A1-A8 (or of the above embodiments of said aspects) further comprises detecting the presence or absence in the sample of nucleic acid p) "Bv": a nucleic acid derived from and specific for *Beta vulgaris* taxon; and the group of events as defined in step (2) of any of the respective aspects further comprises one, more than one, or all of the sugar beet events T120-7, H7-1 and A5-15, crosses thereof, and events related thereto.

In still further embodiments, step (1) of any of the above aspects A1-A8 (or of the above embodiments of said aspects) further comprises detecting the presence or absence in the sample of nucleic acid q) "Gs": a nucleic acid derived from and specific for *Gossypium* taxon; and the group of events as defined in step (2) of any of the respective aspects further comprises one, more than one, or all of the cotton events LL cotton 25, MON 1445, MON 531, MON15985, crosses thereof, and events related thereto.

In a further development, step (1) of any of the embodiments of the preceding paragraph may further comprise detecting the presence or absence in the sample of one or both of nucleic acids r) "Cry1Ac": a nucleic acid derived from the crystal protein gene Cry1Ac of *Bacillus thuringiensis* and/or s) "Cry2Ab2": a nucleic acid derived from the crystal protein gene Cry2Ab2 of *Bacillus thuringiensis*; and the group of events as defined in step (2) can particularly well detect one or both of cotton events MON 531, MON15985, crosses thereof with other cotton events, and events related thereto.

In still further embodiments, step (1) of any of the above aspects A1-A8 (or of the above embodiments of said aspects) further comprises detecting the presence or absence in the sample of nucleic acid t) "St": a nucleic acid derived from and specific for *Solanum tuberosum* taxon; and the group of events as defined in step (2) of any of the respective aspects further comprises the potato event EH92-527-1 and events related thereto.

In a further development, step (1) of any of the embodiments of the preceding paragraph may further comprise detecting the presence or absence in the sample of nucleic acid u) "GBSS": a nucleic acid derived from the granule bound starch synthase gene Gbss of *Solanum tuberosum*, further improving the reliability of detection of material from said event EH92-527-1.

It shall be appreciated that the preceding methods may be performed in various suitable combinations, allowing desired events to be detected and reducing the effort.

Thus, in an aspect ("A10") the invention offers a method to examine a sample for the presence or absence of material derived from one or more maize and/or oilseed rape and/or soybean and/or rice and/or sugar beet and/or cotton and/or potato transgenic plant events comprising the steps of:
(1) detecting the presence or absence in the sample of nucleic acids comprising or consisting of:
one, more than one or all of nucleic acids chosen from those listed under a), b), c), o), p) q) and t) as defined above, and
one, more than one or all of nucleic acids chosen from those listed under d)-i) as defined above, and
optionally, one more than one or all of nucleic acids chosen from those listed under j)-n), r) s) and u) as defined above, and
(2) concluding the presence or absence in the sample of material derived from one or more transgenic plant events, such as events chosen from the group comprising or consisting of: events Bt176, Bt11, Bt10, MON810, MON863, TC1507, NK603, T25, GA21, DAS-59122, MIR604, LY038, MON88017, crosses thereof, and related events thereof; events Topas 19/2, MS1, RF1, RF2, RF3, MS8, GT73, T45, Liberator pHoe6/Ac, GS40/90pHoe6/Ac, OXY235, crosses thereof including MS1/RF1, MS1/RF2, MS8/RF3, and related events thereof; events MON 40-3-2, MON89788, A2704-12, A5547-127, crosses thereof, and related events thereof; events LL62, LL06 and LL601, crosses thereof, and events related thereof; events T120-7, H7-1 and A5-15, crosses thereof, and events related thereto; events LL cotton 25, MON 1445, MON 531, MON15985, crosses thereof, and events related thereto; and event EH92-527-1 and events related thereto.

For reasons clarified above, step (1) of aspect A10 can preferably involve detecting the presence or absence in the sample of nucleic acids comprising all nucleic acids listed under d)-i) as defined above.

In a related preferred aspect ("A11") the invention offers a method to examine a sample for the presence or absence of material derived from one or more maize and/or oilseed rape and/or soybean and/or rice and/or sugar beet and/or cotton and/or potato transgenic plant events comprising the steps of:
(1) detecting the presence or absence in the sample of nucleic acids comprising or consisting of:
one, more than one or all of nucleic acids chosen from those listed under a), b), c), o), p) q) and t) as defined above, and
one, more than one or all of nucleic acids chosen from those listed under d)-i) as defined above; and
(2) concluding the presence or absence in the sample of material derived from one or more transgenic plant events, such as events chosen from the group comprising or consisting of: events Bt176, Bt11, Bt10, MON810, MON863, TC1507, NK603, T25, GA21, DAS-59122, optionally MIR604, LY038 and MON88017, crosses thereof, and related events thereof; events Topas 19/2, MS1, RF1, RF2, RF3, MS8, GT73, T45, Liberator pHoe6/Ac, GS40/90pHoe6/Ac, optionally OXY235, crosses thereof including MS1/RF1, MS1/RF2, MS8/RF3, and related events thereof; events MON 40-3-2, MON89788, A2704-12, A5547-127, crosses thereof, and related events thereof; events LL62, LL06 and LL601, crosses thereof, and events related thereof; events T120-7, H7-1 and A5-15, crosses thereof, and events related thereto; events LL cotton 25, MON 1445, MON 531, MON15985, crosses thereof, and events related thereto; and event EH92-527-1 and events related thereto.

For reasons clarified above, step (1) of aspect A11 can preferably involve detecting the presence or absence in the sample of nucleic acids comprising all nucleic acids listed under d)-i) as defined above.

Preferably, in any of the methods of the above aspects A1 to A11 or of any embodiment of said aspects, the presence or absence of nucleic acids in a sample is detected using amplification of amplicons comprised in the respective nucleic acids, such as, preferably using PCR and, more preferably using real-time PCR.

To allow for efficient use of PCR amplification in the above methods, the present inventors meticulously searched for and tested primers and primer pairs so as to select ones particularly advantageous in said methods.

The identified preferred primer pairs are listed in Table 1. They entail inter alia the following significant advantages. The primers display substantially same or satisfactorily similar annealing temperature, thus allowing the PCR amplification on the different nucleic acids to be performed at the same temperature cycling conditions and hence in the same apparatus. This greatly facilitates the throughput of the methods and reduces the amount of labour, disposables and apparatus needed. The primer pairs produce amplicons of about 100 bp, and thereby allow to amplify the target nucleic acids even from samples in which the genetic material is largely fragmented, as may be the case for processed food or feed. The primers and primer pairs show adequate specificity of amplification, as well as sensitivity suitable for real-time amplification. In addition, to ensure sensitivity and uniformity of the methods and kits provided by the invention, the primers and primer pairs have been so designed as to generate, at 40 cycles and using 10000 copies of a template, fluorescence of at least 2500 relative fluorescence unit (RFU) and wherein the so-generated fluorescence values for the different primer sets preferably lies within a 3-fold margin. In addition, each primer pair has been so designed as to amplify on the respective nucleic acids from substantially all events of interest, despite the existence of potential sequence disparities (e.g., due to optimised codon usage) in said nucleic acids between such events.

TABLE 1

Advantageous primer pairs for detection of nucleic acids listed under a) - i), o), p), q) and t) as defined above, by PCR.

| Target nucleic acid | | | Primers | |
|---|---|---|---|---|
| "Zm" | Fwd: | 5' | TCTCTTCCTCCTTTAGAGCTACCACTA 3' | (SEQ ID NO: 56) |
| | Rev: | 5' | AATCGATCCAAAGCGAGATGA 3' | (SEQ ID NO: 57) |
| "Bn" | Fwd: | 5' | CAGCTCAACAGTTTCCAAACGA 3' | (SEQ ID NO: 24) |
| | Rev: | 5' | CGACCAGCCTCAGCCTTAAG 3' | (SEQ ID NO: 25) |

TABLE 1-continued

Advantageous primer pairs for detection of nucleic acids listed under a) - i), o), p), q) and t) as defined above, by PCR.

| Target nucleic acid | | Primers | |
|---|---|---|---|
| "Gm" | Fwd: | 5' AACCGGTAGCGTTGCCAG 3' | (SEQ ID NO: 58) |
| | Rev: | 5' AGCCCATCTGCAAGCCTTT 3' | (SEQ ID NO: 59) |
| "p35S" | Fwd: | 5' AAAGCAAGTGGATTGATGTGATA 3' | (SEQ ID NO: 60) |
| | Rev: | 5' GGGTCTTGCGAAGGATAGTG 3' | (SEQ ID NO: 61) |
| "tNOS" | Fwd: | 5'-GATTAGAGTCCCGCAATTATACATTTAA-3' | (SEQ ID NO: 9) |
| | Rev: | 5'-TTATCCTAGKTTGCGCGCTATATTT-3' | (SEQ ID NO: 10) |
| "Cry1Ab" | Fwd: | 5'-ACCGGTTACACTCCCATCGA-3' | (SEQ ID NO: 11) |
| | Rev: | 5'-CAGCACCTGGCACGAACTC-3' | (SEQ ID NO: 12) |
| "PAT/bar" | Fwd: | 5'-CGTCAACCACTACATCGAGACAA-3' | (SEQ ID NO: 13) |
| | Rev: | 5'-GTCCACTCCTGCGGTTCCT-3' | (SEQ ID NO: 14) |
| "PAT/pat" | Fwd: | 5'-CCGCGGTTTGTGATATCGTT-3' | (SEQ ID NO: 15) |
| | Rev: | 5'-TCTTGCAACCTCTCTAGATCATCAA-3' | (SEQ ID NO: 16) |
| "CP4-EPSPS" | Fwd: | 5' GCATGCTTCACGGTGCAA 3' | (SEQ ID NO: 22) |
| | Rev: | 5' GGACCTGTGGGAGATAGACTTGTC 3' | (SEQ ID NO: 23) |
| | Rev 1: | 5' TGAAGGACCGGTGGGAGAT 3' | (SEQ ID NO: 62) |
| | Rev 2: | 5' TGAAGGACCTGTGGGAGAT 3' | (SEQ ID NO: 63) |
| "Or" | Fwd': | 5' GCTTAGGGAACAGGGAAGTAAAGT 3' | (SEQ ID NO: 51) |
| | Rev: | 5' CTTAGCATAGTCTGTGCCATCCA 3' | (SEQ ID NO: 21) |
| "Bv" | Fwd: | 5' GACCTCCATATTACTGAAAGGAAG 3' | (SEQ ID NO: 64) |
| | Rev: | 5' GAGTAATTGCTCCATCCTGTTCA 3' | (SEQ ID NO: 65) |
| "Gs" | Fwd: | 5' AGTTTGTAGGTTTTGATGTTACATTGAG 3' | (SEQ ID NO: 66) |
| | Rev: | 5' GCATCTTTGAACCGCCTACTG 3' | (SEQ ID NO: 67) |
| "St" | Fwd: | 5' GGACATGTGAAGAGACGGAGC 3' | (SEQ ID NO: 68) |
| | Rev: | 5' CCTACCTCTACCCCTCCGC 3' | (SEQ ID NO: 69) |

Hence, the invention provides methods as defined in any one of the above aspects A1 to A11 or in any embodiment of said aspects, wherein the presence or absence of nucleic acids from among those listed under a)-i), o), p), q) and t) as defined above in a sample is detected using PCR amplification using the respective primer pairs as shown in Table 1.

Where Table 1 lists more than one forward and/or reverse primer for amplification on a certain nucleic acid (such as, e.g., for "CP4-EPSPS"), any one or any combination of said forward primer(s) may be used in conjunction with any one or with any combination of said reverse primer(s) to obtain amplification.

One shall appreciate that while the primer sequences listed in Table 1 have been perfected to provide for optimal amplification, the present methods can perform adequately when using variant primers that display a certain restricted degree of sequence variation vis-à-vis the primers in Table 1.

Hence, the above aspects and embodiments also encompass methods wherein the nucleic acids of interest are detected by PCR amplification using variant primers that include one or more sequence variations vis-à-vis the corresponding primers listed in Table 1, such as, e.g., one or more deletion, insertion and/or substitution, insofar such variant primers/primer pairs can still achieve adequate amplification of their respective amplicons. Preferably, such variant primers would show at least 85%, more preferably at least 90%, even more preferably at least 95%, and yet more preferably at least 96%, at least 97%, at least 98% or at least 99% sequence identity to the primers listed in Table 1. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250).

One shall further appreciate that the primers listed in Table 1 or variants thereof may be advantageously derivatised. For example, said primers or variants thereof may be labelled to allow detection of the amplified products, such as, e.g., in real-time PCR applications. Hence, such derivatisation may for example entail introducing one or more label moiety and/or one or more accessory moiety (e.g., a quenching moiety, a FRET moiety, etc.), and optionally where required modifying the primer sequence to allow for the introduction and/or proper working of said moiety or moieties. A skilled person is generally knowledgeable about ways to modify primers and primer pairs for purposes of labelling. The use of so-derivatised primers and primer pairs can be particularly useful in real-time PCR, and particularly where two or more differently labelled amplification products are to be followed in multiplexed amplification reactions.

Hence, the above aspects and embodiments also encompass methods where the nucleic acids of interest are detected by PCR amplification using derivatives of the primers and primer pairs listed in Table 1 or of variants thereof.

By means of an example, in a preferred aspect ("A12"), the invention offers a method to examine a sample for the presence or absence of material derived from one or more transgenic plant events (in particular one or more maize and/or oilseed rape and/or soybean and/or rice and/or sugar beet and/or cotton and/or potato transgenic plant events) comprising the steps of:

(1) detecting the presence or absence in the sample of nucleic acids comprising or consisting of:
one, more than one or all of nucleic acids chosen from those listed under a), b), c), o), p) q) and t) as defined above, and
one, more than one or all of nucleic acids chosen from those listed under d)-i) as defined above; and
(2) concluding the presence or absence in the sample of material derived from one or more transgenic plant events, such as events chosen from the group comprising or consisting of: events Bt176, Bt11, Bt10, MON810, MON863, TC1507, NK603, T25, GA21, DAS-59122, optionally MIR604, LY038 and MON88017, crosses thereof, and related events thereof; events Topas 19/2, MS1, RF1, RF2, RF3, MS8, GT73, T45, Liberator pHoe6/Ac, GS40/90pHoe6/Ac, optionally OXY235, crosses thereof including MS1/RF1, MS1/RF2, MS8/RF3, and related events thereof; events MON 40-3-2, MON89788, A2704-12, A5547-127, crosses thereof, and related events thereof; events LL62, LL06 and LL601, crosses thereof, and events related thereof; events T120-7, H7-1 and A5-15, crosses thereof, and events related thereto; events LL cotton 25, MON 1445, MON 531, MON15985, crosses thereof, and events related thereto; and event EH92-527-1 and events related thereto,
wherein in step (1) the presence or absence of nucleic acids in a sample is detected using PCR amplification using the respective primers and primer pairs as shown in Table 1, or variants or derivatives thereof.

For reasons clarified above, step (1) of aspect A12 can preferably involve detecting the presence or absence in the sample of nucleic acids comprising all nucleic acids listed under d)-i) as defined above. In a preferred embodiment, step (1) of aspect A12 can preferably involve detecting the presence or absence in the sample of nucleic acids comprising at least nucleic acids listed under a)-i) as defined above.

In an aspect, the invention further provides primers and primer pairs and variants or derivatives thereof suitable for amplification of amplicons from nucleic acids comprising or consisting of those listed under a)-u) above. In particular, in view of the significant effort invested by the present inventors to the identification of the primer pairs listed in Table 1, the invention provides the primers and primer pairs listed in Table 1, as well as variants and derivatives thereof, optionally in any suitable combination of said primers and/or primer pairs or variants or derivatives thereof.

Additionally, the invention also provides amplification products obtainable using the preferred primers and primer pairs, vectors and plasmids comprising said amplification products, and recombinant microorganisms transformed with and harbouring said vectors and plasmids. Consequently, in preferred embodiments, the invention also relates to recombinant *E. coli* as deposited under the Budapest Treaty with the Belgian Coordinated Collections of Microorganisms (BCCM), Laboratorium voor Moleculaire Biologie—Plasmidencollectie (BCCM/LMBP) (Universiteit Gent, Technologiepark 927, B-9052 Gent-Zwijnaarde, Belgium) on Jan. 10, 2007 under LMBP accession numbers LMBP 5452, LMBP 5453, LMBP 5454, LMBP 5455, LMBP 5456, LMBP 5457, LMBP 5458, LMBP 5459 and LMBP 5460, on Mar. 6, 2007 under LMBP accession number LMBP 5451, and on Apr. 19, 2007 under LMBP accession numbers LMBP 5587, LMBP 5588, LMBP 5589 and LMBP 5590, as well as to isolated recombinant plasmids obtainable from the said recombinant *E. coli*, as well as to isolated inserts of the said plasmids, preferably isolated EcoRI-EcoRI inserts thereof.

Such plasmids or vectors or inserts thereof, and their combinations, are particularly useful as positive controls, references and/or calibrators for the respective amplicons in the amplification reactions of the above methods.

In addition, the invention also covers kits comprising one or more reagents useful in the methods of one or more of the above aspects and embodiments. For example, such kits can comprise one or more of the above primers and/or primer pairs, particularly as listed in Table 1, or variants or derivatives of said primers, and/or one or more of the above amplification products, vectors or plasmids comprising such, or inserts of the said vectors or plasmids, and/or a data carrier comprising instructions for a programmable computing device to carry out the step (2) of the methods of the invention (see below). Such kits may further conveniently contain instructions for the user to perform the methods of the invention and to interpret the data so-obtained.

The invention also teaches an uncomplicated and straightforward way to perform step (2) of the above aspects and embodiments, i.e., to conclude the potential presence or absence in the sample of material derived from the various transgenic plant events of interest. In particular, the results acquired for a sample in step (1) of the above aspects and embodiments are represented as a set "$G_{SAM}$" consisting of, i.e., representing a collection of, those nucleic acids chosen from ones comprising or consisting of those listed under a)-u) above that were detected in the said step (1) as being present in the sample (step (i)).

Moreover, any transgenic plant event of interest can be represented as a set "$G_X$" (where X designates the event of interest), consisting of, i.e., representing a collection of, those nucleic acids chosen from ones comprising or consisting of those listed under a)-u) above that are found in the said event and thus would be detected in step (1) if the sample contained material derived from the said event, or a cross involving such, or a related event (step (ii)).

In particular exemplary embodiments, the set $G_X$ may preferably be chosen from sets representing the events specifically recited above, e.g., comprising sets: maize event sets $G_{Bt176} \in \{Zm; p35S; Cry1Ab; PAT/bar\}$, $G_{Bt11} \in \{Zm; p35S; tNOS; Cry1Ab; PAT/pat\}$, $G_{Bt10} \in \{Zm; p35S; tNOS; Cry1Ab; PAT/pat\}$, $G_{MON810} \in \{Zm; p35S; tNOS; Cry1Ab\}$, $G_{MON863} \in \{Zm; p35S; tNOS\}$, $G_{TC1507} \in \{Zm; p35S; PAT/pat\}$, $G_{NK603} \in \{Zm; p35S; tNOS; CP4-EPSPS\}$, $G_{T25} \in \{Zm; p35S; PAT/pat\}$, $G_{GA21} \in \{Zm; tNOS\}$, $G_{DAS-59122} \in \{Zm; p35S; PAT/bar\}$, $G_{MIR604} \in \{Zm; tNOS; mCry3A\}$, $G_{LY038} \in \{Zm; p35S; tNOS; cordapA; Glb1\}$, and $G_{MON88017} \in \{Zm; p35S; tNOS; CP4-EPSPS; Cry3Bb1\}$, oilseed rape event sets $G_{Topas\ 19/2} \in \{Bn; p35S; PAT/pat\}$, $G_{MS1} \in \{Bn; tNOS; PAT/bar\}$, $G_{RF1} \in \{Bn; tNOS; PAT/bar\}$, $G_{RF2} \in \{Bn; tNOS; PAT/bar\}$, $G_{MS1/RF1} \in \{Bn; tNOS; PAT/bar\}$, $G_{MS1/RF2} \in \{Bn; tNOS; PAT/bar\}$, $G_{MS8} \in \{Bn; tNOS; PAT/bar\}$, $G_{RF3} \in \{Bn; tNOS; PAT/bar\}$, $G_{MS8/RF3} \in \{Bn; tNOS; PAT/bar\}$, $G_{GT73} \in \{Bn; CP4-EPSPS\}$, $G_{T45} \in \{Bn; p35S; PAT/pat\}$, $G_{Liberator\ pHoe6/Ax} \in \{Bn; p35S; PAT/pat\}$, $G_{GS40/90pHoe6/Ac} \in \{Bn; p35S; PAT/pat\}$, $G_{OXY235} \in \{Bn; p35S; Bxn\}$; soybean event sets $G_{MON40-3-2} \in \{Gm; p35S; tNOS; CP4-EPSPS\}$, $G_{MON89788} \in \{Gm; CP4-EPSPS\}$, $G_{A2704-12} \in \{Gm; p35S; PAT/pat\}$, and $G_{A5547-127} \in \{Gm; p35S; PAT/pat\}$, rice event sets $G_{LL62} \in \{Or; p35S; PAT/bar\}$, $G_{LL06} \in \{Or; p35S; PAT/bar\}$ and $G_{LL601} \in \{Or; p35S; tNOS; PAT/bar\}$, sugar beet event sets $G_{T120-7} \in \{Bv; p35S; PAT/pat\}$, $G_{H7-1} \in \{Bv; p35S; CP4-EPSPS\}$, and $G_{A5-15} \in \{Bv; p35S; tNOS; CP4-EPSPS\}$, cotton event sets $G_{LL\ cotton\ 25} \in \{Gs; p35S; tNOS; PAT/bar\}$, $G_{MON1445} \in \{Gs; p35S; tNOS; CP4-EPSPS\}$, $G_{MON531} \in \{Gs; p35S; tNOS; cry1Ac\}$ and $G_{MON15985} \in \{Gs; p35S; tNOS; cry1Ac; cry2Ab2\}$, and potato event set $G_{EH92-527-1} \in \{St; tNOS; Gbss\}$; wherein the designations between brackets { } refer to those nucleic acids as listed under a)-u) above that are found in such events and may thus be detected in materials derived there from. It is to be understood that if the detection step (1) involves additional nucleic acids other than those listed under a)-u) above, such nucleic acids can be advantageously included in the above sets.

It shall be understood that where the above methods do not test the presence of all nucleic acids under a)-u) above, the sample set as well as the event sets can be defined in terms of those nucleic acids the presence of which is effectively tested. By means of example and not limitation, where the presence of nucleic acids listed under j)-n), r) s) and u) as defined above, which correspond to specific traits in addition to those defined under d)-i), is not tested, then the sets corresponding to several events may be defined in a narrower manner, in particular: maize event sets $G_{MIR604} \in \{Zm; tNOS\}$, $G_{LY038} \in \{Zm; p35S; tNOS\}$, $G_{MON88017} \in \{Zm; p35S; tNOS; CP4\text{-}EPSPS\}$; oilseed rape event set $G_{OXY235} \in \{Bn; p35S\}$; cotton event sets $G_{MON531} \in \{Gs; p35S; tNOS\}$, $G_{MON15985} \in \{Gs; p35S; tNOS\}$; and potato event set $G_{EH92\text{-}527\text{-}1} \in \{St; tNOS\}$.

Hence, the presence of material derived from an event of interest X in the sample can then be determined by performing for the respective set of interest $G_X$ logical operations as follows (step iii):

if $G_X$ equals $G_{SAM}$ ($G_X = G_{SAM}$), then material derived from the transgenic plant event X, or from a cross thereof, or from an event related thereto, is potentially present in the sample;

if $G_X$ is a proper subset of $G_{SAM}$ ($G_X \subset G_{SAM}$), then material derived from transgenic plant event X, or from a cross thereof, or from an event related thereto, is potentially present in the sample;

if $G_X$ does not equal $G_{SAM}$ and $G_X$ is not a proper subset of $G_{SAM}$, ($G_X \neq G_{SAM}$ and $G_X \not\subset G_{SAM}$), then material derived from transgenic plant event X, or from a cross thereof, or from an event related thereto, is absent from the sample.

In preferred embodiments, these logical operations can be advantageously carried out by a computing device.

It shall be appreciated that whereas the above algorithm for use in step (2) of the present methods is herein explained in connection with concluding the presence of material from certain events using detection of particular nucleic acids, said algorithm is in principle readily applicable to methods which aim to conclude the presence of any events, such as events other than or additional to those specifically mentioned above, using detection of any nucleic acids, such as nucleic acids other than or additional to those listed under a)-u) above.

These and further aspects and preferred embodiments of the invention are described in the following sections and in the appended claims.

BRIEF DESCRIPTION OF FIGURES

FIG. 1 (A-F) illustrates select sequences of amplicons amplified using primers sets listed in Table 4 and present in cloning vectors, particularly in pUC18, such as plasmids listed in Table 5. As can be appreciated, the sequences may include partial sequences from multiple cloning sites flanking the inserted amplicons.

DETAILED DESCRIPTION OF THE INVENTION

Figure 2:
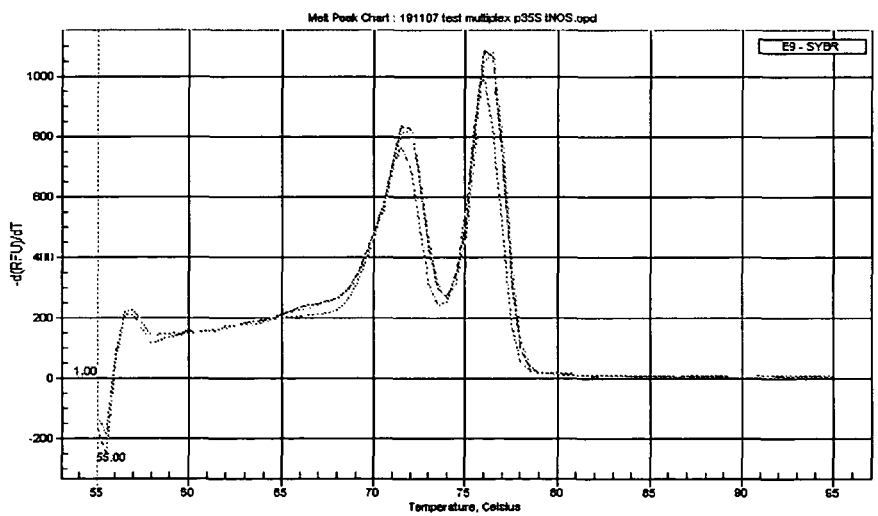
FIG. 2 (A) results of the multiplex PCR test for p35S/tNOS, (B) Dissociation curve of p35S/tNOS specific multiplex test.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The term "about" as used herein when referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

The recitation of numerical ranges by endpoints includes all numbers and fractions subsumed within that range, as well as the recited endpoints.

All documents cited in the present specification are hereby incorporated by reference in their entirety. In particular, the teachings of all documents herein specifically referred to are incorporated by reference.

Hence, in some aspects, more particularly aspects A1-A12 as described in the Summary section, the invention concerns methods to examine a sample for the presence or absence of material derived from one or more transgenic plant events comprising the steps (1) detecting the presence or absence in the sample of nucleic acids comprising or consisting of one, more than one or all (the particular choice depending on the goal of a given assay) of nucleic acids listed under a)-u) in the Summary section, and (2) concluding the presence or absence in the sample of material derived from one or more transgenic plant events chosen from the group comprising or consisting of some or all of those detailed in the Summary section.

A "transgenic plant event" occurs with an independent transformation of plant cells with heterologous nucleic acid, typically a nucleic acid construct comprising one or more transgenes of interest; regeneration of a population of plants resulting from an insertion of the construct or a part thereof including the said transgene(s) of interest into the genome of the plants; and selection of a particular plant characterised by the said insertion into one or more, preferably one, particular genome location. The term "transgenic plant event" thus encompasses the original so-selected transformant plant, as well as any successive progeny thereof comprising the inserted nucleic acid including the transgene(s) of interest; for example, the said progeny may be hemizygous or homozygous for the said insertion; the said progeny may be obtained, e.g., by vegetative propagation or by sexual crossing.

The term "plant" as used herein generally encompasses plant cells; plant protoplasts; plant tissues; plant cells or tissue culture from which a plant organism can be regenerated; plant calli or clumps; plant organisms and parts thereof, such as, without limitation, flowers, tepals, petals, sepals, anthers, pollen, seeds, fruit, pericarp, pods, leaves, petioles, stems, roots, rhizomes, stolons, tubers, shoots, and the like. The term as used herein generally encompasses plants of any taxons classified in the art within the kingdom Plantae. In addition, plant as understood herein may preferably belong to land plants (embryophytes) including, without limitation, non-vascular plants (bryophytes) and vascular plants (tracheophytes); more preferably, to vascular plants (tracheophytes) including, without limitation, lycopodiophyta, equisetophyta, pteridophyta, psilotophyta, ophioglossophyta, and seed plants (spermatophytes); even more preferably to seed plants (spermatophytes) including, without limitation, seed-bearing plants (gymnosperms) such as, e.g., pinophyta, cycadophyta, ginkgophyta and gnetophyta and flowering plants (angiosperms) such as magnoliophyta, including monocots (liliopsida) and dicots (Magnoliopsida). Preferred plants may be ones commonly applied in agriculture or horticulture. By means of example and not limitation, preferred crop plants can include maize, wheat, rice, barley, sorghum, tobacco, tomato, potato, oilseed rape (rapeseed), soybean, sugar beet, pea, sunflower, cotton, peanut, flowers (e.g., carnation), etc.

The term "material" generally refers to physical matter. The term "material derived from a transgenic plant event" encompasses the transgenic plant event as such, including, by means of example and not limitation, the transgenic plant event organism; any parts of the transgenic plant event organism, such as, e.g., flowers, tepals, petals, sepals, anthers, pollen, seeds, fruits, pericarp, pods, leaves, petioles, stems, roots, rhizomes, stolons, tubers or shoots, or portions thereof; cells, protoplasts, tissues, calli or clumps of the transgenic plant event; or material obtained by subjecting any of the above to one or more downstream processing steps. These downstream processing steps may comprise any actions used to process particular plant materials in agriculture, horticulture or in any downstream industries, e.g., food industry including beverage industry, feed industry, textile industry (e.g., cotton, linen, bamboo, etc.), fuel industry (e.g., oilseed rape), lubricant industry (e.g., castor oil), paint industry (e.g., linseed oil, tung oil), cosmetic and pharmaceutical industry, etc.

By means of example and not limitation, such downstream processing may include harvesting; removal of unwanted outer layers, e.g., peeling, skinning, etc.; drying, e.g., air drying, sun drying, spray drying, freeze drying, juice concentrating, etc.; diminution, e.g., grinding, milling, chopping, slicing, etc.; liquefaction, e.g., juice collection; preserving, e.g., vacuum bottling, tinning, canning, pasteurization, addition of preservatives, etc.; pressing, e.g., oil collection; hydrogenation, e.g., vegetable oil saturation; macerating; emulsifying; heat treatment, e.g., cooking, pressure cooking, steaming, oven baking, smoking, frying, grilling, etc.; fermenting, e.g., by yeast, bacteria and/or fungi; freezing; and the like.

The term "sample" as used herein refers broadly to a representative part or fraction of a larger material whole being presented for inspection, such as, e.g., for quality control. Preferably, a sample to be examined by methods of the invention may be suspected of potentially comprising material derived from one or more transgenic events of interest. By means of example, such suspicion may exist for any sample representative of material that is known as comprising, or suspected of probably or possibly comprising, plants or parts thereof or material derived therefrom. In a preferred example, the sample may be representative of material that is known as comprising, or suspected of probably or possibly comprising, plants or parts thereof or material derived therefrom, wherein the said plants or parts thereof belong to the same taxon as a transgenic event of interest whose presence in the sample is to be examined. For example, a sample may be representative of plants or parts thereof, e.g., collected or harvested plants or parts thereof (such as, without limitation, fruits, seeds, pods, flowers, etc.), or representative of an intermediary or final material obtained by applying one or more downstream processing steps thereto, or of products comprising such material, e.g., of processed food or feed products.

Hence, in an embodiment the sample can comprise plants or parts thereof, including flowers, tepals, petals, sepals, anthers, pollen, seeds, fruits, pericarp, pods, leaves, petioles, stems, roots, rhizomes, stolons, tubers or shoots, or portions thereof, plant cells, plant protoplasts and/or plant tissues, and/or plant-derived material, preferably food or feed material, including processed food or feed material.

The methods of the invention detect the presence or absence in the sample of nucleic acids, i.e., of genetic material and preferably genomic DNA, originating or derived from transgenic plant events of interest. The presence or absence of such nucleic acids is indicatory of, respectively, the presence or absence in the sample of this and potentially further material derived from the respective transgenic plant events; such as, e.g., materials co-purifying or co-separating with the said nucleic acids during the various processing steps applied to the transgenic plant events.

It is known that nucleic acids, and particularly genomic DNA, are comparably durable and can tolerate a variety of processing steps applied to plant materials in agriculture and industry, e.g., in food or feed industry, such that DNA molecules of lengths that permit sequence-specific detection thereof may be found following such steps and even in final products.

Accordingly, a preferred sample of the invention comprises nucleic acids, more preferably genomic DNA, even more preferably genomic DNA having at least sizes that allow for sequence specific-detection thereof, such as, e.g., on average, at least about 20 bp, e.g., at least about 30 bp, preferably at least about 50 bp, e.g., at least about 75 bp, more preferably at least about 100 bp, e.g. about 150 bp, or even more preferably at least about 200 bp, or at least about 300 bp, or at least about 500 bp, or at least about 1 kb, or more.

Although it can be assumed that most processing steps to which a transgenic plant event would be commonly exposed in practice would preserve detectable nucleic acids as above in the eventual product, and thus in the sample thereof to be examined, the inventors also envisage a positive control aimed at verifying whether the said sample comprises detectable plant-derived nucleic acids.

In particular, the method of the invention may further comprise detecting the presence or absence in the sample of a generic plant-derived nucleic acid. In a preferred embodiment, such generic plant-derived nucleic acid is derived from a gene present in and preferably highly conserved (e.g., ≥80%, preferably ≥90%, more preferably ≥95%, even more preferably ≥96%, ≥97%, ≥98% or ≥99% sequence identity) between various plant taxons; preferably at least within spermatophytes; or at least within angiosperms, such as between and/or within monocots and dicots; or preferably at least between plant taxons commonly used in agriculture and industry, such as, without limitation, between maize, wheat, rice, barley, sorghum, tobacco, tomato, potato, oilseed rape (rapeseed), soybean, sugar beet, pea, sunflower, cotton, peanut and flowers (e.g., carnation); or preferably at least between plant taxons comprising or consisting of those of the transgenic plant events tested in the sample.

In preferred embodiments, the said generic plant-derived nucleic acid is derived from the chloroplastic small subunit of Rubisco gene or from the CHL-tRNA synthetase gene.

As mentioned, the methods of the invention include in step (1) detecting the presence or absence in the sample of nucleic acids comprising or consisting of one, more than one or all of those listed under a)-u) in the Summary section. The term "detecting" or "detection" as used herein encompasses any means of determining the presence or absence of a given nucleic acid in the sample.

Preferably, the presence of a particular nucleic acid molecule in a sample can be detected using one or more reagents specifically hybridising to respective nucleotide sequence(s) comprised within the said nucleic acid molecule.

The terms "hybridisation" and "hybridise" refer to a process by which a nucleic acid strand anneals with complementary or substantially complementary sequence(s) comprised in the same or another polynucleotide strand through base pairing, preferably Watson-Crick base pairing.

The terms "complementary" and "complementarity" refer to the normal binding of polynucleotides under permissive salt (ionic strength) and temperature conditions by base pairing, preferably Watson-Crick base pairing. By means of example, complementary Watson-Crick base pairing occurs between the bases A and T, A and U or G and C. For example, the sequence A-G-T (i.e., 5'-A-G-T-3') is thus complementary sequence A-C-T (i.e., 5'-A-C-T-3').

The "degree of complementarity" of a nucleic acid strand (A) to a nucleic acid strand (B) can be expressed as the proportion (percentage) of nucleotides of the nucleic acid strand (A) that would be expected to match, i.e., form Watson-Crick base-pairing, with nucleotides of the nucleic acid strand (B), when the said nucleic acid strands (A) and (B) were annealed, preferably in high stringency conditions.

"Complementary" as used herein thus refers to wholly complementary, such that all respective nucleotides of the nucleic acid strands would bind when the strands anneal. By means of example, a relatively shorter nucleic acid strand would show total complementarity to a relatively longer nucleic acid strand, if the latter strand comprised a sequence fully complementary to the sequence of the former strand. "Substantially complementary" refers to largely but not wholly complementary, in particular, to at least 85% complementary, e.g., at least 90% complementary, preferably at least 95% complementary, e.g., at least 96%, 97%, 98% or at least 99% complementary.

"Specifically hybridise" and "specific hybridisation" reflects a situation when a reagent hybridises to a given sequence more readily than it would hybridise to a random, unrelated sequence. For example, a reagent specifically hybridising to a given nucleotide sequence (A) preferably displays little or no hybridisation to other polynucleotides, and preferably to homologues or orthologues of the nucleic acids sequence (A), under conditions where it would specifically hybridise with the said polynucleotide (A).

Preferably, reagents that can specifically hybridise to the respective nucleotide sequence(s) comprised within the nucleic acid molecules listed under a)-u) above can be probes or primers.

A "probe" is an isolated nucleic acid to which is desirably attached a detectable label or reporter moiety, e.g., a radioactive isotope (e.g., $^{32}P$, $^{33}P$), ligand, chemiluminescent agent, fluorophore (e.g., fluorescein, tetrachloro-fluorescein, TAMRA, ROX, Cy3, Cy3.5, Cy5, Cy5.5, Texas Red, etc.), vitamin (e.g., biotin), steroid (e.g., digoxin), enzyme (e.g., HRP, AP, etc.), etc. Such a probe is complementary or substantially complementary to a sequence comprised in a strand of a target nucleic acid, in the case of the present invention, of a nucleic acid, preferably genomic DNA, listed under a)-u) above. Probes according to the present invention may be deoxyribonucleic acids, ribonucleic acids, or nucleic acids comprising both deoxyribo- and ribonucleotides; may comprise standard purine and/or pyrimidine bases (A, G, T, C, U and/or I), but also other natural, chemically or biochemically modified (e.g., methylated), non-natural, or derivatised nucleotide bases; may include backbone comprising sugars and phosphate groups, as can typically be found in RNA or DNA, as well as one or more modified or substituted (such as, 2'-O-alkylated, e.g., 2'-O-methylated or 2'-O-ethylated; or 2'-O,4'-C-alkynelated, e.g., 2'-O,4'-C-ethylated) sugars or one or more modified or substituted phosphate groups—for example, backbone analogues in nucleic acids may include phosphodiester, phosphorothioate, phosphorodithioate, methylphosphonate, phosphoramidate, alkyl phosphotriester, sulfamate, 3'-thioacetal, methylene (methylimino), 3'-N-carbamate, morpholino carbamate, and peptide nucleic acids (PNAs).

Probes may be at least 10 nucleotides in length, e.g., at least 11, at least 12, at least 13 or at least 14 nucleotides in length, preferably at least 15 nucleotides, e.g., at least 16, at least 17, at least 18 or at least 19 nucleotides in length, more preferably at least 20 nucleotides in length, e.g., at least 21, at least 22, at least 23, or at least 24 nucleotides in length, even more preferably at least 25 nucleotides in length, e.g., at least 30, at least 35, at least 40, at least 45, at least 50, at least 75, at least 100 or at least 200 or more nucleotides in length.

"Primers" are isolated nucleic acids, preferably deoxyribonucleic acids or, in other preferred examples, ribonucleic acids or PNAS, complementary or substantially complementary to a sequence comprised in a target nucleic acid (in the case of the present invention, to a sequence comprised in a nucleic acid, preferably genomic DNA, comprising or consisting of those listed under a)-u) above), that can be annealed to the said target nucleic acid and can act as a point of initiation of synthesis of a primer extension product in the presence of nucleotides and an agent for nucleic acid polymerization, such as DNA dependent or RNA dependent polymerase.

A primer needs to be sufficiently long to prime the synthesis of an extension products in the presence of an agent for polymerization. A typical primer may thus be at least 10 nucleotides in length, e.g., at least 11, at least 12, at least 13 or at least 14 nucleotides in length, preferably at least 15 nucleotides in length, e.g., at least 16, at least 17, at least 18 or at least 19 nucleotides in length, more preferably at least 20 nucleotides in length. Further preferred primers are between about 10 and about 40 nucleotides in length, more preferably between about 15 and about 30 nucleotides in length, most preferably between about 20 and about 25 nucleotides long.

"Primer pairs" refer to combinations of primers which are suited for amplification of amplicons from within target nucleic acids (in the case of the present invention, from within nucleic acids, preferably genomic DNA, comprising or consisting of those listed under a)-u) above) by suitable nucleic-acid amplification methods. Accordingly, the ability to amplify an amplicon from within a given target nucleic acid using a primer pair designed to specifically hybridise within the said target nucleic acid indicates the presence (and optionally quantity) of the said target nucleic acid in the sample.

Exemplary but non-limiting methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989 ("Sambrook et al. 1989"); Current Protocols in Molecular Biology, ed. Ausubel et al., Greene Publishing and Wiley-Interscience, New York, 1992 (with periodic updates) ("Ausubel et al. 1992"); and Innis et al., PCR Protocols: A Guide to Methods and Applications, Academic Press: San Diego, 1990. PCR-primer pairs can be derived from a known sequence, for example, by using computer programs intended for that purpose such as Primer3

(Rozen and Skaletsky. 2000. Primer3 on the WWW for general users and for biologist programmers. In: Krawetz S, Misener S (eds) Bioinformatics Methods and Protocols: Methods in Molecular Biology. Humana Press, Totowa, N.J., pp 365-386) or the GCG™ v. 11.1.2 package from Accelrys.

Specific hybridisation of the probes, primers or primer pairs of the invention to their respective complementary sequences within the target nucleic acids, e.g., those comprising or consisting of those listed under a)-u) above, can be preferably achieved under high stringency hybridisation conditions.

"High stringency" conditions include conditions equivalent to the following exemplary conditions for binding or hybridisation at 65° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent (50×Denhardt's contains per 500 ml: 5 g Ficoll (Type 400, Pharmacia), 5 g BSA (Fraction V; Sigma) and 100 µg/ml denatured salmon sperm DNA), followed by washing in a solution comprising 5×SSPE, 0.1% SDS at 65° C. when a probe of about 500 nucleotides in length is employed. Other exemplary conditions for hybridisation at "high stringency" for nucleic acid sequences over approximately 20-100 nucleotides in length, preferably about 30-100 nucleotides in length, e.g., between 30-50 nucleotides in length, include conditions equivalent to hybridisation in 6×SSC at 45° C., followed by one or more washes in 0.2×SSC, 0.1% SDS or even 0.1×SSC, 0.1% SDS at 65° C. Numerous equivalent conditions may be employed to vary stringency conditions; factors such as the length and nature (DNA, RNA, base composition) of the probe and nature of the target (DNA, RNA, base composition, present in solution or immobilised, etc.) and the concentration of the salts and other components (e.g., the presence or absence of formamide, dextran sulphate, polyethylene glycol) are considered and the hybridisation solution may be varied to generate conditions of low or high stringency hybridisation different from, but equivalent to, the above listed conditions. In addition, the art knows conditions that promote hybridisation under conditions of high stringency (e.g., increasing the temperature of the hybridisation and/or wash steps, the use of formamide in the hybridisation solution, etc.). Guidance for performing hybridisation reactions can be found, for example, in Current Protocols in Molecular Biology, John Wiley & Sons, N.Y., 6.3.1-6.3.6, 1989, and more recent updated editions, all of which are incorporated by reference.

Regarding the amplification of amplicons from within the target nucleic acids using primer pairs, "stringent conditions" or "high stringency conditions" are conditions that permit a primer pair to hybridise only to its respective target nucleic-acid sequence and to produce a unique amplification product, i.e., the amplicon, substantially without producing non-intended, i.e., non-specific amplification products. For example, preferably less than 20%, more preferably less than 10%, even more preferably less than 5%, e.g., less than 4%, less than 3%, or less than 2%, yet more preferably less than 1%, e.g., less than 0.1% or less than 0.01% of the total quantity (e.g., weight) of amplification product in an amplification reaction would be non-specific when such reaction is performed at stringent conditions (e.g., as analysed by quantitative gel electrophoresis, or by Tm determination, or the like).

Any conventional methods can be used to detect specific hybridisation of a probe to a target nucleic acid in the sample. For example, nucleic acids, preferably DNA, from a sample may be immobilised and denatured on a solid support and so-hybridised with respective probes (e.g., Southern blotting, slot blotting, dot blotting, etc.). If a probe—and consequently its detectable label—is retained on the solid support, this indicates that the target nucleic for which the probe is specific is present in the sample.

Similarly, any existing nucleic-acid amplification method can be used to amplify amplicons from within target sequences of interest, thereby indicating the presence of the corresponding target sequences in the sample: including but not limited to the polymerase chain reaction (PCR) (U.S. Pat. No. 4,683,202; U.S. Pat. No. 4,965,188), strand displacement amplification (SDA) (U.S. Pat. No. 5,455,166; EP 0684315), LCR, TAS, 3SR, NASBA (U.S. Pat. No. 5,409,818; EP 0329822), RCA and Q-beta amplification.

In a particularly preferred embodiment, the methods of the invention employ polymerase-chain reaction (PCR) to amplify amplicons from within target nucleic acids chosen from ones comprising or consisting of those listed under a)-u) above. The terms "polymerase-chain reaction" and "PCR" broadly covers any method referred as such in the art and in particular methods for amplification of target nucleic acid sequences, especially target DNA sequences, using heat-stable DNA polymerase(s) and two primers, especially oligonucleotide primers, one complementary to the (+)-strand at one end of the sequence to be amplified and the other complementary to the (−)-strand at the other end. The term encompasses modifications of the prototypic PCR, such as, e.g., high-fidelity PCR, hot-start PCR, touch-down PCR, nested PCR, multiplex PCR, quantitative PCR, quantitative real-time PCR, long-range PCR, RT-PCR, etc. (see, e.g., PCR Protocols: A Guide to Methods and Applications, eds. Innis et al., Academic Press, San Diego, 1990).

Amplification products obtained using the above amplification methods, and in particular using PCR, can be evaluated, e.g., for their presence or absence, for their specificity and/or quantity, by any of the manners common in the art. For example, the size (as an indication of amplification specificity) and/or quantity of an amplification product may be evaluated using gel electrophoresis, such as, e.g., agarose or polyacrylamide gel electrophoresis, where amplification products are visualised using suitable DNA-binding dyes, such as, e.g., ethidium bromide.

Alternatively, amplification products may be evaluated by methods that employ probes hybridising to specific sequences within the amplification products. For instance, an amplification product may be immobilised and denatured on a solid support and subsequently hybridised with a labelled probe.

Otherwise, the amplification product may itself be labelled, e.g., by including a detectable label (e.g., a fluorophore) in one or both primers and/or by virtue of substrate nucleotides incorporated into the amplification product during amplification, and the so-obtained PCR product may be subsequently denatured and hybridised with specific (oligonucleotide) probes attached to a solid support. The presence and quantity of the detectable label in select positions on the solid support thus indicates the specificity and quantity, respectively, of the amplification product. For instance, such set-up is suitable for use with probe arrays, e.g., microarrays.

In further exemplary manners, amplification products may be evaluated using cloning and sequencing; direct sequencing; oligonucleotide-mediated pyrosequencing (Ahmadian et al. 2000. Anal Biochem 280: 103-110); chromatography, e.g., DHPLC, oligonucleotide ligation assays (Landegren et al. 1988. Science 241: 1077; Eggerding et al. 1995. Hum Mutat 5: 153-165; Nickerson et al. 1990. PNAS 87: 8923-8927); RNAse Protection Assay; etc.

A particularly advantageous manner of evaluating the amplification product is real-time amplification, especially real-time PCR. The term "real-time amplification" is intended to mean any amplification technique, preferably PCR ("real-time PCR"), which makes it possible to monitor the evolution of an ongoing amplification reaction (see, e.g., Real-Time PCR: An Essential Guide, eds. Edwards et al., Horizon Scientific Press, 2004; Marras SAE et al. 2006. Real-time assays with molecular beacons and other fluorescent nucleic acid hybridization probes. Clin Chim Acta 363: 48-60; for discussion of various real-time PCR platforms).

By means of example and not limitation, real-time amplification, especially real-time PCR, as intended herein encompasses fully conventional systems, such as, e.g., the TaqMan™ system developed by Applied Biosystems, which relies on the release and detection of a fluorogenic probe during each round of DNA amplification (Holland et al. 1991. Detection of specific polymerase chain reaction product by utilizing the 5'-3' exonuclease activity of *Thermus aquaticus* DNA polymerase. PNAS 88: 7276-80). The method uses the 5' exonuclease activity of Taq polymerase during primer extension to cleave a dual-labelled, fluorogenic probe hybridised to the target DNA between the PCR primers. Prior to cleavage, a reporter fluorophore, such as 6-carboxyfluorescein (6-FAM) at the 5' end of the probe is quenched by 6-carboxy-tetramethylrhodamine (TAMRA) through fluorescent resonance energy transfer (FRET). Following digestion, FAM is released. The resulting fluorescence measured in real-time at around 518 nm during the log phase of product accumulation is proportional to the number of copies of the target sequence.

Further real-time amplification, especially real-time PCR, detection systems can also utilise FRET, such as, e.g., systems based on molecular beacons. Molecular beacons are single-stranded polynucleotide probes that possess a stem-and-loop hairpin structure. The loop portion is a probe sequence complementary to a sequence within an amplicon to be evaluated, and the stem is formed by short complementary sequences located at the opposite ends of the molecular beacon. The molecular beacon is labelled with a fluorophore (e.g., 6-FAM) at one end and a quencher (e.g., TAMRA) at the other end. When free in solution, the stem keeps the fluorophore and the quencher in close proximity, causing the fluorescence of the fluorophore to be quenched by FRET. However, when bound to its complementary target, the probe-target hybrid forces the stem to unwind, separating the fluorophore from the quencher, and restoring the fluorescence. Accordingly, when the quantity of an amplicon increases during amplification, this can be monitored as an increase in the fluorescence of the corresponding beacon (see, e.g., Manganelli et al. 2001. Real-time PCR using molecular beacons. Methods Mol Med 54: 295-310; Marras SAE. 2006. Selection of fluorophore and quencher pairs for fluorescent nucleic acid hybridization probes. Methods Mol Biol 335: 3-16; Marras SAE et al. 2006. Real-time assays with molecular beacons and other fluorescent nucleic acid hybridization probes. Clin Chim Acta 363: 48-60 for further discussion of molecular beacons detection).

A particularly advantageous real-time PCR amplification and detection system for use in the present invention is the Light Upon Extension (LUX™) system commercialised by Invitrogen (Carlsbad, Calif.) and described in detail in Nazarenko et al. 2002 (Nucleic Acids Research 30: e37) and Nazarenko et al. 2002 (Nucleic Acids Research 30: 2089-2095). This system employs primer pairs in which usually one of the primers of said primer pair is labelled by a fluorophore (such as, e.g., FAM or JOE or Alexa Fluor 546). The particular structure of the "free" primer quenches the signal of the fluorophore bound thereto, whereas the fluorophore's signal intensity increases when the primer assumes an extended conformation once incorporated into the amplification product. The sequence of the primers of the present invention, such as of the particularly preferred primers as listed in Tables 1 and 4, may be tailored to perform with the LUX™ technology, following instructions of the above publications of Nazarenko et al. 2002 or using software tools provided by Invitrogen. The LUX™ technology is particularly well suited for multiplexing (i.e., performing in a single reaction) of two or more amplifications using different primer sets, since each of the primer sets may be marked using a different fluorophore.

For description of additional ways to detect and evaluate amplification products in real-time (e.g., using adjacent probes; 5'-nuclease probes such as Taqman™; Light-up probes; Duplex scorpion primers; Amplifluor primers; and further alternative fluorescent hybridisation probe formats see, e.g., Marras SAE et al. 2006. Real-time assays with molecular beacons and other fluorescent nucleic acid hybridization probes. Clin Chim Acta 363: 48-60, esp. section 6 and references therein).

In preferred embodiments, the real-time amplification, preferably real-time PCR, of the invention uses (substantially) sequence non-specific reagents to detect and evaluate the accumulation of amplification products. These systems usually employ fluorochromes (fluorescent dyes) that bind to DNA (i.e., DNA-binding), preferably to double-stranded DNA, in a substantially sequence non-specific way, and upon such binding their fluorescence is attained or enhanced. Accordingly, the observed increase in fluorescence is indicative of the appearance and quantity of the accumulated (double-stranded) amplification product. If the said fluorochromes preferentially or exclusively bind to double-stranded DNA and/or if their fluorescence is preferentially or exclusively enhanced when bound to double-stranded DNA, then the specificity of the amplification product can be determined by performing its "melting curve", i.e., fluorescence vs. temperature plot, and determining the Tm of the product, i.e., temperature at which 50% of the product is melted and has thus lost its enhanced fluorescence. The observation of a single expected Tm for an amplification product (or multiple expected Tm in multiplex amplification) corroborates the specificity of amplification.

Exemplary fluorochromes for use in the above sequence non-specific detection methods include, without limitation, major-groove binders, minor-groove binders, intercalating dyes, or the like; such as, e.g., SYBR Green I (2-[N-(3-dimethylaminopropyl)-N-propylamino]-4-[2,3-dihydro-3-methyl-(benzo-1,3-thiazol-2-yl)-methylidene]-1-phenyl-quinolinium; Zipper et al. 2004. Nucleic Acid Res 32: e103), ethidium bromide, Hoechst 33258, PicoGreen™ (Molecular Probes), preferably SYBR Green I or PicoGreen™.

In a further preferred embodiment, the real-time amplification reactions of the present methods can be multiplexed, i.e., two or more different amplicons can be amplified using two or more corresponding primer pairs on the same sample (s) in the same reaction. The primers envisaged by the present inventors, in particular the primers listed in any of Table 1 or Table 4 or variants or derivatives thereof, can be particularly suited for multiplexing applications inter alia because they perform adequately at substantially same or similar reaction conditions (e.g., reaction composition and temperature cycling conditions), as well as because they produce similarly sized products.

It is well-understood that multiplexing generally requires that the different amplification products arising in the reaction can be distinguished. In the present context, if non-sequence specific methods (e.g., SYBR Green or other DNA-binding dye) are used to detect the amplification products, multiplexing can be particularly foreseen where the amplification products have sufficiently dissimilar Tm to be distinguished by performing a melting curve (e.g., Tm differing by about 5° C. or more). However, where amplicon specific detection methods are used (e.g., differently labelled primers or differently labelled probes for different amplicons), far-going multiplexing of the present tests is in principle possible.

Hence, target for the above described detection using probes and/or template for the amplification using primer pairs, would be nucleic acid originating from respective transgenic plant events comprised in the sample. Preferably, this target and/or template nucleic acid would be genomic DNA originating from the said transgenic events which, due to its greater stability, is expected to be better preserved in the sample than other nucleic acid types, such as, e.g., hnRNA or mRNA. Nevertheless, the invention also contemplates the detection of mRNA or cDNA (e.g., by corresponding RT-PCT assays), or plasmid-derived DNA, where applicable.

The present method thus preferably employs amplification using primers pairs designed to specifically hybridise within and amplify corresponding amplicons from within nucleic acids the presence or absence of which in the sample need to be detected, such as, preferably, nucleic acids comprising or consisting of those listed under a)-u) above, as a means to detect the presence or absence of the said nucleic acids in the sample.

In this respect, the present inventors realised that if material of a transgenic plant event has been exposed to one or more downstream processing steps, e.g., as described above, the nucleic acids, such as the genomic DNA thereof, may be fragmented. Therefore, to increase the chances of the respective amplicons to be representatively amplified from so-fragmented DNA, the invention also teaches to advantageously reduce the size of the amplicons.

Accordingly, in preferred embodiments, the amplicons are less than about 300 bp, e.g., less than 280 bp, less than 260 bp, less than 240 bp, or less than 220 bp, more preferably less than about 200 bp, e.g., less than 190 bp, less than 180 bp, less than 170 bp or less than 160 bp, even more preferably less than about 150 bp, e.g., less than 140 bp, less than 130 bp, less than 120 bp or less than 110 bp, yet more preferably less than about 100 bp, and still more preferably less than about 90 bp, e.g. about 85 bp, about 80 bp, about 75 bp, about 70 bp, about 65 bp, about 60 bp, about 55 bp or about 50 bp.

In further preferred embodiments, the amplicons are between about 50 bp and about 150 bp, between about 50 bp and about 100 bp, preferably between about 50 bp and about 90 bp, to more preferably between about 60 bp and about 80 bp, and yet more preferably between about 65 bp and about 75 bp.

As explained, the above methods detect particular nucleic acids, preferably genomic DNA, in a sample. It can be appreciated that some robust detection protocols, e.g., some PCR protocols, might be performed on samples without prior purification or enrichment of their constituent nucleic acids. On the other hand, the detections of the invention may be performed more consistently if nucleic acids, such as preferably genomic DNA, are first enriched or isolated from the sample. Methods for isolation of nucleic acids, such as genomic DNA, from samples, particularly samples comprising plant material, are long-established in the art and include methods based on, by example and not limitation, organic solvent extraction (e.g., phenol-chloroform extraction) and ethanol or isopropyl alcohol precipitation; binding to ion-exchange resins; caesium chloride density separation; spin-column chromatography, magnetic separation, etc. (see, e.g., Milligan 1992. Plant DNA isolation. pp 59-88 in Hoelzel, ed. Molecular genetic analysis of populations: a practical approach. IRL Press, Oxford, UK).

Quality of so-isolated DNA can be assessed, e.g., by gel electrophoresis and/or by measuring the $A_{260}/A_{280}$ absorbance ratio. Preferably, the $A_{260}/A_{280}$ ratio for nucleic acids used in the detection methods of the invention can be between 1.6 and 2.3, more preferably between 1.6 and 2.0, even more preferably between 1.7 and 1.9, yet more preferably between 1.75 and 1.85 and most preferably about 1.8. Quantity of so-isolated DNA may be assessed, e.g., by measuring absorbance $A_{260}$ (Sambrook 1989), or preferably using PicoGreen™ or SYBR Green I fluorochromes (Ahn et al. 1996. Nucleic Acids Res 24: 2623-5; Schneeberger et al. 1995. PCR Methods Appl 4: 234-8).

In a preferred embodiment, preparation of nucleic acid material, particularly genomic DNA, for use in the methods of the invention may also entail fragmentation to obtain lower average sizes of the nucleic acid fragments, such as, e.g., using enzymatic digestion or sonication as known in the art. Preferable average length of the so-fragmented nucleic acids may be between 200 and 2000 bp, more preferably between 300 and 1500 bp, even more preferably between 500 and 1000 bp, e.g., about 500, about 600, about 700, about 800 about 900 or about 1000 bp.

The above methods thus detect the presence or absence of select nucleic acids in a sample, preferably using detection systems and protocols as described heretofore. As used herein, the "presence" of a given nucleic acid in a sample is generally concluded when the signal intensity value (signal quantity) obtained for that nucleic acid using a suitable detection assay (e.g., fluorescent signal, chemiluminescent signal, enzymatic reaction signal, etc.) in the sample is greater, preferably statistically significantly greater, than that in a negative control.

A negative control does not contain the nucleic acid being assayed, but can advantageously be comparable to the sample in other respects, preferably most other respects, e.g., in the type and quantity of plant material contained therein, in downstream processing steps to which the material has been exposed, etc.

Preferably, the detection methods of the invention may be performed on nucleic acids, more preferably on genomic DNA, isolated from the sample (see above). In such instance, the negative control may consist essentially of isolated nucleic acids, not comprising the nucleic acid subject to detection. Preferably, the detection method would then employ the same or about the same quantity of isolated nucleic acids from both the sample and, for reference, the negative control. Also preferably, the purity and/or quality of nucleic acids isolated from the sample and from the negative control may also be the same or about the same; further preferably, the same isolation method may be used for isolating nucleic acids from both the sample and the negative control.

In the above situations, the presence of a given nucleic acid in a sample may be preferably concluded when the signal intensity value (signal quantity) obtained for that nucleic acid in the sample is at least 2× greater than that in the negative control, e.g., at least 3× or at least 4× greater, more preferably at least 5× greater, e.g., at least 6× greater, at least 7× greater, at least 8× greater or at least 9× greater, even more preferably at least 10× greater, e.g., at least 15× greater, yet more preferably at least 20× greater, e.g., at least 30× greater or at least 40× greater, still more preferably at least 50× greater, e.g., at least 100× greater, at least 200× greater, at least 300× greater, at least 400× greater, at least 500× greater, at least 1000× greater or even greater than the signal in the negative control.

Hence, when the signal value (signal quantity) obtained for the assayed nucleic acid in the sample is not greater (e.g., is same, about same or lower) than the signal value obtained for the assayed nucleic acid in the negative control, or preferably is not greater by the above recited preferred multiples, the "absence" of the said nucleic acid in the sample can be generally concluded.

In preferred embodiments, the presence or absence in the sample of a nucleic acid of interest is evaluated by real-time amplification, preferably real-time PCR. In these systems, a common measure used to express the quantity of the template for a given nucleic acid in a sample is the $C_t$ value. Briefly, the $C_t$ value states the cycle number at which the fluorescence attributable to the accruing amplification product ($\Delta R_n$) passes through an arbitrary threshold fluorescence value, the latter set above the baseline fluorescence but within the exponential phase of amplification (i.e., within the portion which would appear linear on a log 2 plot of the fluorescence vs. cycle # data).

Accordingly, in real-time amplification, the presence of a given nucleic acid in a sample may be generally concluded when $C_t$ of the sample ("SAM $C_t$") is lower than $C_t$ of a negative control ("NC $C_t$"); and may be preferably concluded when SAM $C_t \leq$ (NC $C_t$-1), e.g., SAM $C_t \leq$ (NC $C_t$-2), SAM $C_t \leq$ (NC $C_t$-3) or SAM $C_t \leq$ (NC $C_t$-4), more preferably when SAM $C_t \leq$ (NC $C_t$-5), e.g., SAM $C_t \leq$ (NC $C_t$-6), SAM $C_t \leq$ (NC $C_t$-7), SAM $C_t \leq$ (NC $C_t$-8) or SAM $C_t \leq$ (NC $C_t$-9), even more preferably when SAM $C_t \leq$ (NC $C_t$-10), e.g., SAM $C_t \leq$ (NC $C_t$-11), SAM $C_t \leq$ (NC $C_t$-12), SAM $C_t \leq$ (NC $C_t$-13), SAM $C_t \leq$ (NC $C_t$-13) or SAM $C_t \leq$ (NC $C_t$-14), yet more preferably when SAM $C_t \leq$ (NC $C_t$-15), e.g., SAM $C_t \leq$ (NC $C_t$-16), SAM $C_t \leq$ (NC $C_t$-17), SAM $C_t \leq$ (NC $C_t$-18) or SAM $C_t \leq$ (NC $C_t$-19), still more preferably when SAM $C_t \leq$ (NC $C_t$-20), e.g., SAM $C_t \leq$ (NC $C_t$-25), SAM $C_t \leq$ (NC $C_t$-30) or SAM $C_t \leq$ (NC $C_t$-35).

Hence, in real-time amplification, when SAM $C_t$ is not lower (e.g., is same, about same or greater) than NC $C_t$, or preferably is not lower by the preferred differentials recited above, the "absence" of the said nucleic acid in the sample can be generally concluded.

As noted above, in real-time amplification systems which do not employ sequence specific probes (e.g., when amplification product is detected using sequence non-specific DNA dyes such as, e.g., SYBR Green I), the specificity of the amplification product can be verified by performing a melting curve analysis and determining the Tm. Presence of specific amplification product can be concluded when the observed Tm is identical or substantially identical (preferably within an interval of ±3° C., more preferably ±2° C., yet more preferably ±1° C., even more preferably ±0.5° C., and still more preferably ±0.2° C. or ±0.1° C.) to the calculated and/or experimentally determined melting temperature of the expected amplicon.

Moreover, specific amplification can be preferably concluded when the melting curve analysis of the amplification product displays a single Tm. Alternatively or in addition, specific amplification can be preferably concluded when the amplification product displays a single, expected size upon gel electrophoresis. However, the appearance of non-specific amplification product(s) might to some extent be tolerable in practice, preferably if such non-specific amplification product(s) would constitute less than 50%, more preferably less than 40%, even more preferably less than 30%, still more preferably less than 20%, yet more preferably less than 10%, further more preferably less than 5%, even more preferably less than 2% and most preferably less than 1%, e.g., less than 0.5% or less than 0.1%, of the total quantity (w/w) of the amplification product. Such non-specific amplification product(s) may be observed, e.g., by appearance of one or more additional Tm peaks in the melting curve analysis and/or appearance of one or more additional product sizes upon gel electrophoresis.

In a further development of the invention, it is noted that amplicons amplified using the same primer set on nucleic acids originating from different evens may show distinct Tm values, presumably due to some differences in the sequence between such amplicons. By means of example and not limitation, amplicons amplified using primer set SEQ ID NO: 11 and 12 (Table 4) on Bt11 and Bt176 show such a difference in their Tm. Accordingly, the observed Tm value may serve as a further distinguishing information to use in the method of the invention, such that an even more detailed indication of the presence or absence of nucleic acids from such particular events is obtained.

Alternatively or in addition, in a further variation, a particular nucleic acid may be amplifiable using a particular primer set from one or more events, while the same primer would not amplify the corresponding nucleic acid in one or more other events, presumably due to some sequence differences in the primer binding sites. While such situation would necessitate the use of two or more primer sets to amplify the corresponding nucleic acid from different events (and may in that respect be less advantageous than choosing a primer set that amplifies the nucleic acid from all plant events of interest), it may give the advantage of providing additional information about the presence or absence of nucleic acids from particular events in the sample. For example, the Cry1Ab nucleic acid may be advantageously detected from MON810 using the primer set SEQ ID NO: 30 and 31 and from Bt11 and Bt176 using the primer set SEQ ID NO: 11 and 12 (Table 4).

A skilled person can appreciate that amplification reactions, e.g., PCR, may give rise to a non-specific, "primer-dimer" by-product. Such primer-dimer products can be typically readily distinguished from the specific amplification product(s) by their different, most often smaller, size and/or Tm. Hence, a skilled person would be able to recognise and minimise the effect of such artifacts on the analysis of the amplification reaction. The preferred primers of the invention, such as those listed in Tables 1 and 4, have been designed to minimise the effect of primer dimer.

A further issue is the sensitivity of the detection methods used in the present invention, which may be advantageously expressed as "limit of detection" (LOD) thereof, referring herein to the lowest amount or concentration of an analyte (herein of a given nucleic acid to be detected) in a sample which can be reliably detected, although not necessarily quantified. "Reliably detected" as used herein means that samples containing the LOD amount or concentration of the analyte will give a positive outcome in ≥50% of repeated detections, preferably in ≥60%, more preferably in ≥70%, even more preferably in ≥80%, yet more preferably in ≥90%, and most preferably in ≥95% or even in ≥99% of repeated detections.

Preferably, LOD of detection methods suitable for use in the invention, expressed herein as the LOD copy number of a given nucleic acid of interest in a sample subjected to the detection, may be 10 000 or less, e.g., 9 000 or less, 8 000 or less, 7 000 or less or 6 000 or less, more preferably 5 000 or less, e.g., 4 000 or less, 3 000 or less or 2 000 or less, even more preferably 1 000 or less, e.g., 900 or less, 800 or less, 700 or less or 600 or less, yet more preferably 500 or less, e.g., 400 or less, 300 or less or 200 or less, still more preferably 100 or less, e.g., 90 or less, 80 or less, 70 or less or 60 or less, and most preferably 50 or less, with exemplary preferred embodiments including 40 or less, 30 or less, 20 or less or 10 or less, such as, e.g., 1, 2, 3, 4, 5, 6, 7, 8 or 9. The preferred primers of the invention, such as those listed in Tables 1 and 4, have been designed to achieve particularly high sensitivity (low LOD).

As used herein, the term "maize" refers to *Zea mays*, preferably *Zea mays* ssp. *mays*, and includes all plant varieties that can be bred with maize, including wild maize species; the terms "rapeseed", "oilseed rape" or "canola" refer interchangeably to *Brassica napus*, and include all plant varieties that can be bred with rapeseed, including wild rapeseed species; the terms "soya", "soy", "soya bean" or "soybean" refer interchangeably to *Glycine max*, and include all plant varieties that can be bred with soybean, including wild soybean species; the term "rice" refers to *Oryza sativa*, including, without limitation, ssp. *indica* and *japonica*, and to includes all plant varieties that can be bred with rice, including wild rice species; the term "sugar beet" refers to *Beta vulgaris*, and include all plant varieties that can be bred with sugar beet, including wild sugar beet species; the term "cotton" refers to *Gossypium* species, preferably *Gossypium hirsutum*, and includes all plant varieties that can be bred with cotton, including wild cotton species; the term "potato" refers to *Solanum tuberosum*, and includes all plant varieties that can be bred with potato, including wild potato species.

Transgenic plant events are referred to herein by their designations as commonly employed in the art and familiar to a skilled person. Nevertheless, by means of further assistance, Table 2 below summarises further information sufficient for specific identification of recited events.

TABLE 2

Identification of transgenic plant events.

| Event | Company | Host taxon | Unique ID (UI) |
|---|---|---|---|
| Bt176 | Syngenta | Zea mays | SYN-EV176-9 |
| Bt11 | Syngenta | Zea mays | SYN-BTØ11-1 |
| MON810 | Monsanto | Zea mays | MON-ØØ81Ø-6 |
| MON863 | Monsanto | Zea mays | MON-ØØ863-5 |
| TC1507 | Pioneer Hi-Bred/Dow AgroScience | Zea mays | DAS-Ø15Ø7-1 |
| NK603 | Monsanto | Zea mays | MON-ØØ6Ø3-6 |
| T25 | Bayer CropScience | Zea mays | ACS-ZMØØ3-2 |
| GA21 | Monsanto | Zea mays | MON-ØØØ21-9 |
| DAS-59122 | Dow AgroSciences/ Pioneer Hi-Bred | Zea mays | DAS-DAS-59122-7 |
| MIR604 | Syngenta Seeds | Zea mays | SYN-IR6Ø4-5 |
| LY038 | Renessen LLC/ Monsanto | Zea mays | REN-ØØØ38-3 |
| MON88017 | Monsanto | Zea mays | MON88Ø17-3 |
| Topas 19/2 | Bayer CropScience | Brassica napus | ACS-BNØØ7-1 |
| MS1 | Bayer CropScience | Brassica napus | ACS-BNØØ4-7 |
| RF1 | Bayer CropScience | Brassica napus | ACS-BNØØ1-4 |
| RF2 | Bayer CropScience | Brassica napus | ACS-BNØØ2-5 |
| RF3 | Bayer CropScience | Brassica napus | ACS-BNØØ3-6 |
| MS8 | Bayer CropScience | Brassica napus | ACS-BNØØ5-8 |
| GT73 | Monsanto | Brassica napus | MON-ØØØ73-7 |
| T45 | Bayer CropScience | Brassica napus | ACS-BNØØ8-2 |
| Liberator pHoe6/Ac | Bayer CropScience | Brassica napus | ACS-BN010-4 |
| GS40/90pHoe6/Ac | Bayer CropScience | Brassica napus | ACS-BN010-4 |
| MS1/RF1 | Bayer CropScience | Brassica napus | ACS-BNØØ4-7 × ACS-BNØØ1-4 |
| MS1/RF2 | Bayer CropScience | Brassica napus | ACS-BNØØ4-7 × ACS-BNØØ2-5 |
| MS8/RF3 | Bayer CropScience | Brassica napus | ACS-BNØØ5-8 × ACS-BNØØ3-6 |
| OXY235 | Bayer CropScience | Brassica napus | ACS-BNØ11-5 |
| MON 40-3-2 | Monsanto | Glycine max | MON-Ø4Ø32-6 |
| MON89788 | Monsanto | Glycine max | MON-89788-1 |
| A2704-12 | Bayer CropScience | Glycine max | ACS-GMØØ5-3 |
| A5547-127 | Bayer CropScience | Glycine max | ACS-GMØØ6-4 |
| LL62 | Bayer CropScience | Oryza sativa | ACS-OSØØ2-5 |
| LL06 | Bayer CropScience | Oryza sativa | ACS-OSØØ1-4 |
| T120-7 | Bayer CropScience | Beta vulgaris | ACS-BVØØ1-3 |
| H7-1 | KWS SAAT AG/ Monsanto | Beta vulgaris | KM-ØØØH71-4 |
| A5-15 | DANISCO Seed; DLF Trifolium A/S; Monsanto | Beta vulgaris | DLF-0A515-7 |
| LL cotton 25 | Bayer CropScience | Gossypium hirsutum | ACS-GHØØ1-3 |
| MON 1445 | Monsanto | Gossypium hirsutum | MON-Ø1445-2 |
| MON 531 | Monsanto | Gossypium hirsutum | MON-ØØ531-6 |
| MON 15985 | Monsanto | Gossypium hirsutum | MON-15985-7 |
| EH-92-527-1 | Amylogen HB (BASF Plant Science | Solanum tuberosum | BPS-25271-9 |

The above listed unique identifiers (UI) represent a system for unique classification of transgenic plant events set in place by the Organisation for Economic Co-operation and Development (OECD) and described in its publications ENV/JM/MONO(2002)7: "OECD Guidance for the Designation of a Unique Identifier for Transgenic Plants", of Oct. 20, 2004, and ENV/JM/MONO(2002)7/REV1 of Nov. 7, 2006. The said unique identifiers are used, recognised and assigned internationally, including in Europe (see, e.g., Commission Regulation (EC) No 65/2004 of Jan. 14, 2004 establishing a system for the development and assignment of unique identifiers for genetically modified organisms).

Detailed information regarding the above and further transgenic plant events of interest, such as, e.g., information on host taxons, transforming constructs, inserted sequences, etc. can be accessed through publicly available portals of various regulatory authorities including, e.g., the OECD BioTrack Product Database, the US FDA, the European Community Register of GM Food and Feed, the Agbios database, or the EC GMO Compass database, as well as in scientific literature, etc. A skilled person is well-aware and can use such database sources.

In addition, event-specific detection methods and construct-specific detection methods (e.g., see Codex Alimentarium) are available and allow to unambiguously distinguish the above and further events. For example, the European Community Reference Laboratory (CRL) lists validated methods for event-specific detection, as provided by manufacturers, described in scientific literature or developed and by the CRL itself.

As noted above, the invention allows to conclude the presence or absence in a sample of material derived from select events, crosses thereof, or related events thereof.

The term "crosses thereof" in this context refers to progeny obtained by one or more subsequent crossings of two or more compatible events (i.e., events capable of being crossed, particularly events belonging to the same taxon), such that the said resulting progeny comprises transgenic inserts from the two or more parental events being crossed.

The term "related events thereof" in this context refers to events that have been generated by introducing into the same taxons the same transforming constructs as that of the respective recited events, but are nevertheless distinct from the recited events, e.g., may typically differ in the number and/or site of genomic integrations of the transforming construct. Often, such events may themselves be subject to authorisation. In other instances, such related events may be present as unwanted contaminants. Hence, by detecting genetic elements from within the transforming constructs, the method of the invention advantageously allows to detect such events.

As noted above, the methods of the invention involve detection of the presence or absence in samples of one or more nucleic acids comprising or consisting of those listed under a)-u) as defined above.

In this respect, the recitation "a nucleic acid derived from and specific for" a given taxon, such as defined for nucleic acids listed under a) "Zm", b) "Bn", c) "Gm", o) "Or", p) "Bv", q) "Gs", and t) "St", means that the said nucleic acid in the sample originates from the genetic material, preferably genomic DNA, of the said given taxon and is not present— and thus would not be detectable using the chosen detection method—in the genetic material originating from other taxons, such as the remaining taxons listed above. By means of example and not limitation, said nucleic acid derived from the given taxon may either have no homologues in other taxons or its homologues in other taxons may have sufficiently distinct sequences such that they would not be detected by the chosen detection method. For example, at a site of detection, e.g., at a site to which of a probe or one or more amplification primers would hybridise within the given nucleic acid, such homologues may show less than 100% sequence identity, preferably less than 95%, even more preferably less than 90%, yet more preferably less than 85%, still more preferably less than 80%, and most preferably less than 75%, in preferred exemplary embodiments less than 70%, less than 65%, less than 60%, less than 55% or less than 50% sequence identity with the given nucleic acid.

Further, the term nucleic acid "derived from" as used especially in a)-u) means that the said nucleic acids originate from their respective taxons, genetic elements, genes, open reading frame, etc., albeit they—as found in the sample—may in part structurally differ therefrom.

For instance, downstream processing of plant material may cause alterations in nucleic acid (e.g., DNA) structure, and perhaps most notably may cause fragmentation thereof. In addition, sometimes functional fragments or variants of full-length elements may be used in transgenic plants. Accordingly, nucleic acids "derived from" those recited under a)-u) above may be, e.g., fragments thereof, insofar such fragments allow for their specific attribution to the original nucleic acids. For example, such fragments may include at least 15 continuous bp of the sequence from which they are derived, preferably at least 20 continuous bp, e.g., at least 30 or at least 40 continuous bp, more preferably at least 50 continuous bp, e.g., at least 60 or at least 70 continuous bp, even more preferably at least 80 continuous bp, e.g., at least 90 continuous bp, yet more preferably at least 100 continuous bp, e.g., at least 150 continuous bp, still more preferably at least 200 continuous bp, e.g., at least 300 continuous bp, at least 400 continuous bp or at least 500 continuous bp or more and may even include full-length elements.

Other nucleic acids modifications expected from downstream processing of plant material, e.g., partial deamination, etc., are also contemplated under the term "derived from".

In a preferred embodiment, the nucleic acid a) "Zm" is derived from the endogenous alcohol dehydrogenase I gene (adh-1) of *Zea mays*. An exemplary but non-limiting sequence of the adh-1 gene of *Zea mays* is found under accession number AF123535.1 in the GenBank database.

In a further preferred embodiment, the nucleic acid b) "Bn" is derived from the endogenous acetyl-CoA carboxylase gene (acc) or the endogenous cruciferin gene of *Brassica napus*. An exemplary but non-limiting sequence of the acc gene of *Brassica napus* is found under accession number X77576.1 in the GenBank database; an exemplary sequence of the cruciferin gene of *Brassica napus* is found under accession number X14555.1 in the GenBank database.

In a further preferred embodiment, the nucleic acid c) "Gm" is derived from the endogenous lectin gene (lec) of *Glycine max*. An exemplary but non-limiting sequence of the lec gene of *Glycine max* is found under accession number K00821.1 in the GenBank database.

In a further preferred embodiment, the nucleic acid o) "Or" is derived from the endogenous phospholipase D gene (pld) of *Oryza sativa*. An exemplary but non-limiting sequence of the pld gene of *Oryza sativa* is found under accession number AB001919.

In a preferred embodiment, the nucleic acid p) "Bv" is derived from the endogenous Glutamine synthetase gene (GluA3) of *Beta vulgaris*. An exemplary but non-limiting sequence of the GluA3 gene of *Beta vulgaris* is found under accession number AY026353.1 in the GenBank database.

In a preferred embodiment, the nucleic acid q) "Gs" is derived from the endogenous sinopsis arabidopsis homolog 7 gene (sah-7) of *Gossypium*. An exemplary but non-limiting sequence of the sah-7 gene of *Gossypium* is found under accession number AY117067 (Authors: Senchina et al. 2003. Mol Biol Evol 20 (4): 633-643) in the GenBank database.

In a preferred embodiment, the nucleic acid t) "St" is derived from the endogenous UDP-glucose pyrophosphorylase gene (UGPase) of *Solanum tuberosum*. An exemplary but non-limiting sequence of the UGPase gene of *Solanum tuberosum* is found under accession number U20345 in the GenBank database.

In a further preferred embodiment, the generic plant-derived nucleic acid is derived from the endogenous chloroplastic RBCL gene (rbcl) of *Zea mays*. An exemplary but non-limiting sequence of the rbcl gene of *Zea mays* is found under accession number Z11973.1 in the GenBank database.

A skilled person would be capable of designing and verifying specific probes or primer pairs from the above cited sequences for use in the detection steps of the present method.

The references to sequence elements and genes recited in this specification for the nucleic acids listed under d)-n), r), s) and u) are known to a skilled person in the field of genetic modification of plants. Hence, a skilled person understands to what sequences these designations refer and would as well appreciate the level of alterations to these sequences that is common in generation of transgenic plants.

In an embodiment, the nucleic acid present in a transgenic event may include the open reading frame or a functional part thereof (i.e., a part achieving the desired effect in the transgenic plant) of the genes recited herein, esp. the genes listed under f)-n), r), s) and u) above.

Nevertheless, by means of further clarification and not limitation, we here under list exemplary sequences for the particular genes and elements referred to under d)-n), r), s) and u), and an exemplary generic plant-derived nucleic acid:

| Sequence element/gene | GenBank accession number |
|---|---|
| CMV p35S promoter | V00140 (entire CAMV genome) |
| NOS terminator | V00087.1 |
| Cry1Ab ORF | AF465640 |
| bar gene ORF | AY346130.1 |
| pat gene ORF | DQ156557.1 |
| EPSPS gene ORF | AY125353.1 |
| modified Cry3A gene ORF | AR836206.1 |
| Glb1 promoter | CS155614.1 |
| Cry3Bb1 gene ORF | CS410008.1 |
| Bxn gene ORF | E01313.1 |
| Cry1Ac gene ORF | EF094884.1 |
| Cry2Ab2 gene ORF | DQ361266.1 |
| Gbss gene ORF | X58453.1 |
| *Zea mays* chloroplast rbcL gene | Z11973.1 |

It shall be appreciated that nucleic acids actually present in transgenic plant events can comprise sequences which may differ to some extent from the above exemplary sequences. For example, such differences may include base deletions, additions and/or substitutions, truncations (e.g., inclusion of functional fragments), fusions to other elements (e.g., fusion to membrane transport or organelle sorting signals), etc.

The actual sequences of the above and other elements found in the transgenic events have been in many instances determined and are accessible via GenBank and other sequence databases. Accordingly, sequence alignments shall be performed in order to identify regions within the above nucleic acids most suitable for derivation of probes or amplicons therefrom.

Hence, a probe or an amplicon (and corresponding primer set) can be advantageously derived from a portions of each of the above nucleic acids which is found in most transgenic events and/or which shows the highest sequence identity between the various transgenic events. Such probe or primer pair will increase the chance of detection of that particular nucleic acid from various transgenic events. A skilled person can follow this instruction to perform the necessary sequence alignments.

As set out in the Summary section, the invention also provides an advantageous manner of concluding the potential presence or absence of material from one or more transgenic plant events of interest to be used in step (2) of the above methods. In particular, the results obtained for the sample in step (1) are represented as a set $G_{SAM}$ symbolizing a collection of those nucleic acids, chosen from those comprising or consisting of the ones listed under a)-u) above, that were detected as present in the sample; and comparing the said set $G_{SAM}$ with one or more sets of interest $G_X$ representing the individual events to be evaluated. The sets of interest $G_X$ consist of, i.e., represent a collection of, those nucleic acids chosen from ones comprising or consisting of those listed under a)-u) above that are found in the respective events and thus would be detected in step (1) (in the extent to which said step (1) detects the presence of said nucleic acids) if the sample contained material derived from the respective events, or a cross involving such, or a related event.

The following Table 3 lists which nucleic acids of those listed under a)-u) above are present in particular events of interest:

TABLE 3

Features of events.

| Event | a | b | c | d | e | f | g | h | i | j | k | l | m | n | o | p | q | r | s | t | u |
|---|---|---|---|---|---|---|---|---|---|---|---|---|---|---|---|---|---|---|---|---|---|
| Bt176 | + | − | − | + | − | + | + | − | − | − | − | − | − | − | − | − | − | − | − | − | − |
| Bt11 | + | − | − | + | + | + | − | + | − | − | − | − | − | − | − | − | − | − | − | − | − |
| Bt10 | + | − | − | + | + | + | − | + | − | − | − | − | − | − | − | − | − | − | − | − | − |
| MON810 | + | − | − | + | + | + | − | − | − | − | − | − | − | − | − | − | − | − | − | − | − |
| MON863 | + | − | − | + | + | − | − | − | − | − | − | − | − | − | − | − | − | − | − | − | − |
| TC1507 | + | − | − | + | − | − | − | + | − | − | − | − | − | − | − | − | − | − | − | − | − |
| NK603 | + | − | − | + | + | − | − | − | + | − | − | − | − | − | − | − | − | − | − | − | − |
| T25 | + | − | − | + | − | − | − | + | − | − | − | − | − | − | − | − | − | − | − | − | − |
| GA21 | + | − | − | − | + | − | − | − | − | − | − | − | − | − | − | − | − | − | − | − | − |
| DAS-59122 | + | − | − | + | − | − | + | − | − | − | − | − | − | − | − | − | − | − | − | − | − |
| MIR604 | + | − | − | − | + | − | − | − | − | + | − | − | − | − | − | − | − | − | − | − | − |
| LY038 | + | − | − | + | + | − | − | − | − | − | + | + | − | − | − | − | − | − | − | − | − |
| MON88017 | + | − | − | + | + | − | − | − | + | − | − | + | − | − | − | − | − | − | − | − | − |
| Topas 19/2 | − | + | − | + | − | − | + | − | − | − | − | − | − | − | − | − | − | − | − | − | − |
| MS1 | − | + | − | + | − | + | − | − | − | − | − | − | − | − | − | − | − | − | − | − | − |
| RF1 | − | + | − | + | − | + | − | − | − | − | − | − | − | − | − | − | − | − | − | − | − |
| RF2 | − | + | − | + | − | + | − | − | − | − | − | − | − | − | − | − | − | − | − | − | − |
| RF3 | − | + | − | + | − | + | − | − | − | − | − | − | − | − | − | − | − | − | − | − | − |
| MS8 | − | + | − | + | − | + | − | − | − | − | − | − | − | − | − | − | − | − | − | − | − |

TABLE 3-continued

Features of events.

| Event | a | b | c | d | e | f | g | h | i | j | k | l | m | n | o | p | q | r | s | t | u |
|---|---|---|---|---|---|---|---|---|---|---|---|---|---|---|---|---|---|---|---|---|---|
| GT73 | − | + | − | − | − | − | − | − | + | − | − | − | − | − | − | − | − | − | − | − | − |
| T45 | − | + | − | + | − | − | − | + | − | − | − | − | − | − | − | − | − | − | − | − | − |
| Liberator pHoe6/Ac | − | + | − | + | − | − | − | + | − | − | − | − | − | − | − | − | − | − | − | − | − |
| GS40/90pHoe6/Ac | − | + | − | + | − | − | − | + | − | − | − | − | − | − | − | − | − | − | − | − | − |
| MS1/RF1 | − | + | − | − | + | − | + | − | − | − | − | − | − | − | − | − | − | − | − | − | − |
| MS1/RF2 | − | + | − | − | + | − | + | − | − | − | − | − | − | − | − | − | − | − | − | − | − |
| MS8/RF3 | − | + | − | − | + | − | + | − | − | − | − | − | − | − | − | − | − | − | − | − | − |
| OXY235 | − | + | − | + | − | − | − | − | − | − | − | − | − | − | + | − | − | − | − | − | − |
| MON 40-3-2 | − | − | + | + | + | − | − | − | + | − | − | − | − | − | − | − | − | − | − | − | − |
| MON89788 | − | − | + | − | − | − | − | − | + | − | − | − | − | − | − | − | − | − | − | − | − |
| A2704-12 | − | − | + | + | − | − | − | + | − | − | − | − | − | − | − | − | − | − | − | − | − |
| A5547-127 | − | − | + | + | − | − | − | + | − | − | − | − | − | − | − | − | − | − | − | − | − |
| LL62 | − | − | − | + | − | − | + | − | − | − | − | − | − | − | − | + | − | − | − | − | − |
| LL06 | − | − | − | + | − | − | + | − | − | − | − | − | − | − | − | + | − | − | − | − | − |
| LL601 | − | − | − | + | + | − | + | − | − | − | − | − | − | − | − | + | − | − | − | − | − |
| T120-7 | − | − | − | + | − | − | − | + | − | − | − | − | − | − | − | − | + | − | − | − | − |
| H7-1 | − | − | − | + | − | − | − | − | + | − | − | − | − | − | − | − | + | − | − | − | − |
| A5-15 | − | − | − | + | + | − | − | + | − | − | − | − | − | − | − | − | + | − | − | − | − |
| LL cotton 25 | − | − | − | + | + | − | + | − | − | − | − | − | − | − | − | − | − | + | − | − | − |
| MON 1445 | − | − | − | + | + | − | − | + | − | − | − | − | − | − | − | − | − | + | − | − | − |
| MON 531 | − | − | − | + | + | − | − | − | − | − | − | − | − | − | − | − | − | + | + | − | − |
| MON 15985 | − | − | − | + | + | − | − | − | − | − | − | − | − | − | − | − | − | + | + | + | − |
| EH-92-527-1 | − | − | − | − | + | − | − | − | − | − | − | − | − | − | − | − | − | − | − | + | + |

As already explained:

- if $G_X$ equals $G_{SAM}$ ($G_X=G_{SAM}$), then material derived from the transgenic plant event X, or from a cross thereof, or from an event related thereto, is potentially present in the sample;
- if $G_X$ is a proper subset of $G_{SAM}$ ($G_X \subset G_{SAM}$), then material derived from transgenic plant event X, or from a cross thereof, or from an event related thereto, is potentially present in the sample;
- if $G_X$ does not equal $G_{SAM}$ and $G_X$ is not a proper subset of $G_{SAM}$, ($G_X \neq G_{SAM}$ and $G_X \not\subset G_{SAM}$), then material derived from transgenic plant event X, or from a cross thereof, or from an event related thereto, is absent from the sample.

In a further preferred embodiment, if $G_X$ equals $G_{SAM}$ and if no one set or the sum of two or more sets representing events (in particular, sets representing events chosen from a group comprising or consisting of: $G_{Bt176}$, $G_{Bt11}$, $G_{Bt10}$, $G_{MON810}$, $G_{MON863}$, $G_{TC1507}$, $G_{NK603}$, $G_{T25}$, $G_{GA21}$, $G_{DAS-59122}$, $G_{MIR604}$, $G_{LY038}$, $G_{MON88017}$, $G_{Topas\ 19/2}$, $G_{MS1}$, $G_{RF1}$, $G_{RF2}$, $G_{MS1/RF1}$, $G_{MS1/RF2}$, $G_{MS8}$, $G_{RF3}$, $G_{MS8/RF3}$, $G_{T45}$, $G_{Liberator\ pHoe6/Ac}$, $G_{GS40/90pHoe6/Ac}$, $G_{OXY235}$, $G_{MON40-3-2}$, $G_{MON89788}$, $G_{A2704-12}$, $G_{A6547-127}$, $G_{LL62}$, $G_{LL06}$, $G_{LL601}$, $G_{T120-7}$, $G_{H7-1}$, $G_{A5-15}$, $G_{LL\ cotton\ 25}$, $G_{MON1445}$, $G_{MON531}$, $G_{MON15985}$ and $G_{EH92-527-1}$) other than $G_X$ equals $G_X$, then material derived from transgenic plant event X or from a cross thereof, or from an event related thereto, is present in the sample.

In a further development of this manner of evaluation, nucleic acids comprising or consisting of those listed under a)-u) above are assigned respective unique values. Hence, the set $G_{SAM}$ is then assigned a value "$VG_{SAM}$" being a multiple of the unique values assigned to those nucleic acids detected in step (1) as being present in the sample; and a set of interest $G_X$ is assigned a value "$VG_X$" being a multiple of the unique values assigned to those nucleic acids chosen from ones comprising or consisting of those listed under a)-u) above that are found in the said event and thus would be detected in step (1).

Accordingly, in a preferred example, nucleic acids "Zm", "Bn", "Gm", "p35S", "tNOS", "Cry1Ab", "PAT/bar", "PAT/pat", "CP4-EPSPS", "mCry3A", "cordap A", "Glb1", "Cry3Bb1", "Bxn", "Or", "Bv", "Gs", "Cry1Ac", "Cry2ab2", "St" and "Gbss" would be assigned respective unique values "$V_{Zm}$", "$V_{Bn}$", "$V_{Gm}$", "$V_{p35S}$", "$V_{tNOS}$", "$V_{Cry1Ab}$", "$V_{PAT/bar}$", "$V_{PAT/pat}$", "$V_{CP4-EPSPS}$", "$V_{mCry3A}$", "$V_{cordap\ A}$", "$V_{Glb1}$", "$V_{Cry3Bb1}$", "$V_{Bxn}$", "$V_{Or}$", "$V_{Bv}$", "$V_{Gs}$", "$V_{Cry1Ac}$", "$V_{Cry2ab2}$", "$V_{St}$" and "$V_{Gbss}$";

and each set of interest $G_X$ would be assigned a respective value "$VG_X$" chosen from values of the group comprising or consisting of values "$VG_{Bt176}$", "$VG_{Bt11}$", "$VG_{Bt10}$", "$VG_{MON810}$", "$VG_{MON863}$", "$VG_{TC1507}$", "$VG_{NK603}$", "$VG_{T25}$", "$VG_{GA21}$", "$VG_{DAS-59122}$", "$VG_{MIR604}$", "$VG_{LY038}$", "$VG_{MON88017}$", "$VG_{Topas\ 19/2}$", "$VG_{MS1}$", "$VG_{RF1}$", "$VG_{RF2}$", "$VG_{MS1/RF1}$", "$VG_{MS1/RF2}$", "$VG_{MS8}$", "$VG_{RF3}$", "$VG_{MS8/RF3}$", "$VG_{GT73}$", "$VG_{T45}$", "$VG_{Liberator\ pHoe6/Ac}$", "$VG_{GS40/90pHoe6/Ac}$", "$VG_{OXY235}$", "$VG_{MON40-3-2}$", "$VG_{MON89788}$", "$VG_{A2704-12}$", "$VG_{A5547-127}$", "$VG_{LL62}$", "$VG_{LL06}$", "$VG_{LL601}$", "$VG_{T120-7}$", "$VG_{H7-1}$", "$VG_{A5-15}$", "$VG_{LL\ cotton\ 25}$", "$VG_{MON1445}$", "$VG_{MON531}$", "$VG_{MON15985}$" or "$VG_{EH92-527-1}$", wherein:

$VG_{Bt176} = V_{Zm} \times V_{p35S} \times V_{Cry1Ab} \times V_{PAT/bar}$, $VG_{Bt11} = V_{Zm} \times V_{p35S} \times V_{tNOS} \times V_{Cry1Ab} \times V_{PAT/pat}$, $VG_{Bt10} = V_{Zm} \times V_{p35S} \times V_{tNOS} \times V_{Cry1Ab} \times V_{PAT/pat}$, $VG_{MON810} = V_{Zm} \times V_{p35S} \times V_{tNOS} \times V_{Cry1Ab}$, $VG_{MON863} = V_{Zm} \times V_{p35S} \times V_{tNOS}$, $VG_{TC1507} = V_{Zm} \times V_{p35S} \times V_{PAT/pat}$, $VG_{NK603} = V_{Zm} \times V_{p35S} \times V_{tNOS} \times V_{CP4-EPSPS}$, $VG_{T25} = V_{Zm} \times V_{p35S} \times V_{PAT/pat}$, $VG_{GA21} = V_{Zm} \times V_{tNOS}$, $VG_{DAS-59122} = V_{Zm} \times V_{p35S} \times V_{PAT/bar}$, $VG_{MIR604} = V_{Zm} \times V_{tNOS} \times V_{mCry3A}$, $VG_{LY038} = V_{Zm} \times V_{p35S} \times V_{tNOS} \times V_{cordapA} \times V_{Glb1}$, $VG_{MON88017} = V_{Zm} \times V_{p35S} \times V_{tNOS} \times V_{CP4-EPSP} \times V_{Cry3Bb1}$, $VG_{Topas\ 19/2} = V_{Bn} \times V_{p35S} \times V_{PAT/pat}$, $VG_{MS1} = V_{Bn} \times V_{tNOS} \times V_{PAT/bar}$, $VG_{RF1} = V_{Bn} \times V_{tNOS} \times V_{PAT/bar}$, $VG_{RF2} = V_{Bn} \times V_{tNOS} \times V_{PAT/bar}$, $VG_{MS8} = V_{Bn} \times V_{tNOS} \times V_{PAT/bar}$, $VG_{RF3} = V_{Bn} \times V_{tNOS} \times V_{PAT/bar}$, $VG_{MS1/RF1} = V_{Bn} \times V_{tNOS} \times V_{PAT/bar}$, $VG_{MS1/RF2} = V_{Bn} \times V_{tNOS} \times V_{PAT/bar}$,
$VG_{MS8/RF3} = V_{Bn} \times V_{tNOS} \times V_{PAT/bar}$,
$VG_{GT73} = V_{Bn} \times V_{CP4-EPSPS}$,
$VG_{T45} = V_{Bn} \times V_{p35S} \times V_{PAT/pat}$,
$VG_{Liberator\ pHoe6/Ac} = V_{Bn} \times V_{p35S} \times V_{PAT/pat}$,
$VG_{GS40/90pHoe6/Ac} = V_{Bn} \times V_{p35S} \times V_{PAT/pat}$,
$VG_{OXY235} = V_{Bn} \times V_{p35S} \times V_{Bxn}$,
$VG_{MON40-3-2} = V_{Gm} \times V_{p35S} \times V_{tNOS} \times V_{CP4-EPSPS}$,
$VG_{MON89788} = V_{Gm} \times V_{CP4-EPSPS}$,
$VG_{A2704-12} = V_{Gm} \times V_{p35S} \times V_{PAT/pat}$,
$VG_{A5547-127} = V_{Gm} \times V_{p35S} \times V_{PAT/pat}$,
$VG_{LL62} = V_{Or} \times V_{p35S} \times V_{PAT/bar}$,
$VG_{LL06} = V_{Or} \times V_{p35S} \times V_{PAT/bar}$,
$VG_{LL601} = V_{Or} \times V_{p35S} \times V_{tNOS} \times V_{PAT/bar}$,
$VG_{T120-7} = V_{Bv} \times V_{p35S} \times V_{PAT/pat}$,
$VG_{H7-1} = V_{Bv} \times V_{p35S} \times V_{CP4-EPSPS}$,
$VG_{A5-15} = V_{Bv} \times V_{p35S} \times V_{tNOS} \times V_{CP4-EPSPS}$,
$VG_{LL\ cotton\ 25} = V_{Gs} \times V_{p35S} \times V_{tNOS} \times V_{PAT/bar}$,
$VG_{MON1445} = V_{Gs} \times V_{p35S} \times V_{tNOS} \times V_{CP4-EPSPS}$,
$VG_{MON531} = V_{Gs} \times V_{p35S} \times V_{tNOS} \times V_{Cry1Ac}$,
$VG_{MON15985} = V_{Gs} \times V_{p35S} \times V_{tNOS} \times V_{Cry1Ac} \times V_{Cry1Ac}$,
or $VG_{EH92-527-1} = V_{St} \times V_{tNOS} \times V_{Gbss}$.

Note that insofar the methods do not test the presence of all nucleic acids under a)-u), the above values shall be defined in terms of those nucleic acids the presence of which is effectively tested. By means of example and not limitation, where the presence of nucleic acids listed under j)-n), r) s) and u) as defined above, which correspond to specific traits in addition to those defined under d)-i), is not tested, then the values corresponding to several events may be defined in a narrower manner, in particular: maize event values $VG_{MIR604} = V_{Zm} \times V_{tNOS}$, $VG_{LY038} = V_{Zm} \times V_{p35S} \times V_{tNOS}$, $VG_{MON88017} = V_{Zm} \times V_{p35S} \times V_{tNOS} \times V_{CP4-EPSP}$; oilseed rape event value $VG_{OXY235} = V_{Bn} \times V_{p35S}$, cotton event values $VG_{MON531} = V_{Gs} \times V_{p35S} \times V_{tNOS}$, $VG_{MON15985} = V_{Gs} \times V_{p35S} \times V_{tNOS}$; and potato event value $VG_{EH92-527-1} = V_{St} \times V_{tNOS}$.

Consequently, step (iii) of this embodiment would comprise performing for each set of interest $G_X$ logical operations:

if $VG_{SAM}/VG_X$ equals 1, then material derived from transgenic plant event X or from a cross thereof, or from an event related thereto, is potentially present in the sample;

if $VG_{SAM}/VG_X$ equals one value or a multiple of two or more values chosen from a group comprising or consisting of values $V_{Zm}$, $V_{Bn}$, $V_{Gm}$, $V_{p35S}$, $V_{tNOS}$, $V_{Cry1Ab}$, $V_{PAT/bar}$, $V_{PAT/pat}$, $V_{CP4-EPSPS}$, $V_{mCry3A}$, $V_{cordap\ A}$, $V_{Glb1}$, $V_{Cry3Bb1}$, $V_{Bxn}$, $V_{Or}$, $V_{Bv}$, $V_{Gs}$, $V_{Cry1Ac}$, $V_{Cry2ab2}$, $V_{St}$ and $V_{Gbss}$, then material derived from transgenic plant event X or from a cross thereof, or from an event related thereto, is potentially present in the sample;

if $VG_{SAM}/VG_X$ does not equal 1 and does not equal one value or a multiple of two or more values chosen from a group comprising or consisting of values $V_{Zm}$, $V_{Bn}$, $V_{Gm}$, $V_{p35S}$, $V_{tNOS}$, $V_{Cry1Ab}$, $V_{PAT/bar}$, $V_{PAT/pat}$, $V_{CP4-EPSPS}$, $V_{mCry3A}$, $V_{cordap\ A}$, $V_{Glb1}$, $V_{Cry3Bb1}$, $V_{Bxn}$, $V_{Or}$, $V_{Bv}$, $V_{Gs}$, $V_{Cry1Ac}$, $V_{Cry2ab2}$, $V_{St}$ and $V_{Gbss}$, then material derived from transgenic plant event X or from a cross thereof, or from an event related thereto, is absent from the sample.

In a further preferred variant of the above embodiment, if $VG_{SAM}/VG_X$ equals 1, and if no one value or the multiple of two or more values of sets representing events (in particular, values chosen from a group comprising or consisting of: $VG_{Bt76}$, $VG_{Bt11}$, $VG_{Bt10}$, $VG_{MON810}$, $VG_{MON863}$, $VG_{TC1507}$, $VG_{NK603}$, $VG_{T25}$, $VG_{GA21}$, $VG_{DAS-59122}$, $VG_{MIR604}$, $VG_{LY038}$, $VG_{MON88017}$, $VG_{Topas\ 19/2}$, $VG_{MS1}$, $VG_{RF1}$, $VG_{RF2}$, $VG_{MS1/RF1}$, $VG_{MS1/RF2}$, $VG_{MS8}$, $VG_{RF3}$, $VG_{MS8/RF3}$, $VG_{GT73}$, $VG_{T45}$, $VG_{Liberator\ pHoe6/Ac}$, $VG_{GS40/90pHoe6/Ac}$, $VG_{OXY235}$, $VG_{MON40-3-2}$, $VG_{MON89788}$, $VG_{A2704-12}$, $VG_{A5547-127}$, $VG_{LL62}$, $VG_{LL06}$, $VG_{LL601}$, $VG_{T120-7}$, $VG_{H7-1}$, $VG_{A5-15}$, $VG_{LL\ cotton\ 25}$, $VG_{MON1445}$, $VG_{MON531}$, $VG_{MON15985}$ and $VG_{EH92-527-1}$) other than $VG_X$ equals $VG_X$, then material derived from transgenic plant event X or from a cross thereof, or from an event related thereto, is present in the sample.

In a further preferred embodiment, the unique values assigned to the nucleic acids comprising or consisting of those listed under a)-u), i.e., values chosen from the group comprising or consisting of $V_{Zm}$, $V_{Bn}$, $V_{Gm}$, $V_{p35S}$, $V_{tNOS}$, $V_{Cry1Ab}$, $V_{PAT/bar}$, $V_{PAT/pat}$, $V_{CP4-EPSPS}$, $V_{mCry3A}$, $V_{cordap\ A}$, $V_{Glb1}$, $V_{Cry3Bb1}$, $V_{Bxn}$, $V_{Or}$, $V_{Bv}$, $V_{Gs}$, $V_{Cry1Ac}$, $V_{Cry2ab2}$, $V_{St}$ and $V_{Gbss}$, are unique prime numbers, and the step (iii) comprises performing for each set of interest $G_X$ logical operations, if $VG_{SAM}/VG_X$ equals 1, then material derived from transgenic plant event X or from a cross thereof, or from an event related thereto, is potentially present in the sample;

if $VG_{SAM}/VG_X$ is an integer greater than 1, then material derived from transgenic plant event X or from a cross thereof, or from an event related thereto, is potentially present in the sample;

if $VG_{SAM}/VG_X$ is not an integer, then material derived from transgenic plant event X or from a cross thereof, or from an event related thereto, is absent from the sample.

The inventors realised that the use of prime numbers to represent the individual assayed traits (nucleic acids), as described in the foregoing paragraph, is particularly straightforward and advantageously streamlines and facilitates the analysis of the data.

In view thereof, the inventors also contemplate the general applicability of the herein explained data analysis method using prime numbers in other applications, such as, e.g., in the field of molecular biology or molecular medicine, etc. Hence, in one application, the method may be generally used for determining the composition of a sample, wherein said sample may contain two or more different events (the word event as used in this paragraph has a general meaning not limited to transgenic plant events) or material thereof, wherein each event is characterised by one or more features or traits (the words features and traits as used in this paragraph carry a general meaning not limited to, albeit preferably including, nucleic acids). Hence, the sample as well as each event can be represented as a product (i.e., operation "×") of unique prime values assigned to each of the tested features or traits, and the (potential) presence or the absence of said event or material thereof in said sample may be tested by dividing (i.e., operation "/") the value obtained for the sample by the value calculated and assigned to each individual event, and considering the result of said division as described above mutatis mutandis.

In a preferred embodiment, the above calculation steps of the method step (2) are carried out by a computing device, e.g., a calculator or a computer; and in further aspects the invention also contemplates a computing device performing the above calculations, a data carrier (e.g., a diskette, CD-ROM, etc.) comprising instructions for a programmable computing device to carry out the step (2) of the method of the invention, including the above calculations, a kit comprising such data carrier alongside one or more reagents also useful in the methods of the invention. Also, the invention contemplates a web-based application allowing for to performing the algorithm of step (2), optionally wherein information about events potentially present in the sample can be directly accessed in an associated database by means of an embedded hyperlink.

It shall be appreciated that the identifiers "$G_{SAM}$", "$G_X$", "$VG_{SAM}$", "$VG_X$", etc. used in the above description were arbitrarily chosen herein to represent the underlying concepts of inter alia sets and values, respectively, and that other identifiers (e.g., other letters, words or expressions) may be substituted to represent said sets and values.

As mentioned, the method of the invention may preferably evaluate the presence or absence of nucleic acids of interest, especially nucleic acids chosen from the group comprising or consisting of those listed under a)-u) above, using amplification and particularly PCR amplification of amplicons therefrom.

It can be appreciated that a skilled person may be in general capable of designing individual primer sets for specific amplification from known nucleic acid sequences.

Nevertheless, as already described, Table 1 lists particularly advantageous primer pairs that have been carefully designed by the inventors to provide numerous benefits when used in the present methodology. Moreover, Table 4 lists the primers of Table 1 and further includes additional primers and primer pairs which also perform very satisfactorily in the present method, albeit the primers of Table 1 remaining the prime choice of the inventors. These primer sets can advantageously achieve amplification from the respective nucleic acids as present in the relevant plant events and from variously processed plant material, and entail various advantages as described elsewhere in this specification.

TABLE 4

Primer sequences.

| Nucleic acid | Primers | | |
|---|---|---|---|
| "Zm"<br>(adh-1) | Fwd:<br>Rev: | 5' CgTCgTTTCCCATCTCTTCCTCC 3'<br>5' CCACTCCgAgACCCTCAgTC 3' | (SEQ ID NO: 1)<br>(SEQ ID NO: 2) |
| "Zm"<br>(adh-1) | Fwd:<br>Rev: | 5' TCTCTTCCTCCTTTAGAGCTACCACTA 3'<br>5' AATCGATCCAAAGCGAGATGA 3' | (SEQ ID NO: 56)<br>(SEQ ID NO: 57) |
| "Bn"<br>(ACC) | Fwd1:<br>Fwd2:<br>Rev: | 5' GAGAATGAGGAGGACCAAGCTC 3'<br>5' GGTGAGCTGTATAATCGAGCGA 3'<br>5' GGCGCAGCATCGGCT 3' | (SEQ ID NO: 4)<br>(SEQ ID NO: 79)<br>(SEQ ID NO: 3) |
| "Bn"<br>(cruciferin) | Fwd:<br>Rev: | 5' CAGCTCAACAGTTTCCAAACGA 3'<br>5' CGACCAGCCTCAGCCTTAAG 3' | (SEQ ID NO: 24)<br>(SEQ ID NO: 25) |
| "Gm"<br>(lectin) | Fwd:<br>Rev:<br>Rev': | 5' CATTACCTATgATgCCTCCACC 3'<br>5' AAgCACgTCATgCgATTC 3'<br>5' AAgCACgTCATgCgATTCC 3' | (SEQ ID NO: 5)<br>(SEQ ID NO: 6)<br>(SEQ ID NO: 49) |
| "Gm"<br>(lectin) (SLTM) | Fwd:<br>Rev': | 5' AACCGGTAGCGTTGCCAG 3'<br>5' AGCCCATCTGCAAGCCTTT 3' | (SEQ ID NO: 58)<br>(SEQ ID NO: 59) |
| "p35S"<br>(longer) | Fwd:<br>Rev: | 5'-GACAGTGGTCCCAAAGATGG-3'<br>5'-GTCTTGCGAAGGATAGTGGG-3' | (SEQ ID NO: 7)<br>(SEQ ID NO: 8) |
| "p35S"<br>(shorter) | Fwd:<br>Rev: | 5' AAAGCAAGTGGATTGATGTGATA 3'<br>5' GGGTCTTGCGAAGGATAGTG 3' | (SEQ ID NO: 60)<br>(SEQ ID NO: 61) |
| "tNOS"<br>("TNOS-D") | Fwd:<br>Rev: | 5'-GATTAGAGTCCCGCAATTATACATTTAA-3'<br>5'-TTATCCTAGKTTGCGCGCTATATTT-3' | (SEQ ID NO: 9)<br>(SEQ ID NO: 10) |
| "tNOS"<br>(TNOS-L) | Fwd:<br>Rev: | 5' CGTTCAAACATTTGGCAATAAAG 3'<br>5' AAATGTATAATTGCGGGACTCTAATC 3' | (SEQ ID NO: 28)<br>(SEQ ID NO: 29) |
| "Cry1Ab" | Fwd:<br>Rev: | 5'-ACCGGTTACACTCCCATCGA-3'<br>5'-CAGCACCTGGCACGAACTC-3' | (SEQ ID NO: 11)<br>(SEQ ID NO: 12) |
| "Cry1Ab" | Fwd:<br>Rev: | 5' GACATCATCTGGGGYATCTT 3'<br>5' GCGCTGTTCATGTCGTTGAA 3' | (SEQ ID NO: 30)<br>(SEQ ID NO: 31) |
| "Cry1Ab" | Fwd:<br>Rev: | 5' ACGCCTTCCTGGTGCAAA 3'<br>5' CCTGGTTCCTGGCGAACTC 3' | (SEQ ID NO: 47)<br>(SEQ ID NO: 48) |
| "PAT/bar" | Fwd:<br>Rev: | 5'-CGTCAACCACTACATCGAGACAA-3'<br>5'-GTCCACTCCTGCGGTTCCT-3' | (SEQ ID NO: 13)<br>(SEQ ID NO: 14) |
| "PAT/pat" | Fwd:<br>Rev: | 5'-CCGCGGTTTGTGATATCGTT-3'<br>5'-TCTTGCAACCTCTCTAGATCATCAA-3' | (SEQ ID NO: 15)<br>(SEQ ID NO: 16) |
| "CP4-EPSPS" | Fwd1:<br>Fwd1':<br>Fwd2:<br>Rev: | 5'-GGCTCTGAGCTTCGTCCTCCTAAGG-3'<br>5'-GGCTCTGAGCTTCGTCCTCTTAAGG-3'<br>5'-ATCAGTGGCTACAGCCTGCAT-3'<br>5'-GAATGCGGACGGTrCCGGAAAG-3' | (SEQ ID NO: 17)<br>(SEQ ID NO: 50)<br>(SEQ ID NO: 18)<br>(SEQ ID NO: 19) |
| "CP4-EPSPS" | Fwd:<br>Rev:<br>Rev 1:<br>Rev 2: | 5' GCATGCTTCACGGTGCAA 3'<br>5' GGACCTGTGGGAGATAGACTTGTC 3'<br>5' TGAAGGACCGGTGGGAGAT 3'<br>5' TGAAGGACCTGTGGGAGAT 3' | (SEQ ID NO: 22)<br>(SEQ ID NO: 23)<br>(SEQ ID NO: 62)<br>(SEQ ID NO: 63) |

TABLE 4-continued

Primer sequences.

| Nucleic acid | Primers | | |
|---|---|---|---|
| "Or" | Fwd: 5' GCTTAGGGAACAGGGAAGTAAAGTT 3' | (SEQ ID NO: 20) | |
| | Fwd': 5' GCTTAGGGAACAGGGAAGTAAAGT 3' | (SEQ ID NO: 51) | |
| | Rev: 5' CTTAGCATAGTCTGTGCCATCCA 3' | (SEQ ID NO: 21) | |
| "Bv" | Fwd: 5' GACCTCCATATTACTGPAAGGAAG 3' | (SEQ ID NO: 64) | |
| (GluA3) | Rev: 5' GAGTAATTGCTCCATCCTGTTCA 3' | (SEQ ID NO: 65) | |
| "Gs" | Fwd: 5' AGTTTGTAGGTTTTGATGTTACATTGAG 3' | (SEQ ID NO: 66) | |
| | Rev: 5' GCATCTTTGAACCGCCTACTG 3' | (SEQ ID NO: 67) | |
| "St" | Fwd: 5' GGACATGTGAAGAGACGGAGC 3' | (SEQ ID NO: 68) | |
| (UGPase) | Rev: 5' CCTACCTCTACCCCTCCGC 3' | (SEQ ID NO: 69) | |
| generic plant | Fwd: 5' AGGTCTAADGGRTAAGCTAC 3' | (SEQ ID NO: 26) | |
| (Rbcl) | Rev: 5' AGYCTTGATCGTTACAAAGG 3' | (SEQ ID NO: 27) | |

Where Table 4 includes more than one rows which concern amplification on a certain nucleic acid (such as, e.g., several rows for "Cry1Ab" and "CP4-EPSPS") by different primer sets, any one or more of said primer sets of said different rows of Table 4 can be used for amplification. Where Table 4 lists, within a single row, more than one forward and/or reverse primers for amplification on a certain nucleic acid (such as, e.g., for "Bn" (ACC), "Gm" (lectin) or "CP4-EPSPS"), any one or any combination of said forward primer(s) may be used in conjunction with any one or with any combination of said reverse primer(s) to obtain amplification.

In addition, the invention also provides variant primers that include one or more sequence variations vis-à-vis the primers listed in Table 4, such as, e.g., one or more deletion, insertion and/or substitution, insofar such primers/primer pairs can still achieve adequate amplification of their respective amplicons. Preferably, such variant primers would show at least 85%, more preferably at least 90%, even more preferably at least 95%, and yet more preferably at least 96%, at least 97%, at least 98% or at least 99% sequence identity to the primers listed in Table 4. Sequence alignments and determination of sequence identity can be done, e.g., using the Basic Local Alignment Search Tool (BLAST) originally described by Altschul et al. 1990 (J Mol Biol 215: 403-10), such as the "Blast 2 sequences" algorithm described by Tatusova and Madden 1999 (FEMS Microbiol Lett 174: 247-250).

In addition, the invention also contemplates nested primers and primer pairs suitable for amplification of amplicons from within those amplified from the respective nucleic acids using the primer pairs listed in any of Table 1 or Table 4.

The invention also contemplates derivatives, as described elsewhere in this specification, of the primers and primer pairs listed in any of Table 1 or Table 4.

Accordingly, the invention provides the primers and primer pairs listed in any of Table 1 or Table 4, as well as variants and derivatives thereof, optionally in any suitable combination of said primers and/or primer pairs or variants or derivatives thereof.

In a further aspect, the invention provides amplification products obtainable from the respective nucleic acids using the above primers and primer pairs, and particularly using primer pairs set out in any of Table 1 or Table 4 or variants or derivatives thereof. The said amplification products may be further processed, such as, e.g., isolated, cloned in suitable vectors or plasmids, transformed into recombinant hosts, e.g., suitable bacterial hosts such as E. coli, propagates therewith and isolated therefrom, sequenced, etc.

Advantageously, the said amplification products, preferably cloned and re-isolated, and possibly comprised in suitable plasmids or vectors, can be used as positive controls to verify the working of detection steps of the methods of the invention aimed at the detection of the respective nucleic acid in a sample. Alternatively or in addition, such amplification products (cloned or isolated) may be used as calibrators to determine the quantity of particular templates in a sample, e.g., in real-time PCR.

Accordingly, in a further aspect, the invention provides recombinant E. coli as deposited under the Budapest Treaty with the Belgian Coordinated Collections of Microorganisms (BCCM) on Jan. 10, 2007 under LMBP accession numbers LMBP 5452, LMBP 5453, LMBP 5454, LMBP 5455, LMBP 5456, LMBP 5457, LMBP 5458, LMBP 5459 and LMBP 5460, on Mar. 6, 2007 under LMBP accession number LMBP 5451, and on Apr. 19, 2007 under LMBP accession numbers LMBP 5587, LMBP 5588, LMBP 5589 and LMBP 5590.

The said recombinant E. coli comprise the amplification products obtained on template events using primer sets as listed in Table 5, cloned in the EcoRI sites of the pUC18 cloning vector MCS:

TABLE 5

| LMBP acc. # | Primer pair | Amplified on event | Insert sequenced (FIG. 1) |
|---|---|---|---|
| LMBP 5460 | SEQ ID NO: 7<br>SEQ ID NO: 8 | BT11 | SEQ ID NO: 34 |
| LMBP 5456 | SEQ ID NO: 9<br>SEQ ID NO: 10 | 40-3-2 | SEQ ID NO: 35 |
| LMBP 5452 | SEQ ID NO: 47<br>SEQ ID NO: 48 | MON810 | SEQ ID NO: 36 |
| LMBP 5453 | SEQ ID NO: 11<br>SEQ ID NO: 12 | Bt176 | SEQ ID NO: 37 |
| LMBP 5454 | SEQ ID NO: 11<br>SEQ ID NO: 12 | Bt11 | SEQ ID NO: 38 |
| LMBP 5457 | SEQ ID NO: 13<br>SEQ ID NO: 14 | BT176 | SEQ ID NO: 39 |
| LMBP 5455 | SEQ ID NO: 15<br>SEQ ID NO: 16 | BT11 | SEQ ID NO: 40 |
| LMBP 5458 | SEQ ID NO: 26<br>SEQ ID NO: 27 | Maize Bt11 | SEQ ID NO: 41 |
| LMBP 5459 | SEQ ID NO: 26<br>SEQ ID NO: 27 | OSR (oil seed rape) wt | SEQ ID NO: 42 |
| LMBP 5451 | SEQ ID NO: 28<br>SEQ ID NO: 29 | Bt11 | SEQ ID NO: 43 |

TABLE 5-continued

| LMBP acc. # | Primer pair | Amplified on event | Insert sequenced (FIG. 1) |
|---|---|---|---|
| LMBP 5587 | SEQ ID NO: 22 SEQ ID NO: 23 | RRS soybean | SEQ ID NO: 53 |
| LMBP 5588 | SEQ ID NO: 22 SEQ ID NO: 23 | GT 73 | SEQ ID NO: 54 |
| LMBP 5589 | SEQ ID NO: 24 SEQ ID NO: 25 | GT 73 | SEQ ID NO: 55 |
| LMBP 5590 | SEQ ID NO: 51 SEQ ID NO: 21 | WT rice | SEQ ID NO: 52 |

In addition to deposited plasmids and *E. coli* as listed in Table 5, the invention also provides further exemplary plasmids, such as, e.g., pUC18, containing inserts amplified using, e.g.:

the primer pair SEQ ID NO: 3 and 4 for the *Brassica* acc gene (exemplary insert sequence SEQ ID NO: 44 in FIG. 1 amplified on OSR wt);

CP4-EPSP primer pairs SEQ ID NO: 18 and 19, and SEQ ID NO: 50 and 19 (exemplary inserts amplified on, respectively, event 40-3-2 and event NK603, to obtain the respective exemplary insert sequences shown as SEQ ID NO: 45 and 46 in FIG. 1) (primer SEQ ID NO: 17 may also be used in conjunction with primer SEQ ID NO: 19; however, primer SEQ ID NO: 17 contains a sequence mismatch at nucleotide 20 compared to SEQ ID NO: 50 the latter being therefore more preferred);

the primer pair SEQ ID NO: 1 and 2 for the maize adh-1 gene (exemplary insert sequence SEQ ID NO: 32 in FIG. 1 amplified on wild-type maize);

the primer pairs SEQ ID NO: 5 and 49 for the soybean lectin gene (exemplary insert sequence SEQ ID NO: 33 in FIG. 1 amplified on wild-type soybean);

the primer pair SEQ ID NO: 56 and 57 for a shorter amplicon within the *Zea mays* adh-1 gene (exemplary insert sequence SEQ ID NO: 70 in FIG. 1);

the primer pair SEQ ID NO: 58 and 59 (SLTM) for a *Glycine max* lectin amplicon (exemplary insert sequence SEQ ID NO: 71 in FIG. 1);

the primer pair SEQ ID NO: 60 and 61 for a shorter amplicon within the p35S element (exemplary insert sequence SEQ ID NO: 72 in FIG. 1);

the primer pair SEQ ID NO: 64 and 65 for an amplicon within the *Beta vulgaris* GluA3 gene (exemplary insert sequence SEQ ID NO: 76 in FIG. 1);

the primer pair SEQ ID NO: 66 and 67 for an amplicon within the *Gossypium* sah-7 gene (exemplary insert sequence SEQ ID NO: 77 in FIG. 1);

the primer pair SEQ ID NO: 68 and 69 for an amplicon within the potato UGPase gene (exemplary insert sequence SEQ ID NO: 78 in FIG. 1);

the primer pair SEQ ID NO: 11 and 12 for an amplicon within the Cry1Ab trait (exemplary insert sequence SEQ ID NO: 73 in FIG. 1 amplified on MON 810 material);

the primer pair SEQ ID NO: 22 and 62 (RRS) or 22 and 63 (GT 73) for an amplicon within the CP4-EPSPS trait (exemplary insert sequence in FIG. 1: SEQ ID NO: 74 amplified on GT73 and SEQ ID NO: 75 amplified on RRS).

It is noted that due to the shorter size of the corresponding amplicon, the primer pair SEQ ID NO: 22 and 23 or SEQ ID NO: 22 in conjunction with any one or both of primers SEQ ID NO: 62 and 63, may be preferably used to amplify CP4-EPSPS from both unprocessed plant material (e.g., plant tissue or seeds) as well as processed material (e.g., food or feed), whereas the primer pairs SEQ ID NO: 18 and 19 or 50 and 19, which define a longer amplicon, can be preferably used on unprocessed material. Hence, the primer pair SEQ ID NO: 22 and 23 or SEQ ID NO: 22 in conjunction with any one or both of primers SEQ ID NO: 62 and 63, may be more preferred in the present methods and kits.

The invention further provides isolated recombinant plasmids obtainable from the recombinant *E. coli* bacteria listed in Table 5, as well as isolated inserts, preferably EcoRI inserts, thereof. The invention also provides any further recombinant microorganism transformed with the so-isolated plasmids.

A skilled person can also appreciate that the invention may too provide combinations of the said plasmids or inserts thereof, wherein the said combinations are representative of those nucleic acids that one intends to detect in a sample.

In addition, the invention also provides the use of recombinant plasmids or inserts as found in and obtainable from the bacteria of Table 5 or others explained above for use as positive controls and/or calibrators in the methods of the present invention. For example, such plasmids or inserts thereof may be included in the methods and kits of the invention in suitable quantities to also facilitate making a decision whether nucleic acid of one or more events is present in an amount which justifies further quantification, or is present under an acceptable threshold.

In a further development of the invention, it is also contemplated that any of the primers of the invention, such as in particular the primers listed in any of Table 1 or Table 4 or variants or derivatives thereof, may be used in a genome walking strategy to identify sequences adjacent to said primer in genomic DNA of an event. Similarly, it is contemplated that any primer designed on the basis of the sequence of any amplicon of the present invention, such as in particular any primer located within or overlapping with any of the amplicon sequences SEQ ID NO: 34 to SEQ ID NO: 78, or a variant or derivative of such primer, may be used in a genome walking strategy to identify sequences adjacent to said amplicon in genomic DNA of an event.

This aspect may be particularly useful where the present amplification methods produce an amplicon having characteristics (e.g., length, Tm or sequence) which cannot be unambiguously attributed to a particular event. In such situation, genome walking outside of the amplicon in question would provide additional sequence information about the event and thereby help to identify said event. In particularly preferred embodiments, the specific primer may be derived from p35 or tNOS amplicons.

In general, genome walking strategies are well-known in the art. Examples include inter alia inverse PCR or the vectorette method of Riley et al. 1990 (Nucleic Acids Res 18: 2887-90) commercialised as Universal Vectorette™ System (Sigma), as well as later simplifications thereof (see, e.g., Kilstrup & Kristiansen 2000. Nucleic Acids Res 28: e55).

In a particular embodiment, the inventors contemplate a two-step genome walking method. In a first amplification step a LUX™ (or otherwise) labelled primer of the invention is used together with a mixture of random primers (generally about 8 to 15 bp long), and preferably gradient PCR conditions of increasing stringency are used. The label on the primer allows to follow whether amplification involving the labelled primer is taking place. In a second amplification step, a nested PCR is performed using another nested primer from the amplicon, preferably also LUX™ or otherwise labelled, together with said random primers, and preferably at high-stringency PCR conditions. The label on the primer allows to follow whether amplification involving the labelled primer is taking place. Eventually, the so-obtained product is sequenced, thereby identifying the sequences adjacent to the amplicon.

In a further aspects, the invention provides kits of parts for performing the methods of the present invention, i.e., for examining a sample for the potential presence or absence of material derived from one or more transgenic plant events.

In an embodiment, a kit according to the invention can comprise probes suitable for detection of one or more or all nucleic acids listed under a)-u) above.

In an embodiment, a kit according to the invention can comprise primers, preferably primer pairs, suitable for amplification of amplicons from within one or more or all nucleic acids listed under a)-u) as defined above.

In another embodiment, the kit may comprise primers, preferably primer pairs, suitable for amplification of one, more than one, and preferably all of nucleic acids listed under a)-i) above.

In another embodiment, the kit may comprise primers, preferably primer pairs, suitable for amplification of one, more than one, and preferably all of nucleic acids listed under a)-i), o), p), q) and t) above.

In another embodiment, the kit may comprise primers, preferably primer pairs, suitable for amplification of one, more than one, or all of nucleic acids listed under a)-c) above and one, more than one or preferably all of nucleic acids listed under d)-i) above.

In another embodiment, the kit may comprise primers, preferably primer pairs, suitable for amplification of one, more than one, or all of nucleic acids listed under a)-c), o), p), q), t) above and one, more than one or preferably all of nucleic acids listed under d)-i) above.

In addition, the kit may also comprise primers or primer pairs for amplification of a generic plant sequence, as described elsewhere in this specification.

It shall be appreciated that primers and primer pairs for amplification on various nucleic acids taught herein may be included in variously designed kits, in accordance with the preference as to which transgenic events one wants to detect.

In a preferred embodiment, and taking into account the various selections of nucleic acids to be amplified as discussed in the preceding paragraphs, the kit may comprise one or more, or all primers, preferably one, more than one or all primer pairs, as defined in any of Table 1 or Table 4, or variants or derivatives thereof.

In a particularly preferred embodiment, one or both primers of any primers pair included in the kit may be labelled.

In another particularly preferred embodiment, any primer pair included in the kit may contain at least one, and usually one, primer labelled with a suitable fluorophore and designed to allow for real-time detection using the above-described LUX™ detection system.

In a further embodiment, the kit may also comprise amplification products, e.g., cloned and re-isolated and possibly comprised in suitable plasmids or vectors, that can be used as positive controls and/or calibrators in the methods of the invention, as explained above. For example, precisely measured quantities or dilutions of such amplification products, e.g., cloned and re-isolated and possibly comprised in suitable plasmids or vectors, may be provided for such purposes. As explained above, various combinations of such reagents may also be envisaged.

In a particular embodiment, the kit may comprise one, more than one or all of the *E. coli* organisms as listed in Table 5, and/or plasmids obtainable therefrom, and/or isolated inserts, preferably EcoRI inserts, of the said plasmids, or combinations hereof.

In a further embodiment, as already explained, the kit may also comprise a data carrier containing instructions for a programmable computing device to perform the actions of step (2) of the methods of the invention.

Understandably, such kits may comprise further components, such as components useful hybridisation, PCR, detection, etc. A skilled person will appreciate the potential use of such components.

In a preferred embodiment, the kit may comprise one or more reaction compartments, for example reaction compartments provided within a multi-well strip or plate (multi-well format), each compartment comprising a composition of all components necessary for a PCR amplification reaction (e.g., nucleotides, salts, thermostable polymerase, etc.), and including the desired one or more (where multiplexed) primer pairs as defined above, but not including template DNA. Accordingly, the PCR reaction could be started once the user introduces a sample DNA to be analysed to said composition. Optionally, to ensure stability, Taq or other thermostable polymerase may also be excluded from the composition (but may be separately included in the kit), and may need to be added by the user. Generally, the composition may be liquid, while especially for the purposes of shipment and storage it may be frozen. However, lyophilised compositions are also envisaged.

EXAMPLES

Example 1

Amplification Conditions for Select Primer Pairs Listed in Tables 1 and 4

SYBR Green detection real-time PCR was optimised for amplification of amplicons from nucleic acids "p35S", "tNOS", "Cry1Ab", "PAT/Bar", "PAT/pat" and "CP4-EPSPS" using respective primer pairs listed in Tables 1 and 4.

DNA was isolated from events containing (positive control) or lacking (negative control) these nucleic acids, including events Bt11, Bt176, MON810, MON40-3-2, TC1507, NK603, MS8/RF3 (see Table 5), using CTAB isolation from leaf tissue material.

PCR reactions contained SYBR Green PCR Master Mix (Diagenode, ref: GMO-GS2X-A300) 1×, Forward primer 250 nM, Reverse primer 250 nM, Template DNA 50 ng in total volume of 20 µl. PCR cycling involved Step 1: 1×[50° C., 120 sec]; Step 2: 1×[95° C. 600 sec]; and Step 3: 40×[95° C. 15 sec, 60° C. 60 sec] with fluorescence acquisition. Applied Biosystems Prism 7700 was used. Melting curve analysis was done at gradient from 50° C. to 95° C. over 1200 sec.

For all primer pairs, specific amplification products were obtained as shown by a single specific Tm and single band on agarose gel electrophoresis. The assays had low LOD:
RBCL: primers SEQ ID NO: 26 and SEQ ID NO: 27; Tm=76.5° C.; size=95 bp; LOD=±0.039 ng target DNA
*Zea mays* ADH (longer amplicon): primers SEQ ID NO: 1 and SEQ ID NO: 2; Tm=79.5° C.; size=138 bp; LOD=±0.016 ng target DNA (±6 haploid genomes)
*Zea mays* ADH (shorter amplicon): primers SEQ ID NO: 56 and SEQ ID NO: 57; Tm=75.5° C.; size=83 bp; LOD=±0.016 ng target DNA (±6 haploid genomes)
Oilseed rape ACC: primers SEQ ID NO: 79 and SEQ ID NO: 3; Tm=79° C.; size=103 bp; LOD=±0.05 ng target DNA (±20 haploid genomes)

Oilseed rape cruciferin: primers SEQ ID NO: 24 and SEQ ID NO: 25; Tm=80° C.; size=85 bp; LOD=±0.015 ng target DNA (±12 haploid genomes)

Soybean lectin (longer amplicon): primers SEQ ID NO: 5 and SEQ ID NO: 49; Tm=81.5° C.; size=178 bp; LOD=±0.016 ng target DNA (±13 haploid genomes)

Soybean (lectin): primers SEQ ID NO: 58 and SEQ ID NO: 59 (SLTM); Tm=79.5° C.; size=81 bp; LOD=±0.063 ng target DNA (±50 haploid genomes)

Rice PLD: primers SEQ ID NO: 20 and SEQ ID NO: 21; Tm=76.5° C.; size=80 bp; LOD=±0.01 ng target DNA (±20 haploid genomes)

Sugar beet GluA3: primers SEQ ID NO: 64 and SEQ ID NO: 65; Tm=77° C.; size=118 bp; LOD=±0.01 ng target DNA (±13 haploid genomes)

Cotton SAH7: primers SEQ ID NO: 66 and SEQ ID NO: 67; Tm=75.5° C.; size=115 bp; LOD=±0.02 ng target DNA (±9 haploid genomes)

Potato UGPase: primers SEQ ID NO: 68 and SEQ ID NO: 69; Tm=81° C.; size=87 bp; LOD=±0.0002 ng target DNA p35S (longer amplicon): primers SEQ ID NO: 7 and SEQ ID NO: 8; Tm=80.5° C.; size=147 bp; LOD=±0.016 ng target DNA (±6 haploid genomes)

p35S (shorter amplicon): primers SEQ ID NO: 60 and SEQ ID NO: 61; Tm=76° C.; size=75 bp; LOD: RRS 100%±0.032 ng target DNA (±25 haploid genomes); NK603 5%±6.25 ng target DNA (±62.5 haploid genomes)

tNOS-L: primers SEQ ID NO: 28 and SEQ ID NO: 29; Tm=72° C.; size=172 bp; LOD=±0.03 ng target DNA (±25 haploid genomes)

tNOS-D: primers SEQ ID NO: 9 and SEQ ID NO: 10; Tm=72° C.; size=69 bp; LOD=±0.03 ng target DNA (±25 haploid genomes)

Cry1Ab: primers SEQ ID NO: 11 and SEQ ID NO: 12; Tm=78.5° C.; size=73 bp; LOD=±0.06 ng (±12 haploid genomes)

PAT/Bar: primers SEQ ID NO: 13 and SEQ ID NO: 14; Tm=80° C.; size=69 bp; LOD=±0.125 ng (±50 haploid genomes)

PAT/pat: primers SEQ ID NO: 15 and SEQ ID NO: 16; Tm=77° C.; size=109 bp; LOD=±0.03 ng (±12 haploid genomes)

CP4-EPSP: primers SEQ ID NO: 22, SEQ ID NO: 62 and SEQ ID NO: 63; Tm=80.5 or 84.5° C.; sizes=108 bp; LOD: NK603 5%±3.125 ng (±31 haploid genomes), RRS 100%±0.032 ng (±25 haploid genomes), GT73 100%±0.016 ng (±12 haploid genomes)

CP4-EPSP: primers SEQ ID NO: 17, SEQ ID NO: 18 and SEQ ID NO: 19; Tm=85° C.; sizes=94 bp or 124 bp; LOD=±0.03 ng (±25 haploid genomes)

Example 2

Exemplary Simplified Method According to the Invention

A hypothetical sample was made by adding of Bt176 DNA to unrelated carrier DNA. The sample was screened for the presence or absence of "p35S", "tNOS", "Cry1Ab", "PAT/Bar", "PAT/pat" and "CP4-EPSPS" using the real-time PCR methods of Example 1.

The present simplified method intends to conclude on the potential presence or absence in the sample of material derived from Bt176, Bt11 and NK603.

After testing, the sample is positive for p35S, Cry1Ab and Pat/Bar but not for the other tested nucleic acids. Hence, the sample can be represented as set $G_{SAM} \in \{p35S; Cry1Ab; Pat/bar\}$. In this exemplary assay (where the presence of Zea mays nucleic acids is not examined), the event Bt176 is represented by set $G_{Bt176} \in \{p35S; Cry1Ab; Pat/bar\}$, event Bt11 by set $G_{Bt11} \in \{p35S; tNOS; Cry1Ab; Pat/pat\}$ and event NK603 by set $G_{NK603} \in \{p35S; tNOS; CP4-EPSP\}$.

Accordingly, since $G_{Bt176} = G_{SAM}$, material from event Bt176 may be present in the sample. On the other hand, because $G_{Bt11} \neq G_{SAM}$ and $G_{Bt11} \not\subset G_{SAM}$, material from event Bt11 is not present in the sample. Similarly, because $G_{NK603} \neq G_{SAM}$ and $G_{NK603} \not\subset G_{SAM}$, material from event NK603 is not present in the sample.

In an alternative representation, "p35S", "tNOS", "Cry1Ab", "PAT/Bar", "PAT/pat" and "CP4-EPSPS" are assigned respective prime values $V_{p35S}=3$, $V_{tNOS}=5$, $V_{Cry1Ab}=7$, $V_{PAT/Bar}=11$, $V_{PAT/pat}=13$ and $V_{CP4-EPSPS}=17$.

Consequently, the set $G_{SAM}$ is assigned a value $VG_{SAM}$ being a multiple of the respective values assigned to nucleic acids detected therein, i.e., $VG_{SAM} = V_{p35S} \times V_{Cry1Ab} \times V_{PAT/Bar} = 231$. Moreover, the set $G_{Bt176}$ is assigned a value $VG_{Bt176}$ being a multiple of the values assigned to those of the tested nucleic acids that are found in the event Bt176, i.e., $VG_{Bt176} = V_{p35S} \times V_{Cry1Ab} \times V_{PAT/Bar} = 231$. Analogously, the set $G_{Bt11}$ is assigned a value $VG_{Bt11} = V_{p35S} \times V_{tNOS} \times V_{Cry1Ab} \times V_{PAT/Pat} = 1365$; and the set $G_{NK603}$ is assigned a value $VG_{NK603} = V_{p35S} \times V_{tNOS} \times V_{CP4-EPSP} = 255$.

Accordingly, because $VG_{SAM}/VG_{Bt176}=1$, material from event Bt176 may be present in the sample. On the other hand, because $VG_{SAM}/VG_{Bt11}=0.169$, i.e., is not 1 and not an integer greater than 1, material from event Bt11 is not present in the sample. Similarly, because $VG_{SAM}/VG_{NK603}=0.906$, i.e., is not 1 and not an integer greater than 1, material from event NK603 is not present in the sample.

Example 3

Exemplary Description of a Kit According to the Invention (96 Well Plate Setup)

Nucleic acids to be screened: "Zm", "Bn", "Gm", "p35S", "tNOS", "CP4-EPSPS", "Cry1Ab", "PAT/bar", "PAT/pat" as defined above using primer pairs as defined in Table 1 above, as well as generic plant gene amplified using primer pair SEQ ID NO: 26 and 27 (Table 4).

Optionally, such as on request, the kit may also include taxon markers for rice ("Or"), cotton ("Gs"), sugar beet ("Bv") and/or potato ("St"), using the corresponding primer pairs as defined in Table 1.

Operational Conditions of the SYBR Green Q-PCR Methods

Reagents: SYBR Green PCR Master Mix including the HS Taq-polymerase; primers 20 μM; nuclease-free water Equipment: ABI PRISM® 7700 Sequence Detection System, 7300 Real-Time PCR System, Laminar Flow, Pipettes 20, 200 et 1000 μl, Sterile, aerosol-resistant pipette tips, Optical 96-well reaction plates, Optical caps Protocol: The PCR is conducted in an ABI PRISM® 7700 Sequence Detection System or the 7300 Real-Time PCR System following the manufacturer's instructions. One general PCR program is used.

PCR Mix preparation: The PCR Mix contains all components of a PCR reaction except the DNA template. This operation is carried out in a laminar flow, which is only used for this kind of operation.

TABLE 6

Reaction mixture for Q-PCR screening

| Component | Final concentration | μl/reaction | X re-actions |
|---|---|---|---|
| SYBRGreen PCR Master Mix (2X) | 1X | 12.5 μl | |
| Forward Primer (20 μM) | 250 nM | 0.312 μl | |
| Reverse Primer (20 μM) | 250 nM | 0.312 μl | |
| Nuclease free water | | 6.876 μl | |
| Total volume: | | 20 μl | |

DNA preparation: The template DNA is extracted using a standard CTAB DNA extraction method and the DNA concentration is measured by picogreen fluorescence determination.
PCR Setup: The PCR setup is carried out in a laminar flow. The DNA templates and the PCR Mix are combined in different rooms.
PCR Run: The PCR will be conducted following the manufacturer's instructions as described in the User's Manual.
The Thermal Cycler Conditions are listed below in Table 7.

TABLE 7

Thermocycler running conditions

| Step | Stage | T ° C. | Time (sec.) | Acquisition | Cycles |
|---|---|---|---|---|---|
| 1 | UNG | 50° C. | 120" | no | 1x |
| 2 | Taq activation | 95° C. | 600" | no | 1x |
| 3 | Amplification Denaturing | 95° C. | 15" | no | 40x |
|   | Annealing & Extension | 60° C. | 60" | Measure | |
| 4 | Melting | 50° C. to 95° C. | 1200" | Measure | 1x |

Subsequently a "melting curve" analysis is performed using a standard program (eg gradual melting from 50° C. to 95° C. and monitoring the fluorescence decrease)
GMO-Screening 96 Well Plate Set Up for Food/Feed Products
Below is described the setup including all general food/feed markers, the rice marker (detection of unauthorized rice events) and the CAMV Reverse Transcriptase marker (absence of CaMV control).
96-Plate Set Up:

It would be technically foreseen that the sample wells can be opened sequentially (e.g. first the positive controls, then the samples, and last the NTC and negative controls).
Ct values and Tm values for each well are recorded and used in the decision analysis. for GM-set determination present in the respective samples.
Note that in principle also each row could be produced separately in an alternative set up (whereby increased flexibility for the customer is achieved).

Example 4 p35S, tNOS Multiplex PCR

The present example shows exemplary multiplex PCR amplification of the p35S and tNOS amplicons, wherein detection is made by SYBR Green and the amplification products are distinguished on the basis of a difference in their melting temperatures (Tm).
Primer Pairs Used (20 μM):
p35S: SEQ ID NO: 60 and 61
tNOS: SEQ ID NO: 9 and 10
Template (50 ng): Roundup Ready Soybean (RRS) 100% (double positive control)
PCR Program: 95° C. 10', (95° C. 15", 60° C. 1')×40 cycles
Melting program: 50° C. to 95° C. in 20'
Multiplexing of PCR methods p35S and tNOS in SYBR Green is possible since both amplicons are distinguishable thank to there different Tm (see FIG. 2). So it is possible to get information with one PCR on the presence of two different targets that are p35S and tNOS.

Example 5

Additional Multiplexing Possibilities when Using SYBR Green

Experiments analogous to those of example 4 have further defined the feasibility of the following multiplexing combinations:
1. Maize adh-1 (SEQ ID NO: 56 and 57) with soybean SLTM (SEQ ID NO: 58 and 59)
2. Maize adh-1 (SEQ ID NO: 56 and 57) with oilseed rape cruciferin (SEQ ID NO: 24 and 25)

| Plant | Gm | Zm | Bn | Or | p35S | tNos | CP4 | Cry1Ab | PAT/pat | PAT/bar | CRT |
|---|---|---|---|---|---|---|---|---|---|---|---|
| + | + | + | + | + | + | + | + | + | + | + | + |
| − | − | − | − | − | − | − | − | − | − | − | − |
| NTC | NTC | NTC | NTC | NTC | NTC | NTC | NTC | NTC | NTC | NTC | NTC |
| Sample 1 A | Sample 1 A | Sample 1 A | Sample 1 A | Sample 1 A | Sample 1 A | Sample 1 A | Sample 1 A | Sample 1 A | Sample 1 A | Sample 1 A | Sample 1 A |
| Sample 1 B | Sample 1 B | Sample 1 B | Sample 1 B | Sample 1 B | Sample 1 B | Sample 1 B | Sample 1 B | Sample 1 B | Sample 1 B | Sample 1 B | Sample 1 B |
| Sample 2 A | Sample 2 A | Sample 2 A | Sample 2 A | Sample 2 A | Sample 2 A | Sample 2 A | Sample 2 A | Sample 2 A | Sample 2 A | Sample 2 A | Sample 2 A |
| Sample 2 B | Sample 2 B | Sample 2 B | Sample 2 B | Sample 2 B | Sample 2 B | Sample 2 B | Sample 2 B | Sample 2 B | Sample 2 B | Sample 2 B | Sample 2 B |

Positive controls (+) would be the corresponding amplicons (plasmids or inserts) as described herein in particular in Table 5 amplicons at a certain copy-number (e.g. 100 copies/well)

3. Soybean SLTM (SEQ ID NO: 58 and 59) with cotton sah-7 (SEQ ID NO: 66 and 67)
4. Cotton sah-7 (SEQ ID NO: 66 and 67) with oilseed rape cruciferin (SEQ ID NO: 24 and 25)

Example 6

Parameters of Real-Time PCR Using the Primers of the Invention

Figure 3:
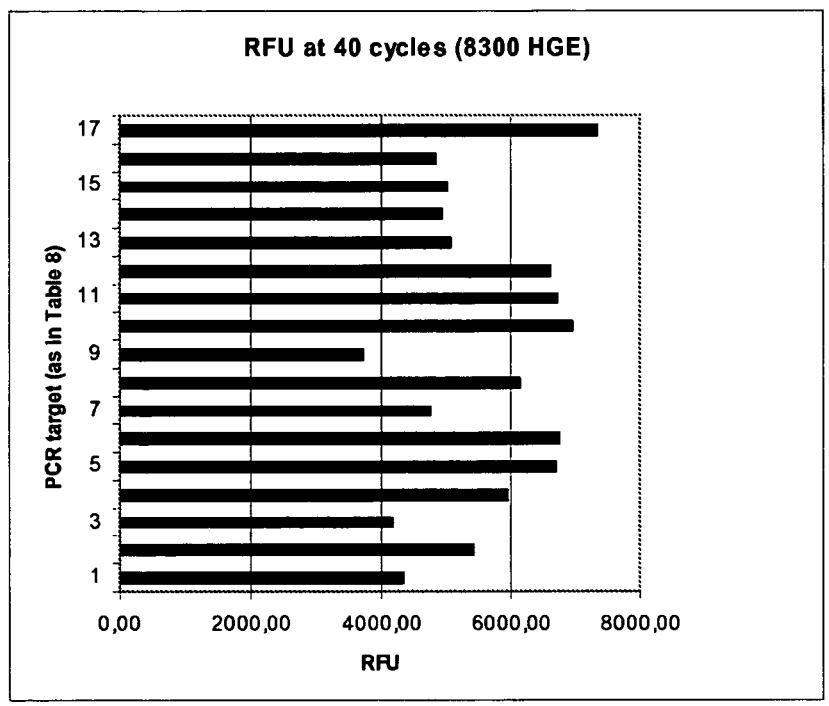
FIG. 3 provides graphical representation of the data using +/−8300 template copies as listed in Table 8.

Reactions using conditions and primers as defined in example 1 have been performed on a defined copy number of reference plasmids containing the respective amplicon inserts, and relative fluorescence (RFU) following 40 cycles (i.e., approaching or having reached the plateau) has been determined. The results in Table 8 (the results using +/−8300 template copies are also graphically represented in FIG. 3) show that the present methods and primers are capable of generating RFU values at plateau of at least 2500, which lie within a 3-fold margin.

TABLE 8

| | PCR target (Primers used: SEQ ID NO Fwd + Rev) | Plasmid template | Mean RFU 40 cycles with 1000 copies plasmids template | Mean RFU 40 cycles with +/− 8300 copies plasmids template | Amplicon size |
|---|---|---|---|---|---|
| 1 | RbcL (26 + 27) | RbcL OSR Wt | 2581.58 | 4369.51 | 95 |
| 2 | ADH longer (1 + 2) | ADH long | 4248.58 | 5447.4 | 135 |
| 3 | ADH shorter (56 + 57) | ADH alt | 2434.16 | 4210.28 | 84 |
| 4 | Lectin longer (5 + 49) | Lec Long | 3854.97 | 5969.65 | 178 |
| 5 | Lectin SLTM (58 + 59) | SLTM | 5943.98 | 6713.95 | 74 |
| 6 | Cru770 (24 + 25) | Cru770 | 4614.59 | 6768.95 | 85 |
| 7 | p35S longer (7 + 8) | p35S long | 3490.22 | 4792.49 | 147 |
| 8 | p35S shorter (60 + 61) | p35S short | 3963.27 | 6173.37 | 75 |
| 9 | tNOS-D (9 + 10) | tNOS-D | 2339.11 | 3731.95 | 69 |
| 10 | CryIAb (11 + 12) | CryIAb Bt11 | 4299.47 | 6973.77 | 73 |
| 11 | CryIAb (11 + 12) | CryIAb MON810 | 3957.05 | 6759.2 | 73 |
| 12 | CryIAb (11 + 12) | CryIAb Bt11 and CryIAb MON810 | 4028.97 | 6641.04 | 73 |
| 13 | CP4 (22 + 62 + 63) | CP4-RRS | 3235.24 | 5098.82 | 108 |
| 14 | CP4 (22 + 62 + 63) | CP4-GT73 | 2641.86 | 4968.28 | 108 |
| 15 | CP4 (22 + 62 + 63) | CP4-RRS and CP4-GT73 | 3157.24 | 5034.91 | 108 |
| 16 | Pat-Pat (15 + 16) | Pat-Pat | 2299.71 | 4875.61 | 109 |
| 17 | Pat-Bar (13 + 14) | Pat-Bar | 4839.79 | 7370.7 | 69 |
| | | Average: | 3642.93 | 5641.17 | |
| | | Standard Dev: | 1011.93 | 1106.76 | |
| | | Median: | 3854.97 | 5447.40 | |
| | | Minimum: | 2299.71 | 3731.95 | |
| | | Maximum: | 5943.98 | 7370.7 | |

The invention claimed is:

1. A method to examine a sample for the presence or absence of material derived from one or more transgenic plant events comprising the steps of:

(1) detecting the presence or absence in the sample of nucleic acids comprising:

one, more than one or all of nucleic acids chosen from:
  a) "Zm": a nucleic acid derived from and specific for *Zea mays* taxon, preferably *Zea mays* ssp. *mays*,
  b) "Bn": a nucleic acid derived from and specific for *Brassica napus* taxon,
  c) "Gm": a nucleic acid derived from and specific for *Glycine max* taxon,
  o) "Or": a nucleic acid derived from and specific for *Oryza sativa* taxon,
  p) "Bv": a nucleic acid derived from and specific for *Beta vulgaris* taxon,
  q) "Gs": a nucleic acid derived from and specific for *Gossypium* taxon, and
  t) "St": a nucleic acid derived from and specific for *Solanum tuberosum* taxon; and all of nucleic acids d)-i):
  d) "p35S": a nucleic acid derived from the 35S promoter of Cauliflower Mosaic Virus,
  e) "tNOS": a nucleic acid derived from the 3' terminator of the *Agrobacterium tumefaciens* nopaline synthetase gene,
  f) "Cry1Ab": a nucleic acid derived from the crystal protein gene Cry1Ab of *Bacillus thuringiensis*,
  g) "PAT/bar": a nucleic acid derived from the phosphinothricin acetyltransferase (PAT) gene bar of *Streptomyces hygroscopicus*,
  h) "PAT/pat": a nucleic acid derived from the phosphinothricin acetyltransferase (PAT) gene pat of *Streptomyces viridochromogenes*, and
  i) "CP4-EPSPS": a nucleic acid derived from the 5-Enol-pyruvylshikimate-3-phosphate synthase EPSPS gene from *Agrobacterium* sp. CP4; and (2) concluding the presence or absence in the sample of material derived from one or more transgenic plant events chosen from the group comprising: events Bt176, Bt11, Bt10, MON810, MON863, TC1507, NK603, T25, GA21, DAS-59122, MIR604, LY038, MON88017, crosses thereof, and related events thereof; events Topas 19/2, MS1, RF1, RF2, RF3, MS8, GT73, T45, Liberator pHoe6/Ac, GS40/90pHoe6/Ac, OXY235, crosses thereof including MS1/RF1, MS1/RF2, MS8/RF3, and related events thereof; events MON 40-3-2, MON89788, A2704-12, A5547-127, crosses thereof, and related events thereof, events LL62, LL06 and LL601, crosses thereof, and related events thereof; events T120-7, H7-1 and A5-15, crosses thereof, and related events thereof; events LL cotton 25, MON 1445, MON 531, MON15985, crosses thereof, and related events thereof; and event EH92-527-1 and related events thereof, wherein in step (1) the presence or absence of nucleic acids in a sample is detected using PCR amplification, preferably real-time PCR amplification, using the respective primer pairs from the following table:

| | | | |
|---|---|---|---|
| "Zm" | Fwd: 5' TCTCTTCCTCCTTTAGAGCTACCACTA 3' | (SEQ ID NO: 56) | |
| | Rev: 5' AATCGATCCAAAGCGAGATGA 3' | (SEQ ID NO: 57) | |
| "Bn" | Fwd: 5' CAGCTCAACAGTTTCCAAACGA 3' | (SEQ ID NO: 24) | |
| | Rev: 5' CGACCAGCCTCAGCCTTAAG 3' | (SEQ ID NO: 25) | |
| "Gm" | Fwd: 5' AACCGGTAGCGTTGCCAG 3' | (SEQ ID NO: 58) | |
| | Rev': 5' AGCCCATCTGCAAGCCTTT 3' | (SEQ ID NO: 59) | |
| "p35S" | Fwd: 5' AAAGCAAGTGGATTGATGTGATA 3' | (SEQ ID NO: 60) | |
| | Rev: 5' GGGTCTTGCGAAGGATAGTG 3' | (SEQ ID NO: 61) | |
| "tNOS" | Fwd: 5'-GATTAGAGTCCCGCAATTATACATTTAA-3' | (SEQ ID NO: 9) | |
| | Rev: 5'-TTATCCTAGKTTGCGCGCTATATTT-3' | (SEQ ID NO: 10) | |
| "Cry1Ab" | Fwd: 5'-ACCGGTTACACTCCCATCGA-3' | (SEQ ID NO: 11) | |
| | Rev: 5'-CAGCACCTGGCACGAACTC-3' | (SEQ ID NO: 12) | |
| "PAT/bar" | Fwd: 5'-CGTCAACCACTACATCGAGACAA-3' | (SEQ ID NO: 13) | |
| | Rev: 5'-GTCCACTCCTGCGGTTCCT-3' | (SEQ ID NO: 14) | |
| "PAT/pat" | Fwd: 5'-CCGCGGTTTGTGATATCGTT-3' | (SEQ ID NO: 15) | |
| | Rev: 5'-TCTTGCXACCTCTCTAGATCATCAA-3' | (SEQ ID NO: 16) | |
| "CP4-EPSPS" | Fwd: 5' GCATGCTTCACGGTGCAA 3' | (SEQ ID NO: 22) | |
| | Rev: 5' GGACCTGTGGGAGATAGACTTGTC 3' | (SEQ ID NO: 23) | |
| | Rev 1: 5' TGAAGGACCGGTGGGAGAT 3' | (SEQ ID NO: 62) | |
| | Rev 2: 5' TGAAGGACCTGTGGGAGAT 3' | (SEQ ID NO: 63) | |
| "Or" | Fwd': 5' GCTTAGGGAACAGGGAAGTAAAGT 3' | (SEQ ID NO: 51) | |
| | Rev: 5' CTTAGCATAGTCTGTGCCATCCA 3' | (SEQ ID NO: 21) | |
| "Bv" | Fwd: 5' GACCTCCATATTACTGAAAGGAAG 3' | (SEQ ID NO: 64) | |
| | Rev: 5' GAGTAATTGCTCCATCCTGTTCA 3' | (SEQ ID NO: 65) | |
| "Gs" | Fwd: 5' AGTTTGTAGGTTTTGATGTTACATTGAG 3' | (SEQ ID NO: 66) | |
| | Rev: 5' GCATCTTTGAACCGCCTACTG 3' | (SEQ ID NO: 67) | |
| "St" | Fwd: 5' GGACATGTGAAGAGACGGAGC 3' | (SEQ ID NO: 68) | |
| | Rev: 5' CCTACCTCTACCCCTCCGC 3' | (SEQ ID NO: 69). | |

2. The method according to claim 1, wherein step (1) involves detecting the presence or absence in the sample of nucleic acids comprising all nucleic acids listed under a)-c).

3. The method according to claim 1,
wherein step (1) further comprises detecting the presence or absence in the sample of nucleic acid j) "mCry3A": a nucleic acid derived from the modified crystal protein gene Cry3A of *Bacillus thuringiensis*; and/or
wherein step (1) further comprises detecting the presence or absence in the sample of one or both nucleic acids k) "cordapA": a nucleic acid derived from the lysine-insensitive dihydrodipicolinate synthase (cDHDPS) gene cordapA of *Corynebacterium glutamicum* and/or l) "Glb1": a nucleic acid derived from the Glb1 promoter of maize; and/or
wherein step (1) further comprises detecting the presence or absence in the sample of nucleic acid m) "Cry3Bb1": a nucleic acid derived from the crystal protein gene Cry3Bb1 of *Bacillus thuringiensis*; and/or
wherein step (1) further comprises detecting the presence or absence in the sample of nucleic acid n) "Bxn": a nucleic acid derived from the nitrilase gene Bxn of *Klebsiella pneumoniae* ssp. *ozaenae*; and/or
wherein step (1) further comprises detecting the presence or absence in the sample of one or both of nucleic acids r) "Cry1Ac": a nucleic acid derived from the crystal protein gene Cry1Ac of *Bacillus thuringiensis* and/or s) "Cry2Ab2": a nucleic acid derived from the crystal protein gene Cry2Ab2 of *Bacillus thuringiensis*; and/or
wherein step (1) further comprises detecting the presence or absence in the sample of nucleic acid u) "GBSS": a nucleic acid derived from the granule bound starch synthase gene Gbss of *Solanum tuberosum*.

4. The method according to claim 1, wherein step (1) further comprises detecting the presence or absence in the sample of a generic plant-derived nucleic acid, preferably derived from the chloroplastic small subunit of Rubisco gene or from the CHL-tRNA synthetase gene.

5. The method according to claim 4, wherein the presence or absence of said generic plant-derived nucleic acid is detected using PCR amplification, preferably real-time PCR amplification, using the primer pair 5' AGGTCTAADGGR-TAAGCTAC 3' (SEQ ID NO: 26) and 5' AGYCTTGATCGT-TACAAAGG 3' (SEQ ID NO: 27).

6. The method according to claim 1, wherein the amplification products are detected using a detection method that is substantially sequence non-specific, preferably using a DNA-binding fluorescent dye, more preferably using SYBR Green or PicoGreen.

7. The method according to claim 1, wherein the specificity of the amplification products is further verified, preferably using melting curve analysis (Tm) and/or size determination by gel elecrophoresis.

8. The method according to claim 1, wherein the amplification products are detected by means of a fluorophore label present in at least one primer of the primer pair, such as using Light Upon Extension (LUX™) technology.

9. The method according to claim 1, wherein the sample comprises plants or parts thereof, including flowers, tepals, petals, sepals, anthers, pollen, seeds, fruits, pericarp, pods, leaves, petioles, stems, roots, rhizomes, stolons, tubers or shoots, or portions thereof, plant cells, plant protoplasts and/or plant tissues, and/or plant-derived material, preferably food or feed material, including processed food or feed material.

10. The method according to claim 1, wherein in step (1) the presence or absence of nucleic acids in a sample is detected using PCR amplification, preferably real-time PCR amplification, using the respective primer pairs from the C following table:

| | | |
|---|---|---|
| "Zm" | Fwd: 5' CgTCgTTTCCCATCTCTTCCTCC 3'<br>Rev: 5' CCACTCCgAgACCCTCAgTC 3' | (SEQ ID NO: 1)<br>(SEQ ID NO: 2) |
| "Zm" | Fwd: 5' TCTCTTCCTCCTTTAGAGCTACCACTA 3'<br>Rev: 5' AATCGATCCAAAGCGAGATGA 3' | (SEQ ID NO: 56)<br>(SEQ ID NO: 57) |
| "Bn" | Fwd11: 5' GAGAATGAGGAGGACCAAGCTC 3'<br>Fwd2: 5'GGTGAGCTGTATAATCGAGCGA 3'<br>Rev: 5' GGCGCAGCATCGGCT 3' | (SEQ ID NO: 4)<br>(SEQ ID NO: 79)<br>(SEQ ID NO: 3) |
| "Bn" | Fwd: 5' CAGCTCAACAGTTTCCAAACGA 3'<br>Rev: 5' CGACCAGCCTCAGCCTTAAG 3' | (SEQ ID NO: 24)<br>(SEQ ID NO: 25) |
| "Gm" | Fwd: 5' CATTACCTATgATgCCTCCACC 3'<br>Rev: 5' AAgCACgTCATgCgATTC 3'<br>Rev': 5' AAgCACgTCATgCgATTCC 3' | (SEQ ID NO: 5)<br>(SEQ ID NO: 6)<br>(SEQ ID NO: 49) |
| "Gm" | Fwd: 5' AACCGGTAGCGTTGCCAG 3'<br>Rev': 5' AGCCCATCTGCAAGCCTTT 3' | (SEQ ID NO: 58)<br>(SEQ ID NO: 59) |
| "p35S" | Fwd: 5'-GACAGTGGTCCCAAAGATGG-3'<br>Rev: 5'-GTCTTGCGAAGGATAGTGGG-3' | (SEQ ID NO: 7)<br>(SEQ ID NO: 8) |
| "p35S" | Fwd: 5' AAAGCAAGTGGATTGATGTGATA 3'<br>Rev: 5' GGGTCTTGCGAAGGATAGTG 3' | (SEQ ID NO: 60)<br>(SEQ ID NO: 61) |
| "tNOS" | Fwd: 5'-GATTAGAGTCCCGCAATTATACATTTAA-3'<br>Rev: 5'-TTATCCTAGKTTGCGCGCTATATTT-3' | (SEQ ID NO: 9)<br>(SEQ ID NO: 10) |
| "tNOS" | Fwd: 5' CGTTCAAACATTTGGCAATAAAG 3'<br>Rev: 5' AAATGTATAATTGCGGGACTCTAATC 3' | (SEQ ID NO: 28)<br>(SEQ ID NO: 29) |
| "Cry1Ab" | Fwd: 5'-ACCGGTTACACTCCCATCGA-3'<br>Rev: 5'-CAGCACCTGGCACGAACTC-3' | (SEQ ID NO: 11)<br>(SEQ ID NO: 12) |
| "Cry1Ab" | Fwd: 5' GACATCATCTGGGGYATCTT 3'<br>Rev: 5' GCGCTGTTCATGTCGTTGAA 3' | (SEQ ID NO: 30)<br>(SEQ ID NO: 31) |
| "Cry1Ab" | Fwd: 5' ACGCCTTCCTGGTGCAAA 3'<br>Rev: 5' CCTGGTTCCTGGCGAACTC 3' | (SEQ ID NO: 47)<br>(SEQ ID NO: 48) |
| "PAT/bar" | Fwd: 5'-CGTCAACCACTACATCGAGACAA-3'<br>Rev: 5'-GTCCACTCCTGCGGTTCCT-3' | (SEQ ID NO: 13)<br>(SEQ ID NO: 14) |
| "PAT/pat" | Fwd: 5'-CCGCGGTTTGTGATATCGTT-3'<br>Rev: 5'-TCTTGCAACCTCTCTAGATCATCAA-3' | (SEQ ID NO: 15)<br>(SEQ ID NO: 16) |
| "CP4-EPSPS" | Fwd1: 5'-GGCTCTGAGCTTCGTCCTCCTAAGG-3'<br>Fwd1': 5'-GGCTCTGAGCTTCGTCCTCTTAAGG-3'<br>Fwd2: 5'-ATCAGTGGCTACAGCCTGCAT-3'<br>Rev: 5'-GAATGCGGACGGTTCCGGAAAG-3' | (SEQ ID NO: 17)<br>(SEQ ID NO: 50)<br>(SEQ ID NO: 18)<br>(SEQ ID NO: 19) |
| "CP4-EPSPS" | Fwd: 5' GCATGCTTCACGGTGCAA 3'<br>Rev: 5' GGACCTGTGGGAGATAGACTTGTC 3'<br>Rev 1: 5' TGAAGGACCGGTGGGAGAT 3'<br>Rev 2: 5' TGAAGGACCTGTGGGAGAT 3' | (SEQ ID NO: 22)<br>(SEQ ID NO: 23)<br>(SEQ ID NO: 62)<br>(SEQ ID NO: 63) |
| "Or" | Fwd: 5' GCTTAGGGAACAGGGAAGTAAAGTT 3'<br>Fwd': 5' GCTTAGGGAACAGGGAAGTAAAGT 3'<br>Rev: 5' CTTAGCATAGTCTGTGCCATCCA 3' | (SEQ ID NO: 20)<br>(SEQ ID NO: 51)<br>SEQ ID NO: 21 |
| "Bv" | Fwd: 5' GACCTCCATATTACTGAAAGGAAG 3'<br>Rev: 5' GAGTAATTGCTCCATCCTGTTCA 3' | (SEQ ID NO: 64)<br>(SEQ ID NO: 65) |
| "Gs" | Fwd: 5' AGTTTGTAGGTTTTGATGTTACATTGAG 3'<br>Rev: 5' GCATCTTTGAACCGCCTACTG 3' | (SEQ ID NO: 66)<br>(SEQ ID NO: 67) |
| "St" | Fwd: 5' GGACATGTGAAGAGACGGAGC 3'<br>Rev: 5' CCTACCTCTACCCCTCCGC 3' | (SEQ ID NO: 68)<br>(SEQ ID NO: 69) |

```
generic plant Fwd: 5' AGGTCTAADGGRTAAGCTAC 3'      (SEQ ID NO: 26)
              Rev: 5' AGYCTTGATCGTTACAAAGG 3'      (SEQ ID NO: 27)
```

11. The method according to claim 1, wherein the step (2) comprises the steps of:
 (i) defining a set "$G_{SAM}$" consisting of nucleic acids detected in step (1) as being present in the sample;
 (ii) defining one or more set of interest ("$G_X$") chosen from the group of sets comprising or consisting of sets "$G_{Bt176}$", "$G_{Bt11}$", "$G_{Bt10}$", "$G_{MON810}$", "$G_{MON863}$", "$G_{TC1507}$", "$G_{NK603}$", "$G_{T25}$", "$G_{GA21}$", "$G_{DAS-59122}$", "$G_{MIR604}$", "$G_{LY038}$", "$G_{MON88017}$", "$G_{Topas\ 19/2}$", "$G_{MS1}$", "$G_{RF1}$", "$G_{RF2}$", "$G_{MS1/RF1}$", "$G_{MS1/RF2}$", "$G_{MS8}$", "$G_{RF3}$", "$G_{MS8/RF3}$", "$G_{GT73}$", "$G_{T45}$", "$G_{Liberator\ pHoe6/Ac}$", "$G_{GS40/90pHoe6/Ac}$", "$G_{OXY235}$", "$G_{MON40-3-2}$", "$G_{MON89788}$", "$G_{A2704-12}$", "$G_{A5547-127}$", "$G_{LL62}$", "$G_{LL06}$", "$G_{LL601}$", "$G_{T120-7}$", "$G_{H7-1}$", "$G_{A5-15}$", "$G_{LL\ cotton\ 25}$", "$G_{MON1445}$", "$G_{MON531}$", "$G_{MON15985}$" and "$G_{EH92-527-1}$"; corresponding to the respective one or more transgenic plant events of interest ("X") chosen from the group comprising or consisting of events Bt176, Bt11, Bt10, MON810, MON863, TC1507, NK603, T25, A21, DAS-59122, MIR604, LY038, MON88017, Topas 19/2, MS1, RF1, RF2, MS1/RF1, MS1/RF2, MS8, RF3, MS8/RF3, G T73, T45, Liberator pHoe6/Ac, GS40/90pHoe6/Ac, OXY235, MON40-3-2, MON89788, A2704-12, A5547-127, LL62, LL06, LL601, T120-7, H7-1, A5-15, LL cotton 25, MON1445, MON531, MON15985 and EH92-527-1, wherein:
  $G_{Bt176}$ ∈ {Zm; p35S; Cry1Ab; PAT/bar},
  $G_{Bt11}$ ∈ {Zm; p35S; tNOS; Cry1Ab; PAT/pat},
  $G_{Bt10}$ ∈ {Zm; p35S; tNOS; Cry1Ab; PAT/pat},
  $G_{MON810}$ ∈ {Zm; p35S; tNOS; Cry1Ab},
  $G_{MON863}$ ∈ {Zm; p35S; tNOS},
  $G_{TC1507}$ ∈ {Zm; p35S; PAT/pat},
  $G_{NK603}$ ∈ {Zm; p35S; tNOS; CP4-EPSPS},
  $G_{T25}$ ∈ {Zm; p35S; PAT/pat},
  $G_{GA21}$ ∈ {Zm; tNOS},
  $G_{DAS-59122}$ ∈ {Zm; p35S; PAT/bar},
  $G_{MIR604}$ ∈ {Zm; tNOS; mCry3A}, or $G_{MIR604}$ ∈ {Zm; tNOS}
  $G_{LY038}$ ∈ {Zm; p35S; tNOS; cordapA; Glb1}, or $G_{LY038}$ ∈ {Zm; p35S; tNOS},
  $G_{MON88017}$ ∈ {Zm; p35S; tNOS; CP4-EPSPS; Cry3Bb1}, or $G_{MON88017}$ ∈ {Zm; p35S; tNOS; CP4-EPSPS},
  $G_{Topas\ 19/2}$ ∈ {Bn; p35S; PAT/pat},
  $G_{MS1}$ ∈ {Bn; tNOS; PAT/bar},
  $G_{RF1}$ ∈ {Bn; tNOS; PAT/bar},
  $G_{RF2}$ ∈ {Bn; tNOS; PAT/bar},
  $G_{MS1/RF1}$ ∈ {Bn; tNOS; PAT/bar},
  $G_{MS1/RF2}$ ∈ {Bn; tNOS; PAT/bar},
  $G_{MS8}$ ∈ {Bn; tNOS; PAT/bar},
  $G_{RF3}$ ∈ {Bn; tNOS; PAT/bar},
  $G_{MS8/RF3}$ ∈ {Bn; tNOS; PAT/bar},
  $G_{GT73}$ ∈ {Bn; CP4-EPSPS},
  $G_{T45}$ ∈ {Bn; p35S; PAT/pat},
  $G_{Liberator\ pHoe6/Ac}$ ∈ {Bn; p35S; PAT/pat},
  $G_{GS40/90pHoe6/Ac}$ ∈ {Bn; p35S; PAT/pat},
  $G_{OXY235}$ ∈ {Bn; p35S; Bxn}, or $G_{OXY235}$ ∈ {Bn; p35S};
  $G_{MON40-3-2}$ ∈ {Gm; p35S; tNOS; CP4-EPSPS},
  $G_{MON89788}$ ∈ {Gm; CP4-EPSPS}
  $G_{A2704-12}$ ∈ {Gm; p35S; PAT/pat},
  $G_{A5547-127}$ ∈ {Gm; p35S; PAT/pat},
  $G_{LL62}$ ∈ {Or; p35S; PAT/bar},
  $G_{LL06}$ ∈ {Or; p35S; PAT/bar}
  $G_{LL601}$ ∈ {Or; p35S; tNOS; PAT/bar},
  $G_{T120-7}$ ∈ {Bv; p35S; PAT/pat},
  $G_{H7-1}$ ∈ {Bv; p35S; CP4-EPSPS},
  $G_{A5-15}$ ∈ {Bv; p35S; tNOS; CP4-EPSPS},
  $G_{LL\ cotton\ 25}$ ∈ {Gs; p35S; tNOS; PAT/bar},
  $G_{MON1445}$ ∈ {Gs; p35S; tNOS; CP4-EPSPS},
  $G_{MON531}$ ∈ {Gs; p35S; tNOS; cry1Ac}, or $G_{MON531}$ ∈ {Gs; p35S; tNOS}
  $G_{MON15985}$ ∈ {Gs; p35S; tNOS; cry1Ac; cry2Ab2} or $G_{MON15985}$ ∈ {Gs; p35S; tNOS}, and
  $G_{EH92-527-1}$ ∈ {St; tNOS; Gbss} or $G_{EH92-527-1}$ ∈ {St; tNOS};
 (iii) performing for each set of interest $G_X$ logical operations:
  if $G_X$ equals $G_{SAM}$ ($G_X=G_{SAM}$), then material derived from the transgenic plant event X or from a cross thereof, or from an event related thereto, is potentially present in the sample;
  if $G_X$ is a proper subset of $G_{SAM}$ ($G_X \subset G_{SAM}$), then material derived from transgenic plant event X or from a cross thereof, or from an event related thereto, is potentially present in the sample;
  if $G_X$ does not equal $G_{SAM}$ and $G_X$ is not a proper subset of $G_{SAM}$, ($G_X \neq G_{SAM}$ and $G_X \not\subset G_{SAM}$), then material derived from transgenic plant event X or from a cross thereof, or from an event related thereto, is absent from the sample.

12. The method according to claim 11, wherein if $G_X$ equals $G_{SAM}$, and if no one set or the sum of two or more sets chosen from the group comprising or consisting of $G_{Bt176}$, $G_{Bt11}$, $G_{Bt10}$, $G_{MON810}$, $G_{MON863}$, $G_{TC1507}$, $G_{NK603}$, $G_{T25}$, $G_{GA21}$, $G_{DAS-59122}$, $G_{MIR604}$, $G_{LY038}$, $G_{MON88017}$, $G_{Topas\ 19/2}$, $G_{MS1}$, $G_{RF1}$, $G_{RF2}$, $G_{MS1/RF1}$, $G_{MS1/RF2}$, $G_{MS8}$, $G_{RF3}$, $G_{MS8/RF3}$, $G_{GT73}$, $G_{T45}$, $G_{Liberator\ pHoe6/Ac}$, $G_{GS40/90pHoe6/Ac}$, $G_{OXY235}$, $G_{MON40-3-2}$, $G_{MON89788}$, $G_{A2704-12}$, $G_{A5547-127}$, $G_{LL62}$, $G_{LL06}$, $G_{LL601}$, $G_{T120-7}$, $G_{H7-1}$, $G_{A5-15}$, $G_{LL\ cotton\ 25}$, $G_{MON1445}$, $G_{MON531}$, $G_{MON15985}$ other than $G_X$ equals $G_X$, then material derived from transgenic plant event X or from a cross thereof, or from an event related thereto, is present in the sample.

13. The method according to claim 11, wherein nucleic acids chosen from the group comprising or consisting of "Zm", "Bn", "Gm", "p35S", "tNOS", "Cry1Ab", "PAT/bar", "PAT/pat", "CP4-EPSPS", "mCry3A", "cordap A", "Glb1", "Cry3Bb1", "Bxn", "Or", "Bv", "Gs", "Cry1Ac", "Cry2ab2", "St" and "Gbss" are assigned respective unique values "$V_{Zm}$", "$V_{Bn}$", "$V_{Gm}$", "$V_{p35S}$", "$V_{tNOS}$", "$V_{Cry1Ab}$", "$V_{PAT/bar}$", "$V_{PAT/pat}$", "$V_{CP4-EPSPS}$", "$V_{mCry3A}$", "$V_{cordap\ A}$", "$V_{Glb1}$", "$V_{Cry3Bb1}$", "$V_{Bxn}$", "$V_{Or}$", "$V_{Bv}$", "$V_{Gs}$", "$V_{Cry1Ac}$", "$V_{Cry2ab2}$", "$V_{St}$" and "$V_{Gbss}$"; wherein each set of interest $G_X$ is assigned a value "$VG_X$" chosen from the group comprising consisting of values "$VG_{Bt176}$", "$VG_{Bt11}$", "$VG_{Bt10}$", "$VG_{MON810}$", "$VG_{MON863}$", "$VG_{TC1507}$", "$VG_{NK603}$", "$VG_{T25}$", "$VG_{GA21}$", "$VG_{DAS-59122}$", "$VG_{MIR604}$", "$VG_{LY038}$", "$VG_{MON88017}$", "$VG_{Topas\ 19/2}$", "$VG_{MS1}$", "$VG_{RF1}$", "$VG_{RF2}$", "$VG_{MS1/RF1}$", "$VG_{MS1/RF2}$", "$VG_{MS8}$", "$VG_{RF3}$", "$VG_{MS8/RF3}$", "$VG_{GT73}$", "$VG_{T45}$", "$VG_{Liberator\ pHoe6/Ac}$", "$VG_{GS40/90pHoe6/Ac}$", "$VG_{OXY235}$", "$VG_{MON40-3-2}$", "$VG_{MON89788}$", "$VG_{A2704-12}$", "$VG_{A5547-127}$", "$VG_{LL62}$", "$VG_{LL06}$", "$VG_{LL601}$", "$VG_{T120-7}$", "$VG_{H7-1}$", "$VG_{A5-15}$", "$VG_{LL\ cotton\ 25}$", "$VG_{MON1445}$", "$VG_{MON531}$", "$VG_{MON15985}$" and "$VG_{EH92-527-1}$", wherein:

$VG_{Bt176} = V_{Zm} \times V_{p35S} \times V_{Cry1Ab} \times V_{PAT/bar}$,
$VG_{Bt11} = V_{Zm} \times V_{p35S} \times V_{tNOS} \times V_{Cry1Ab} \times V_{PAT/pat}$,
$VG_{Bt10} = V_{Zm} \times V_{p35S} \times V_{tNOS} \times V_{Cry1Ab} \times V_{PAT/pat}$,
$VG_{MON810} = V_{Zm} \times V_{p35S} \times V_{tNOS} \times V_{Cry1Ab}$,
$VG_{MON863} = V_{Zm} \times V_{p35S} \times V_{tNOS}$,
$VG_{TC1507} = V_{Zm} \times V_{p35S} \times V_{PAT/pat}$,
$VG_{NK603} = V_{Zm} \times V_{p35S} \times V_{tNOS} \times V_{CP4-EPSPS}$,
$VG_{T25} = V_{Zm} \times V_{p35S} \times V_{PAT/pat}$,
$VG_{GA21} = V_{Zm} \times V_{tNOS}$,
$VG_{DAS-59122} = V_{Zm} \times V_{p35S} \times V_{PAT/bar}$,
$VG_{MIR604} = V_{Zm} \times V_{tNOS} \times V_{mCry3A}$, or $VG_{MIR604} = V_{Zm} \times V_{tNOS}$,
$VG_{LY038} = V_{Zm} \times V_{p35S} \times V_{tNOS} \times V_{cordapA} \times V_{Glb1}$, or $VG_{LY038} = V_{Zm} \times V_{p35S} \times V_{tNOS}$,
$VG_{MON88017} = V_{Zm} \times V_{p35S} \times V_{tNOS} \times V_{CP4-EPSP} \times V_{Cry3Bb1}$, or $VG_{MON88017} = V_{Zm} \times V_{p35S} \times V_{tNOS} \times V_{CP4-EPSP}$,
$VG_{Topas\ 19/2} = V_{Bn} \times V_{p35S} \times V_{PAT/pat}$,
$VG_{MS1} = V_{Bn} \times V_{tNOS} \times V_{PAT/bar}$,
$VG_{RF1} = V_{Bn} \times V_{tNOS} \times V_{PAT/bar}$,
$VG_{RF2} = V_{Bn} \times V_{tNOS} \times V_{PAT/bar}$,
$VG_{MS8} = V_{Bn} \times V_{tNOS} \times V_{PAT/bar}$,
$VG_{RF3} = V_{Bn} \times V_{tNOS} \times V_{PAT/bar}$,
$VG_{MS1/RF1} = V_{Bn} \times V_{tNOS} \times V_{PAT/bar}$,
$VG_{MS1/RF2} = V_{Bn} \times V_{tNOS} \times V_{PAT/bar}$,
$VG_{MS8/RF3} = V_{Bn} \times V_{tNOS} \times V_{PAT/bar}$,
$VG_{GT73} = V_{Bn} \times V_{CP4-EPSPS}$,
$VG_{T45} = V_{Bn} \times V_{p35S} \times V_{PAT/pat}$,
$VG_{Liberator\ pHoe6/Ac} = V_{Bn} \times V_{p35S} \times V_{PAT/pat}$,
$VG_{GS40/90pHoe6/Ac} = V_{Bn} \times V_{p35S} \times V_{PAT/pat}$,
$VG_{OXY235} = V_{Bn} \times V_{p35S} \times V_{Bxn}$, or $VG_{OXY235} = V_{Bn} \times V_{p35S}$,
$VG_{MON40-3-2} = V_{Gm} \times V_{p35S} \times V_{tNOS} \times V_{CP4-EPSPS}$,
$VG_{MON89788} = V_{Gm} \times V_{CP4-EPSPS}$,
$VG_{A2704-12} = V_{Gm} \times V_{p35S} \times V_{PAT/pat}$,
$VG_{A5547-127} = V_{Gm} \times V_{p35S} \times V_{PAT/pat}$,
$VG_{LL62} = V_{Or} \times V_{p35S} \times V_{PAT/bar}$,
$VG_{LL06} = V_{Or} \times V_{p35S} \times V_{PAT/bar}$,
$VG_{LL601} = V_{Or} \times V_{p35S} \times V_{tNOS} \times V_{PAT/bar}$,
$VG_{T120-7} = V_{Bv} \times V_{p35S} \times V_{PAT/pat}$,
$VG_{H7-1} = V_{Bv} \times V_{p35S} \times V_{CP4-EPSPS}$,
$VG_{A5-15} = V_{Bv} \times V_{p35S} \times V_{tNOS} \times V_{CP4-EPSPS}$,
$VG_{LL\ cotton\ 25} = V_{Gs} \times V_{p35S} \times V_{tNOS} \times V_{PAT/bar}$,
$VG_{MON1445} = V_{Gs} \times V_{p35S} \times V_{tNOS} \times V_{CP4-EPSPS}$,
$VG_{MON531} = V_{Gs} \times V_{p35S} \times V_{tNOS} \times V_{Cry1Ac}$, or $VG_{MON531} = V_{Gs} \times V_{p35S} \times V_{tNOS}$,
$VG_{MON15985} = V_{Gs} \times V_{p35S} \times V_{tNOS} \times V_{Cry1Ac} \times V_{Cry2Ab2}$, or $VG_{MON15985} = V_{Gs} \times V_{p35S} \times V_{tNOS}$,
and $VG_{EH92-527-1} V_{St} \times V_{tNOS} \times V_{Gbss}$, or $VG_{EH92-527-1} = V_{St} \times V_{tNOS}$, and wherein the set $G_{SAM}$ is assigned a value "$VG_{SAM}$" which is a multiple of the unique values assigned to the nucleic acids detected in step (1) as being present in the sample;

and wherein step (iii) comprises performing for each set of interest $G_X$ logical operations:

if $VG_{SAM}/VG_X$ equals 1, then material derived from transgenic plant event X or from a cross thereof, or from an event related thereto, is potentially present in the sample;

if $VG_{SAM}/VG_X$ equals one or a multiple of two or more values chosen from a group comprising or consisting of values $V_{Zm}$, $V_{Bn}$, $V_{Gm}$, $V_{p35S}$, $V_{tNOS}$, $V_{Cry1Ab}$, $V_{PAT/bar}$, $V_{PAT/pat}$, $V_{CP4-EPSPS}$, $V_{mCry3A}$, $V_{cordap\ A}$, $V_{Glb1}$, $V_{Cry3Bb1}$, $V_{Bxn}$, $V_{Or}$, $V_{Bv}$, $V_{Gs}$, $V_{Cry1Ac}$, $V_{Cry2ab2}$, $V_{St}$ and $V_{Gbss}$, then material derived from transgenic plant event X or from a cross thereof, or from an event related thereto, is potentially present in the sample;

if $VG_{SAM}/VG_X$ does not equal 1 and does not equal one value or a multiple of two or more values chosen from a group comprising or consisting of values $V_{Zm}$, $V_{Bn}$, $V_{Gm}$, $V_{p35S}$, $V_{tNOS}$, $V_{Cry1Ab}$, $V_{PAT/bar}$, $V_{PAT/pat}$, $V_{CP4-EPSPS}$, $V_{mCry3A}$, $V_{cordap\ A}$, $V_{Glb1}$, $V_{Cry3Bb1}$, $V_{Bxn}$, $V_{Or}$, $V_{Bv}$, $V_{Gs}$, $V_{Cry1Ac}$, $V_{Cry2ab2}$, $V_{St}$ and $V_{Gbss}$, then material derived from transgenic plant event X or from a cross thereof, or from an event related thereto, is absent from the sample.

14. The method according to claim 13, wherein if $VG_{SAM}/VG_X$ equals 1, and if no one value or the multiple of two or more values of sets chosen from a group comprising or consisting of: $VG_{Bt176}$, $VG_{Bt11}$, $VG_{Bt10}$, $VG_{MON810}$, $VG_{MON863}$, $VG_{TC1507}$, $VG_{NK603}$, $VG_{T25}$, $VG_{GA21}$, $VG_{DAS-59122}$, $VG_{MIR604}$, $VG_{LY038}$, $VG_{MON88017}$, $VG_{Topas\ 19/2}$, $VG_{MS1}$, $VG_{RF1}$, $VG_{RF2}$, $VG_{MS1/RF1}$, $VG_{MS1/RF2}$, $VG_{MS8}$, $VG_{RF3}$, $VG_{MS8/RF3}$, $VG_{GT73}$, $VG_{T45}$, $VG_{Liberator\ pHoe6/Ac}$, $VG_{GS40/90pHoe6/Ac}$, $VG_{OXY235}$, $VG_{MON40-3-2}$, $VG_{MON89788}$, $VG_{A2704-12}$, $VG_{A5547-127}$, $VG_{LL62}$, $VG_{LL06}$, $VG_{LL601}$, $VG_{T120-7}$, $VG_{H7-1}$, $VG_{A5-15}$, $VG_{LL\ cotton\ 25}$, $VG_{MON1445}$, $VG_{MON531}$, $VG_{MON15985}$ and $VG_{EH92-527-1}$ other than $VG_X$ equals $VG_X$, then material derived from transgenic plant event X or from a cross thereof, or from an event related thereto, is present in the sample.

15. The method according claim 13, wherein values $V_{Zm}$, $V_{Bn}$, $V_{Gm}$, $V_{p35S}$, $V_{tNOS}$, $V_{Cry1Ab}$, $V_{PAT/bar}$, $V_{PAT/pat}$, $V_{CP4-EPSPS}$, $V_{mCry3A}$, $V_{cordap\ A}$, $V_{Glb1}$, $V_{Cry3Bb1}$, $V_{Bxn}$, $V_{Or}$, $V_{Bv}$, $V_{Gs}$, $V_{Cry1Ac}$, $V_{Cry2ab2}$, $V_{St}$ and $V_{Gbss}$ are unique prime numbers, and wherein step (iii) comprises performing for each set of interest $G_X$ logical operations, if $VG_{SAM}/VG_X$ equals 1, then material derived from transgenic plant event X or from a cross thereof, or from an event related thereto, is potentially present in the sample;

if $VG_{SAM}/VG_X$ is an integer greater than 1, then material derived from transgenic plant event X or from a cross thereof, or from an event related thereto, is potentially present in the sample;

if $VG_{SAM}/VG_X$ is not an integer, then material derived from transgenic plant event X or from a cross thereof, or from an event related thereto, is absent from the sample.

16. The method according to claim 1, wherein step (2) is carried out by a computing device.

17. The method according to claim 1, wherein the PCR amplification of the nucleic acids is performed simultaneously at the same temperature cycling conditions.

18. The method according to claim 1, wherein the PCR amplification of two or more of the nucleic acids is multiplexed.

19. A computing device programmed to carry out step (2) of the method according to claim 1; or a data carrier, that is not a carrier wave, comprising instructions for a programmable computing device to carry out the step (2) of the method according to claim 1.

* * * * *